United States Patent
Yodfat et al.

(10) Patent No.: US 12,168,113 B2
(45) Date of Patent: Dec. 17, 2024

(54) PATCH PUMP SYSTEMS AND APPARATUS FOR MANAGING DIABETES, AND METHODS THEREOF

(71) Applicant: Triple Jump Israel Ltd., Yokneam Illit (IL)

(72) Inventors: Ofer Yodfat, Modi'in (IL); Guy Shinar, Ramat Gan (IL); Yishai Ben-David, Givaat Ella (IL)

(73) Assignee: TRIPLE JUMP ISRAEL LTD., Yokneam Illit (IL)

( * ) Notice: Subject to any disclaimer, the term of this patent is extended or adjusted under 35 U.S.C. 154(b) by 0 days.

(21) Appl. No.: 18/118,066

(22) Filed: Mar. 6, 2023

(65) Prior Publication Data

US 2024/0001028 A1    Jan. 4, 2024

Related U.S. Application Data

(62) Division of application No. 16/622,898, filed as application No. PCT/IL2018/050668 on Jun. 15, 2018, now Pat. No. 11,596,733.

(60) Provisional application No. 62/519,982, filed on Jun. 15, 2017.

(51) Int. Cl.
*A61M 5/142* (2006.01)
*A61M 5/14* (2006.01)

(52) U.S. Cl.
CPC . *A61M 5/14248* (2013.01); *A61M 2005/1402* (2013.01); *A61M 2005/14252* (2013.01); *A61M 2005/14268* (2013.01)

(58) Field of Classification Search
CPC .......... A61M 5/14244; A61M 5/14248; A61M 5/16809; A61M 2005/14268; A61M 2005/14252

See application file for complete search history.

(56) References Cited

U.S. PATENT DOCUMENTS

| | | | |
|---|---|---|---|
| 4,306,976 A | 12/1981 | Bazzato | |
| 5,092,856 A | 3/1992 | Johnston | |
| 5,135,485 A | 8/1992 | Cohen et al. | |
| 5,803,712 A | 9/1998 | Davis et al. | |
| 6,485,461 B1 | 11/2002 | Mason et al. | |
| 8,262,617 B2 | 9/2012 | Aeschlimann et al. | |
| 8,277,415 B2 | 10/2012 | Mounce et al. | |
| 8,529,513 B2 | 9/2013 | Peter et al. | |
| 8,573,027 B2 | 11/2013 | Rosinko et al. | |

(Continued)

FOREIGN PATENT DOCUMENTS

| | | |
|---|---|---|
| CN | 1471413 A | 1/2004 |
| CN | 1874809 A | 12/2006 |

(Continued)

OTHER PUBLICATIONS

Extended European Search Report, dated Apr. 26, 2021, for European Application No. 18851689.2, 9 pages.

(Continued)

*Primary Examiner* — Laura A Bouchelle
(74) *Attorney, Agent, or Firm* — COOLEY LLP

(57) ABSTRACT

Embodiments of the current disclosure are directed toward systems, devices and methods for diabetes management. In particular, the present disclosure relates to systems, devices and methods for dispensing insulin to a patient using a miniaturized and portable patch pump.

15 Claims, 83 Drawing Sheets

(56) References Cited

U.S. PATENT DOCUMENTS

| | | | |
|---|---|---|---|
| 9,227,010 B2 * | 1/2016 | Neta | A61M 5/14244 |
| 9,250,106 B2 | 2/2016 | Rosinko et al. | |
| 9,314,564 B2 | 4/2016 | Imhof et al. | |
| 9,364,185 B2 | 6/2016 | Strickland | |
| 9,415,158 B2 | 8/2016 | Miller et al. | |
| 9,750,873 B2 | 9/2017 | Brown et al. | |
| 9,798,859 B2 | 10/2017 | Yodfat et al. | |
| 9,942,091 B2 | 4/2018 | Harvey et al. | |
| 10,010,674 B2 | 7/2018 | Rosinko et al. | |
| 10,434,254 B2 | 10/2019 | Imhof et al. | |
| 10,438,696 B2 | 10/2019 | Shapley et al. | |
| 10,583,244 B2 | 3/2020 | Yodfat et al. | |
| 10,811,129 B2 | 10/2020 | Bush et al. | |
| 11,241,534 B2 | 2/2022 | Miller et al. | |
| 11,554,209 B2 | 1/2023 | Yodfat et al. | |
| 11,596,733 B2 | 3/2023 | Yodfat et al. | |
| 2005/0101912 A1 | 5/2005 | Faust et al. | |
| 2007/0088271 A1 | 4/2007 | Richards | |
| 2008/0255516 A1 | 10/2008 | Yodfat et al. | |
| 2009/0088694 A1 | 4/2009 | Carter et al. | |
| 2009/0099521 A1 | 4/2009 | Gravesen et al. | |
| 2009/0287180 A1 | 11/2009 | Diperna | |
| 2010/0008795 A1 | 1/2010 | Diperna | |
| 2010/0145303 A1 | 6/2010 | Yodfat et al. | |
| 2011/0054399 A1 | 3/2011 | Chong et al. | |
| 2011/0137255 A1 | 6/2011 | Nielsen et al. | |
| 2011/0196308 A1 | 8/2011 | Kodgule et al. | |
| 2012/0022453 A1 | 1/2012 | Yodfat et al. | |
| 2012/0192951 A1 | 8/2012 | Yodfat et al. | |
| 2013/0237955 A1 | 9/2013 | Neta et al. | |
| 2014/0039392 A1 | 2/2014 | Geipel et al. | |
| 2014/0135699 A1 | 5/2014 | Gyory | |
| 2015/0029816 A1 | 1/2015 | Beyer et al. | |
| 2015/0038906 A1 | 2/2015 | Cane' | |
| 2015/0157788 A1 | 6/2015 | Gescheit et al. | |
| 2015/0265765 A1 | 9/2015 | Yavorsky et al. | |
| 2015/0265768 A1 | 9/2015 | Vazquez et al. | |
| 2017/0246379 A1 | 8/2017 | Kruse | |
| 2019/0015582 A1 | 1/2019 | Naftalovitz et al. | |
| 2019/0099551 A1 | 4/2019 | Yodfat et al. | |
| 2019/0160258 A1 | 5/2019 | Kristen | |
| 2019/0321544 A1 | 10/2019 | List | |
| 2020/0013495 A1 | 1/2020 | Torai | |
| 2020/0179594 A1 | 6/2020 | Yodfat et al. | |
| 2020/0206417 A1 | 7/2020 | Yodfat et al. | |
| 2020/0345929 A1 | 11/2020 | Ben-David et al. | |
| 2023/0256160 A1 | 8/2023 | Yodfat et al. | |

FOREIGN PATENT DOCUMENTS

| | | |
|---|---|---|
| CN | 101563120 A | 10/2009 |
| CN | 101772359 A | 7/2010 |
| CN | 101808679 A | 8/2010 |
| CN | 102186515 A | 9/2011 |
| CN | 102596289 A | 7/2012 |
| CN | 102813976 A | 12/2012 |
| CN | 102985124 A | 3/2013 |
| CN | 103370007 A | 10/2013 |
| CN | 103442749 A | 12/2013 |
| CN | 203647799 U | 6/2014 |
| CN | 203815967 U | 9/2014 |
| CN | 104203311 A | 12/2014 |
| CN | 104474606 A | 4/2015 |
| CN | 104717991 A | 6/2015 |
| CN | 106659845 A | 5/2017 |
| DE | 3708857 A1 | 9/1988 |
| EP | 0236543 A1 | 9/1987 |
| EP | 1704886 A1 | 9/2006 |
| EP | 2295093 A2 | 3/2011 |
| EP | 2295098 A1 | 3/2011 |
| EP | 2365453 A2 | 9/2011 |
| EP | 2698178 A2 | 2/2014 |
| EP | 2719410 A2 | 4/2014 |
| EP | 2763064 A2 | 8/2014 |
| EP | 2919831 A1 | 9/2015 |
| EP | 3095255 A1 | 11/2016 |
| EP | 3284507 A1 | 2/2018 |
| EP | 3335745 A1 | 6/2018 |
| JP | S56116470 A | 9/1981 |
| JP | H0388547 U | 9/1991 |
| JP | 2010526633 A | 8/2010 |
| JP | 2011516097 A | 5/2011 |
| JP | 2012513786 A | 6/2012 |
| JP | 2013503691 A | 2/2013 |
| JP | 2013503706 A | 2/2013 |
| JP | 2013544161 A | 12/2013 |
| JP | 2014050686 A | 3/2014 |
| JP | 2014531922 A | 12/2014 |
| WO | WO-2007108987 A2 | 9/2007 |
| WO | WO-2008024808 A2 | 2/2008 |
| WO | WO-2008122983 A1 | 10/2008 |
| WO | WO-2009045779 A2 | 4/2009 |
| WO | WO-2010076275 A1 | 7/2010 |
| WO | WO-2011009224 A2 | 1/2011 |
| WO | WO-2011028846 A2 | 3/2011 |
| WO | WO-2013033421 A2 | 3/2013 |
| WO | WO-2016145094 A2 | 9/2016 |
| WO | WO-2016157638 A1 | 10/2016 |
| WO | WO-2016181384 A2 | 11/2016 |
| WO | WO-2017060899 A2 | 4/2017 |
| WO | WO-2018229783 A1 | 12/2018 |
| WO | WO-2019043702 A1 | 3/2019 |

OTHER PUBLICATIONS

Extended European Search Report, dated Jan. 9, 2019, for European Application No. 16792303.6, 6 pages.

Extended European Search Report, dated Sep. 23, 2020, for European Application No. 18818197.8, 7 pages.

Extended European Search Report for European Application No. EP22184226.3 dated Jan. 23, 2023, 8 Pages.

International Preliminary Report on Patentability, dated Dec. 17, 2019, for International Application No. PCT/IL2018/050668, 6 pages.

International Preliminary Report on Patentability, dated Mar. 3, 2020, for International Application No. PCT/IL2018/050952, 7 pages.

International Preliminary Report on Patentability, dated Nov. 14, 2017, for International Application No. PCT/IL2016/050481, 6 pages.

International Search Report and Written Opinion, mailed Dec. 6, 2016, for International Application No. PCT/IL2016/050481, 9 pages.

International Search Report and Written Opinion, mailed Dec. 6, 2018, for International Application No. PCT/IL2018/050952, 9 pages.

International Search Report and Written Opinion, mailed Oct. 4, 2018, for International Application No. PCT/IL2018/050668, 8 pages.

Invitation to pay additional search fees, mailed Sep. 20, 2016, for International Application No. PCT/IL2016/050481, 2 pages.

Office Action in Japanese Patent Application No. 2021-036270 mailed Dec. 27, 2021, and English translation, 7 pages.

* cited by examiner

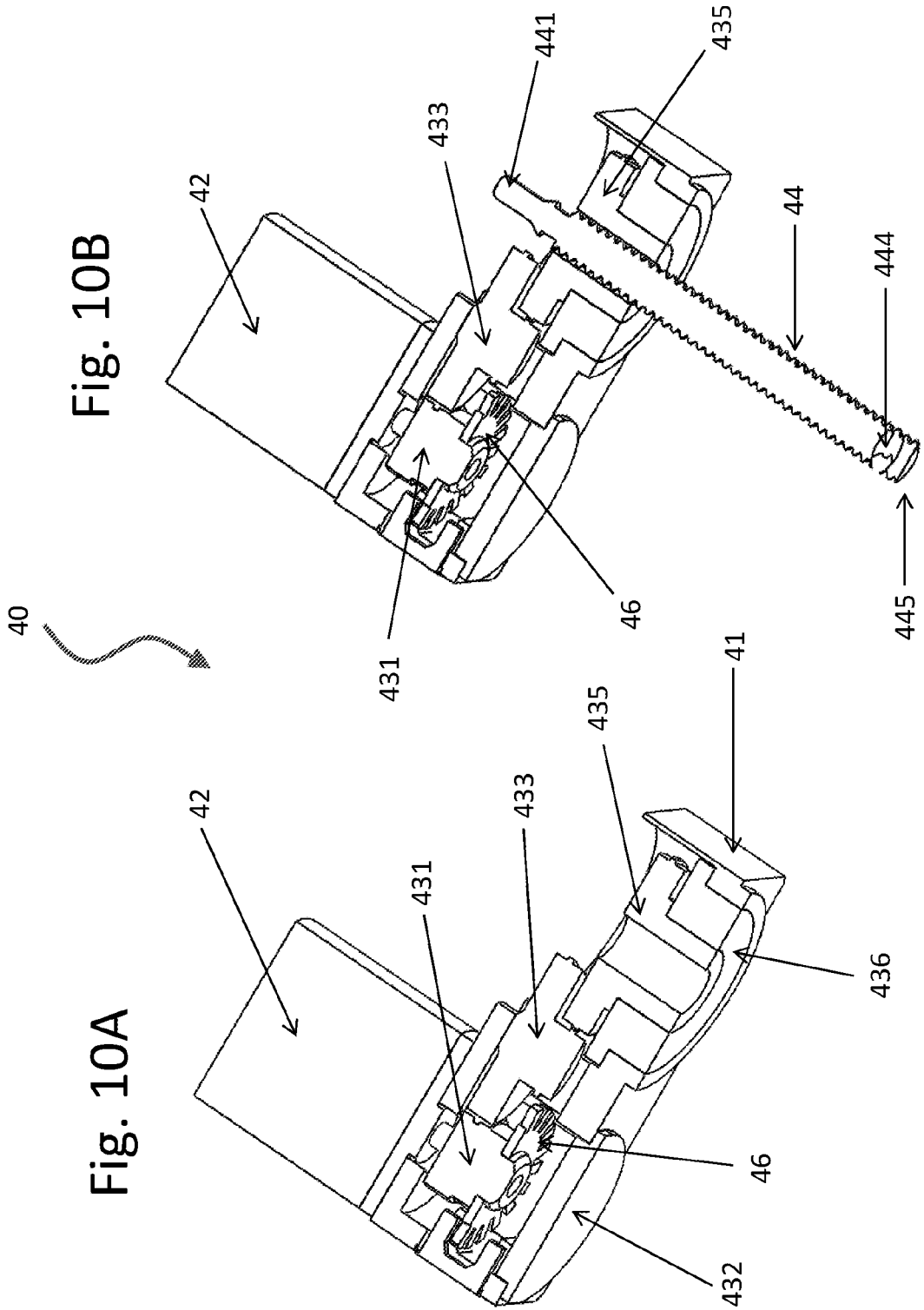

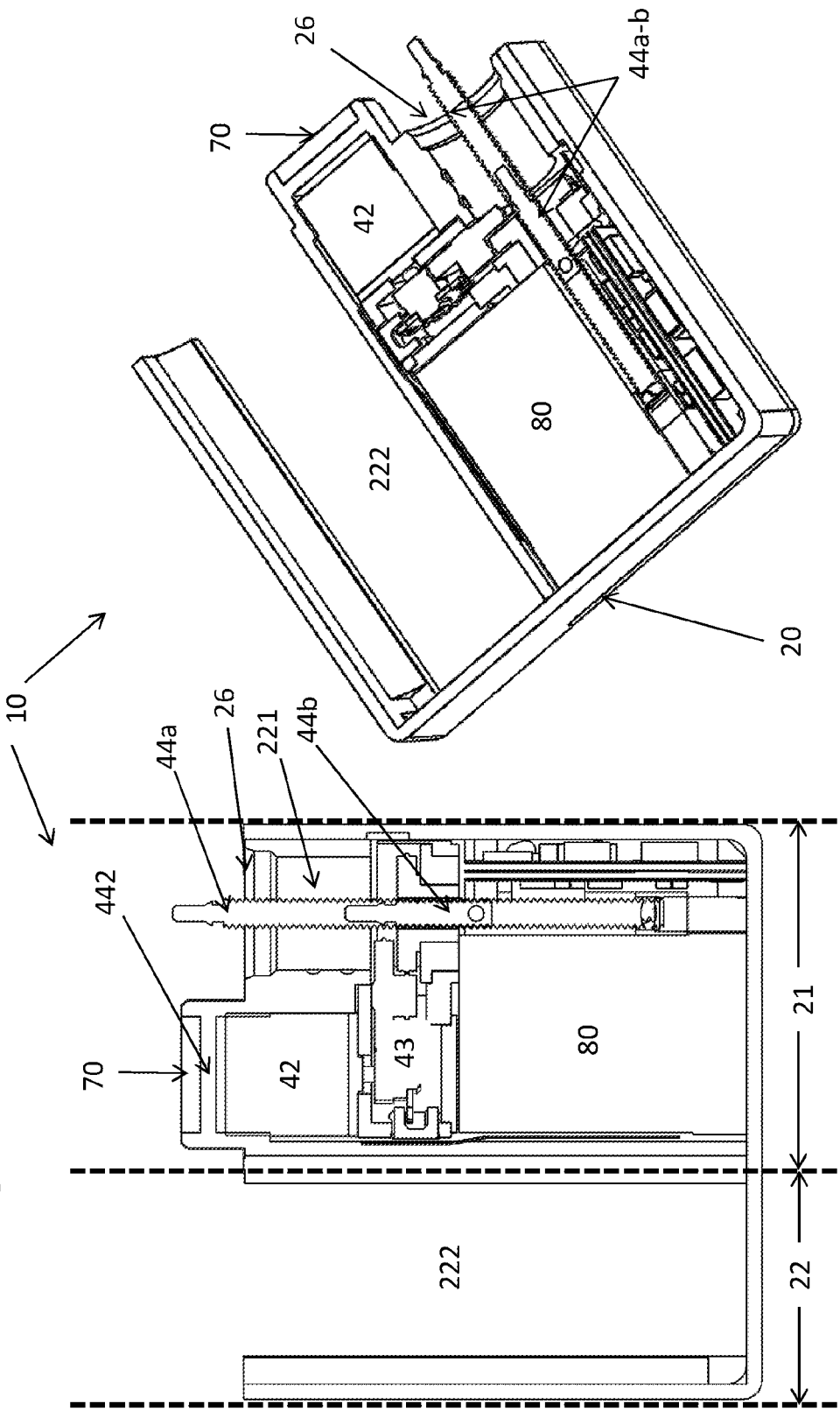
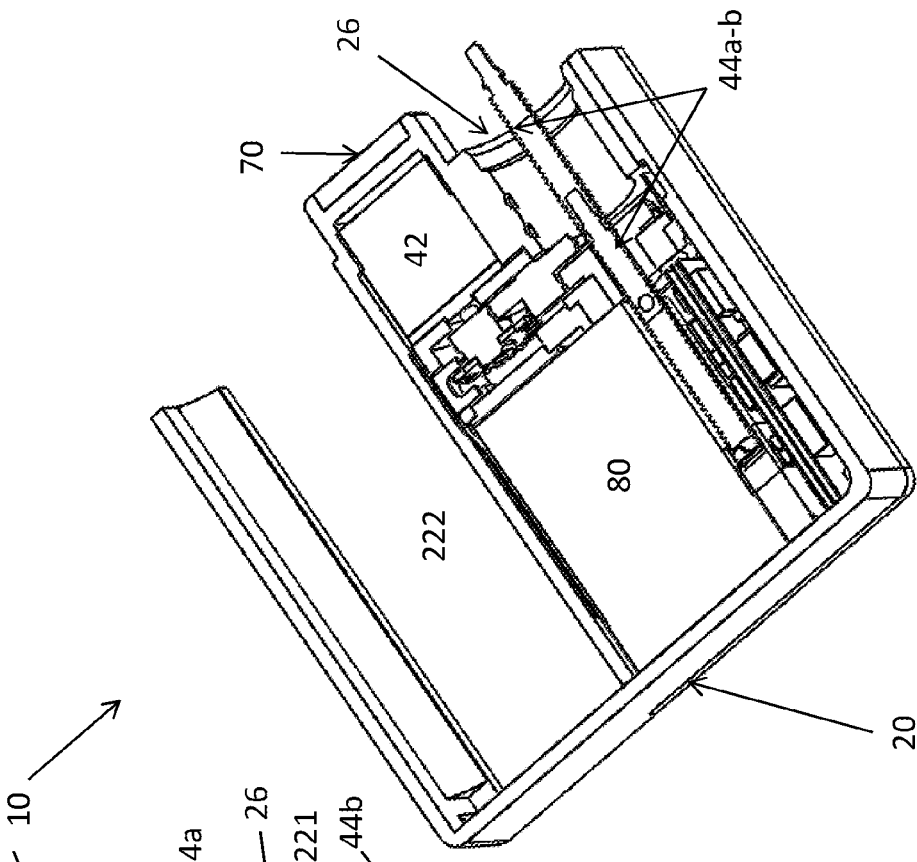

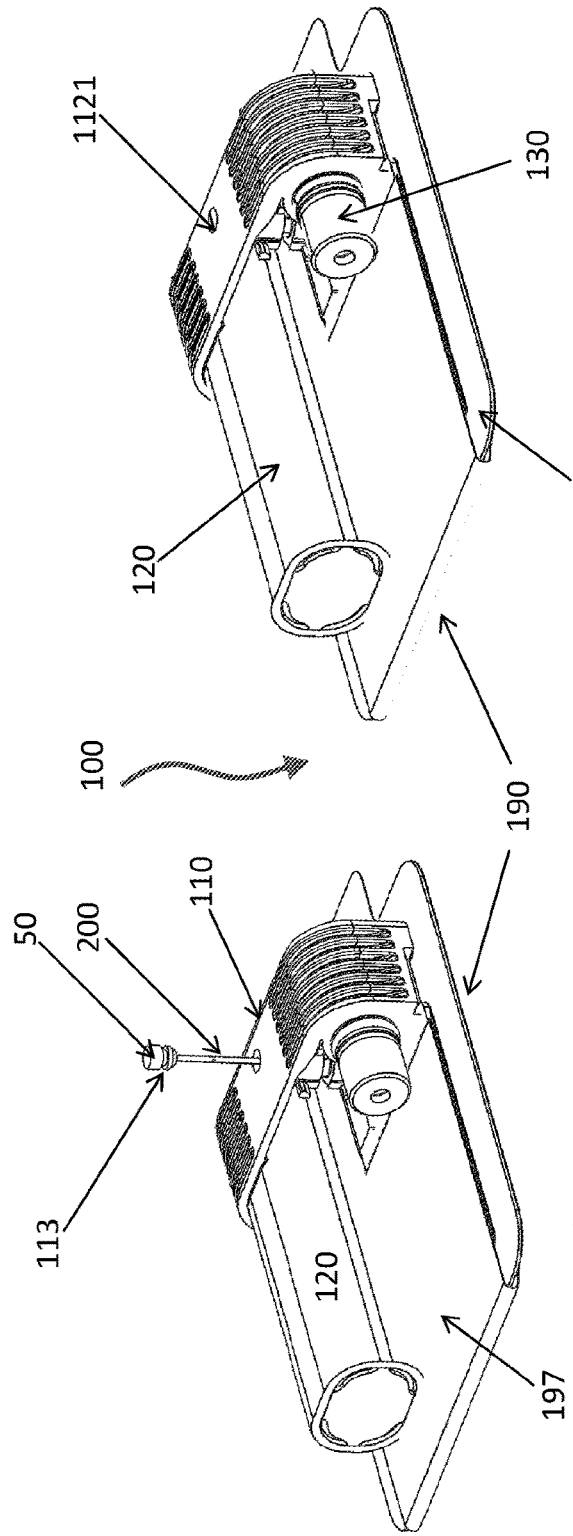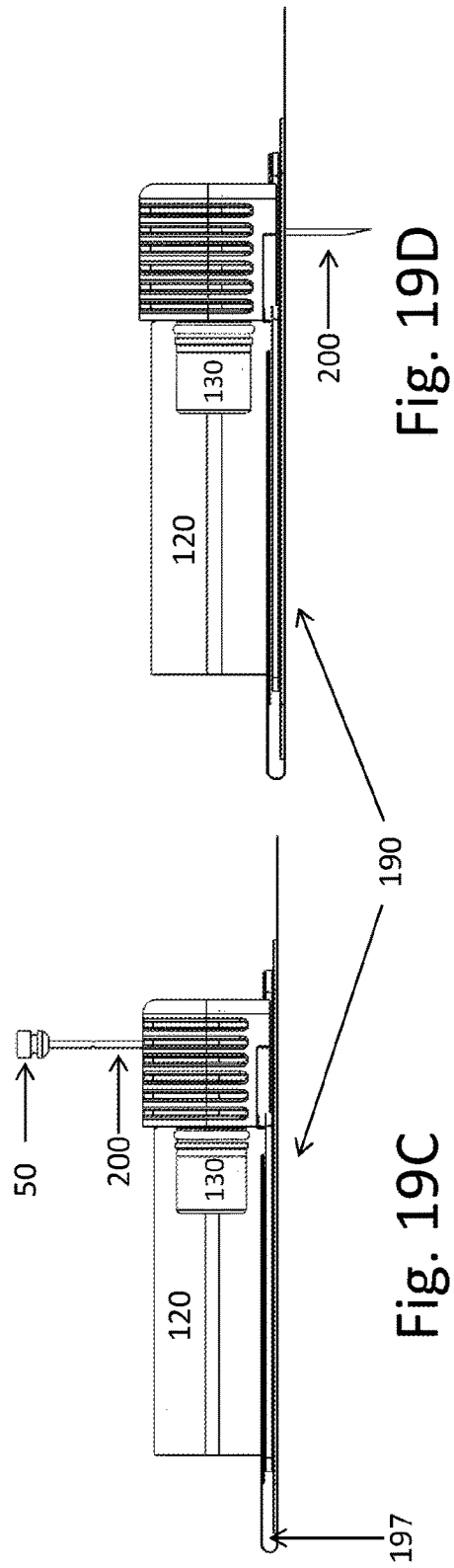

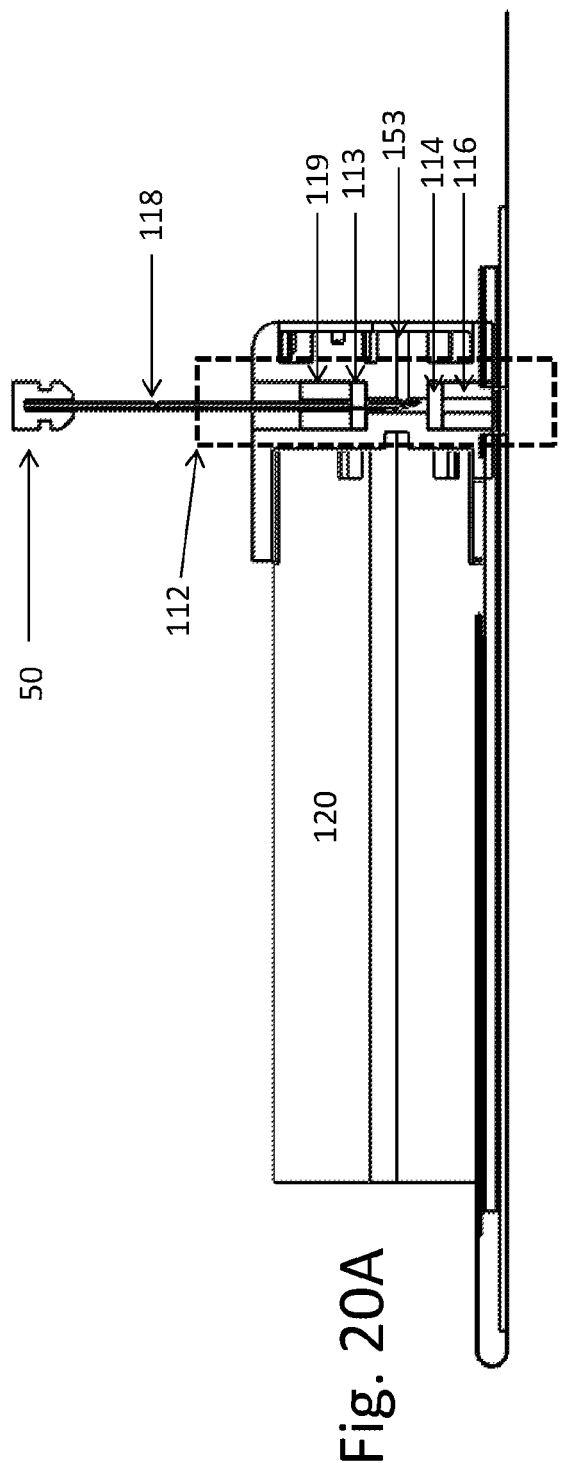
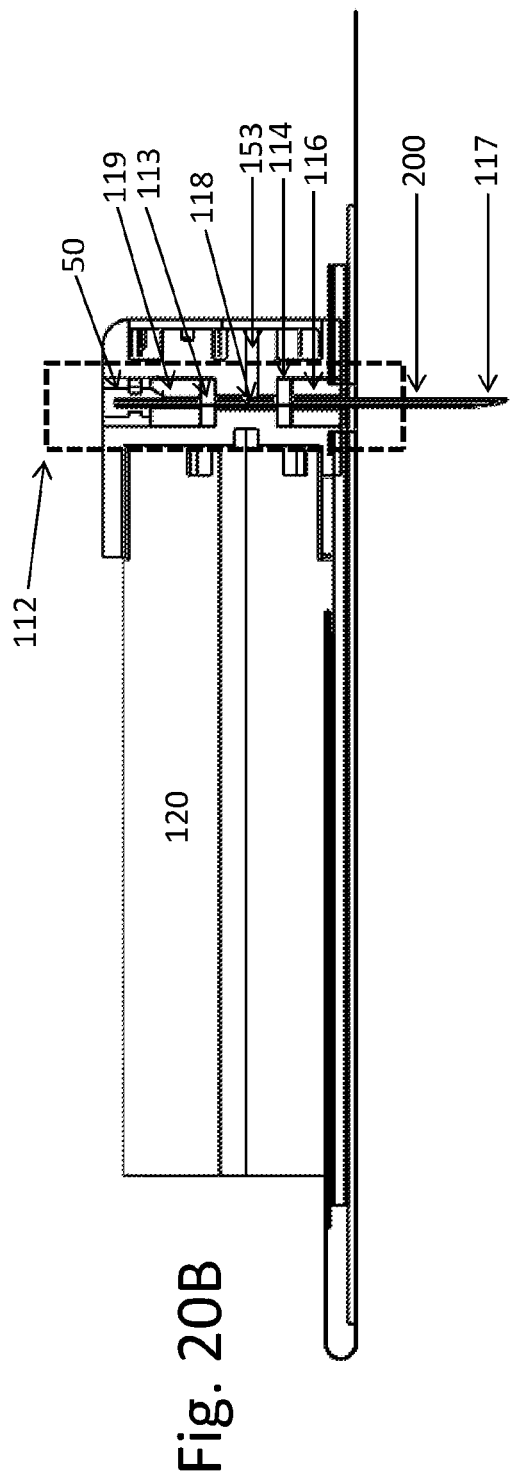

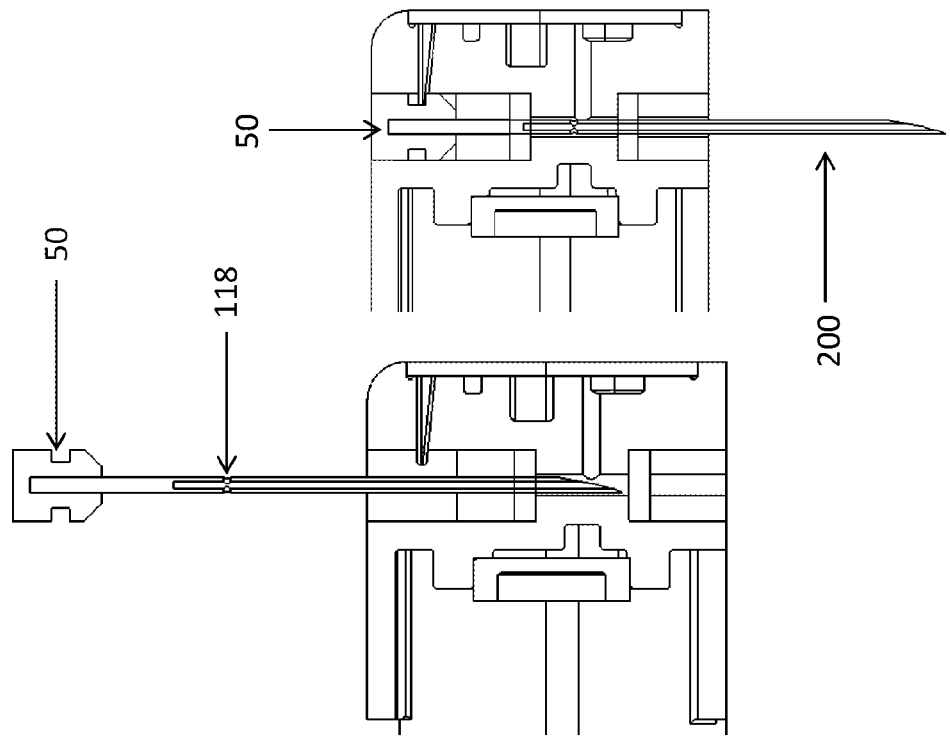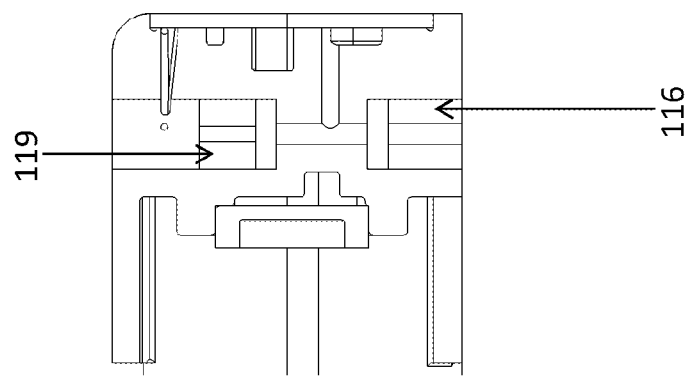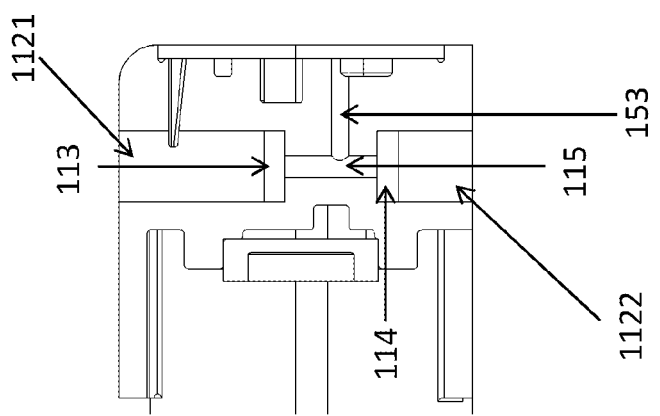

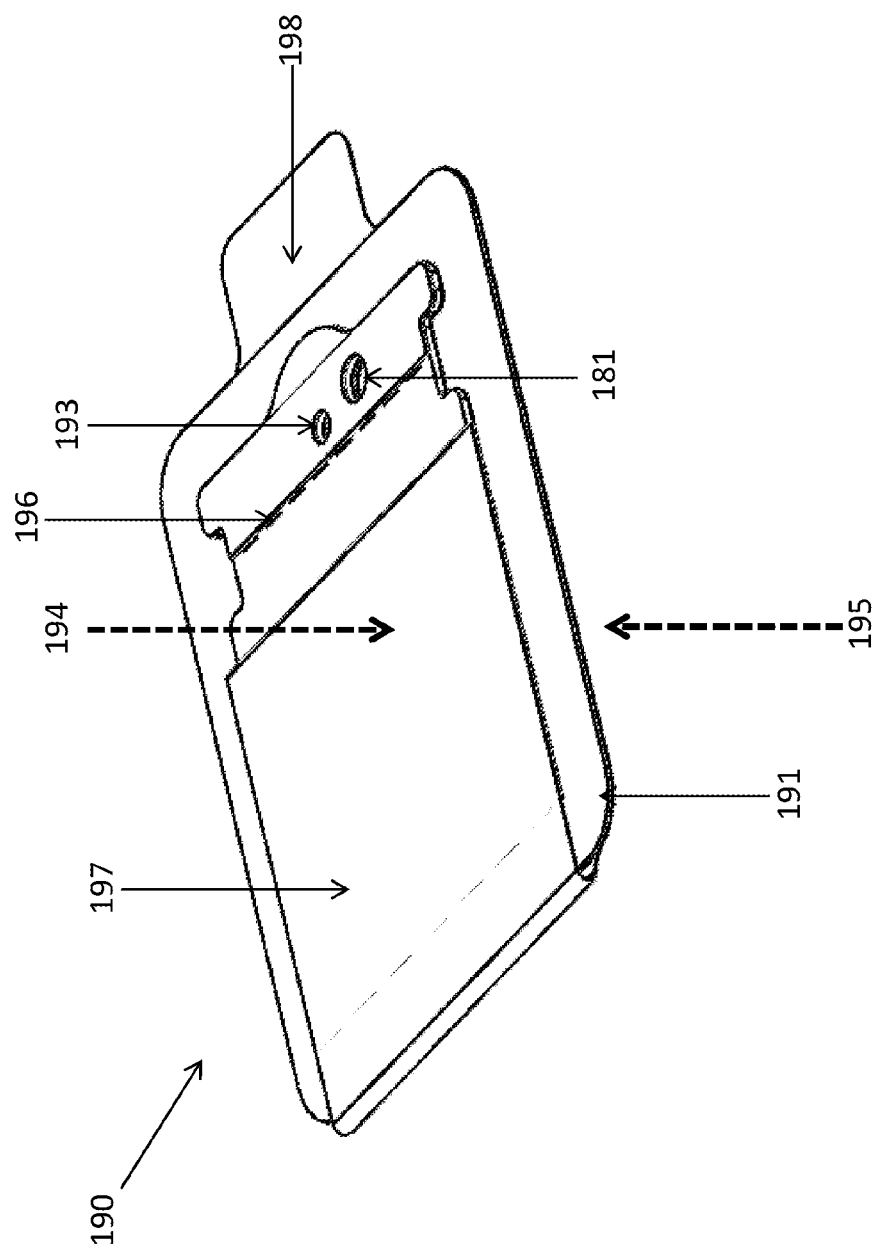

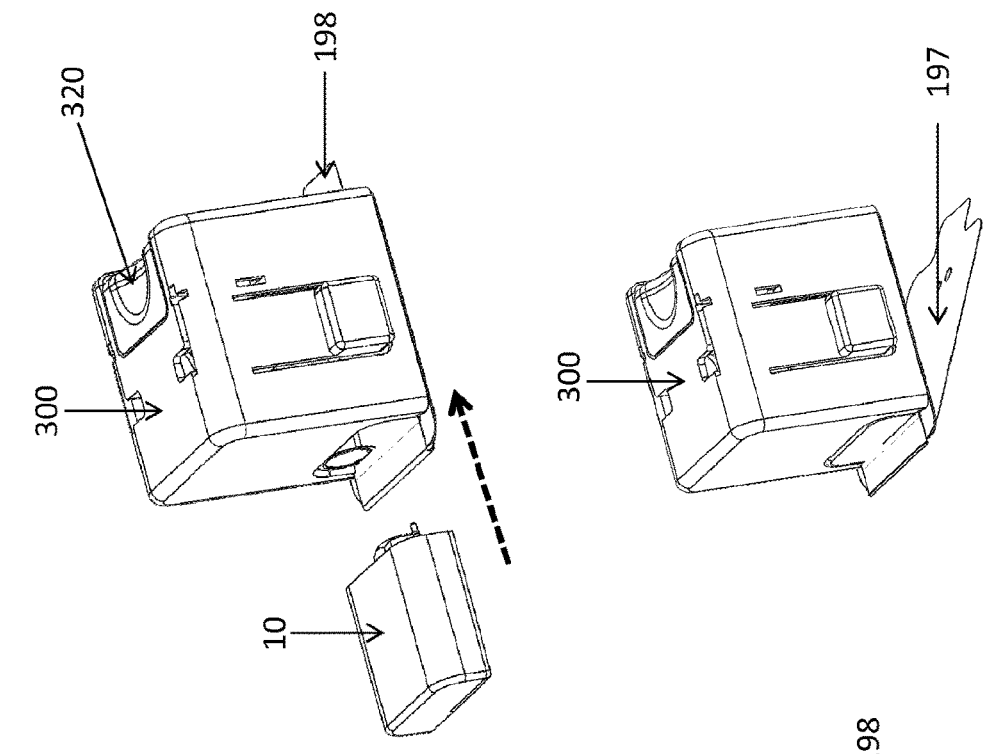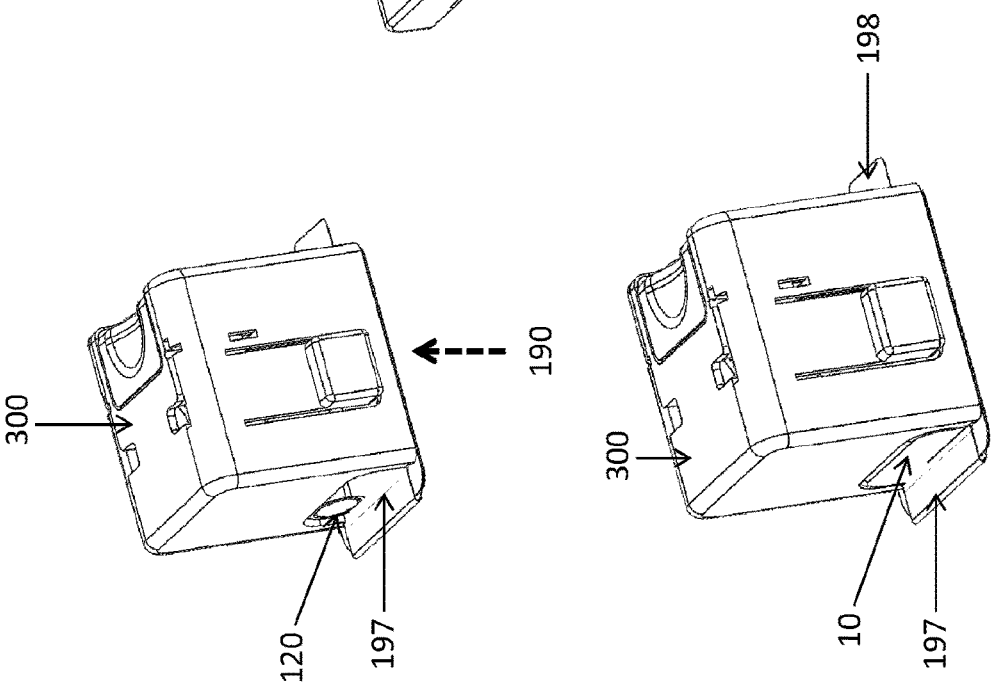

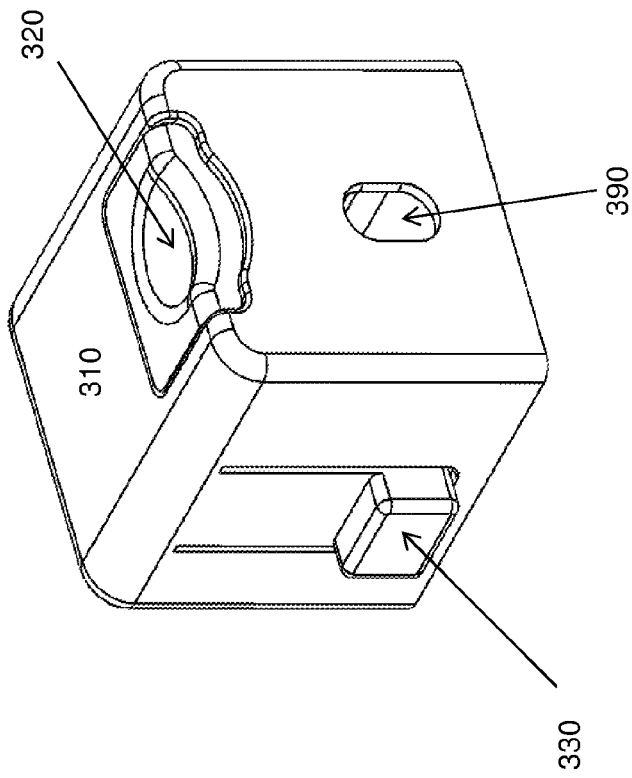
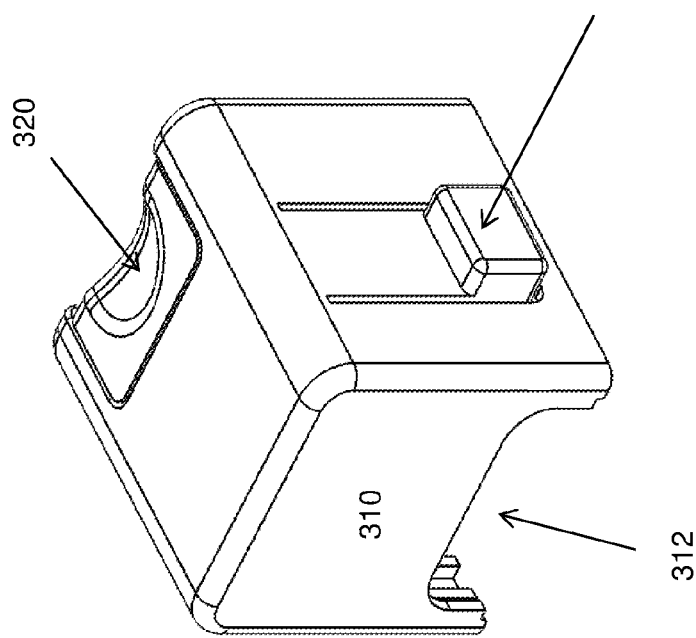

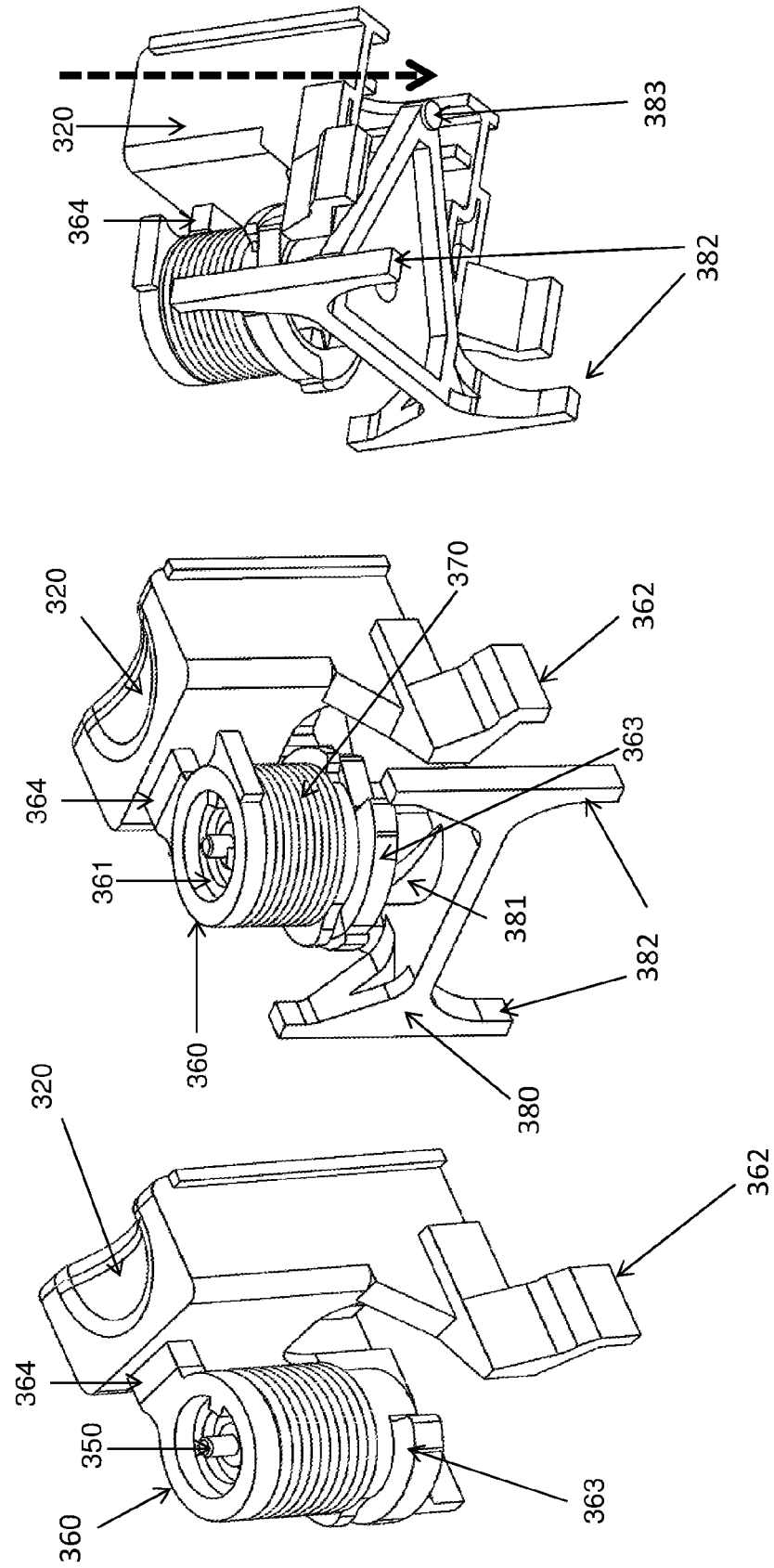

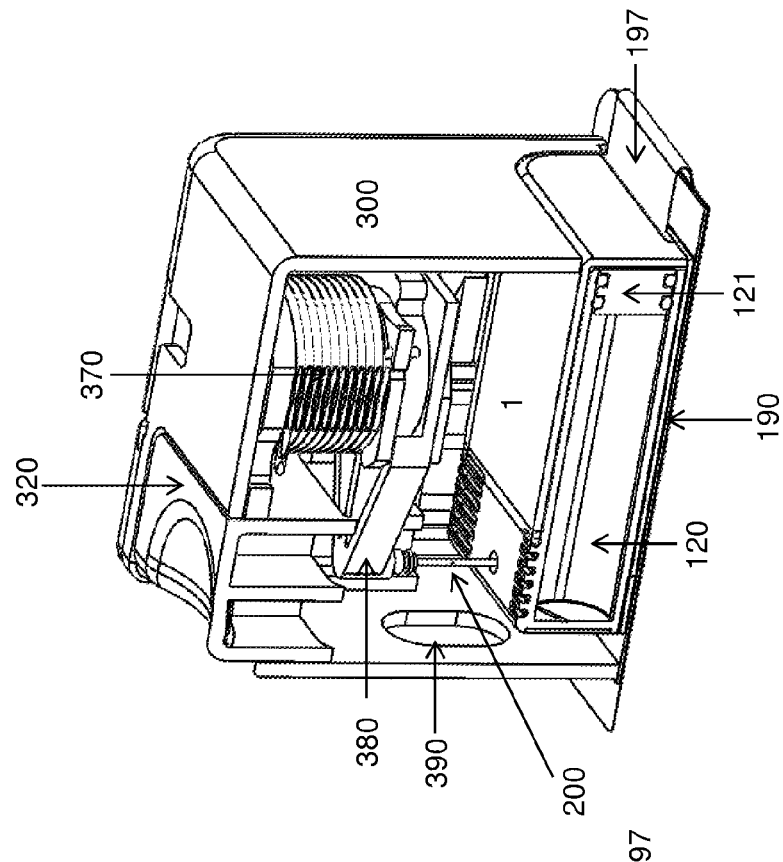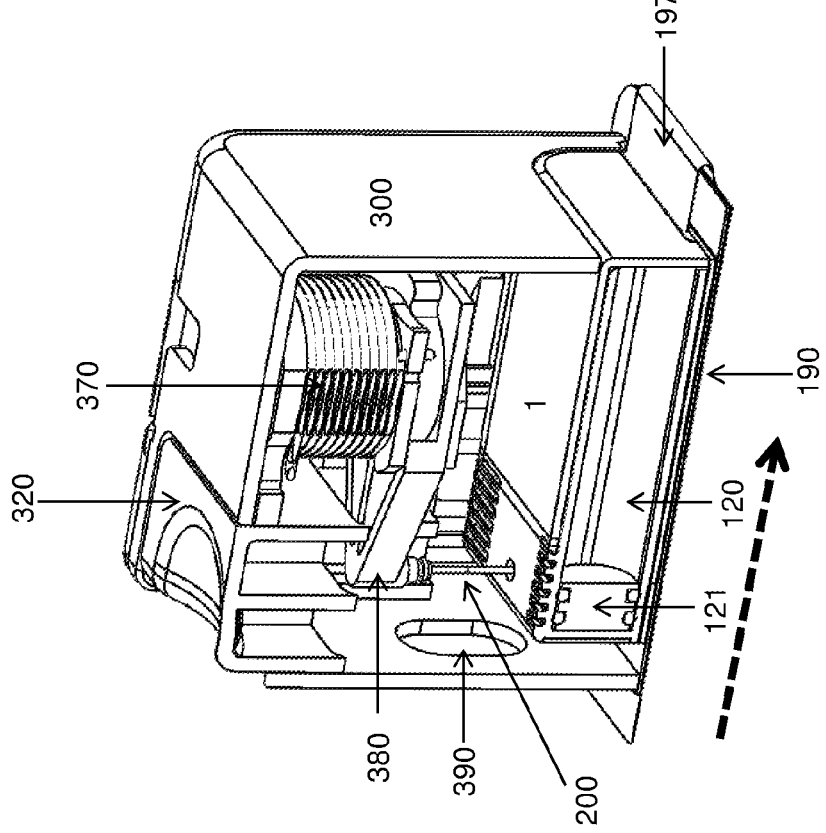

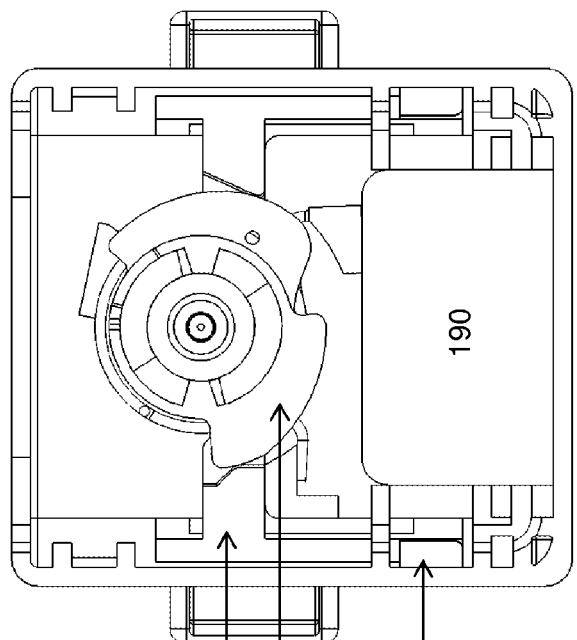
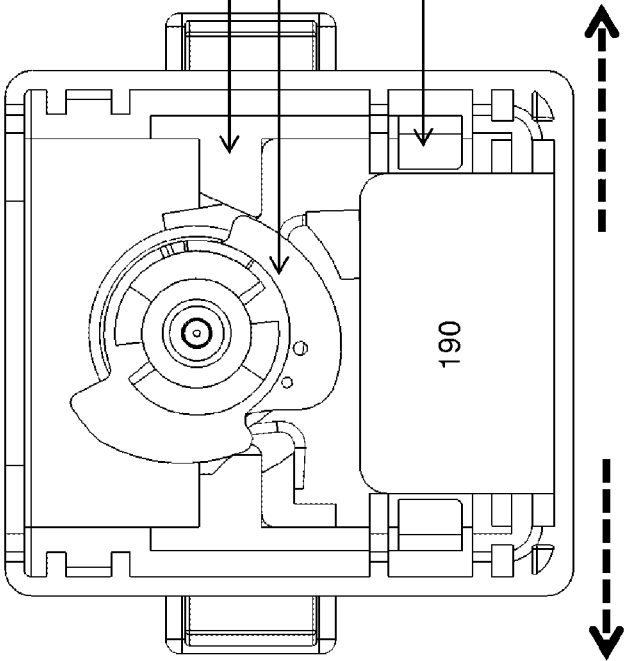

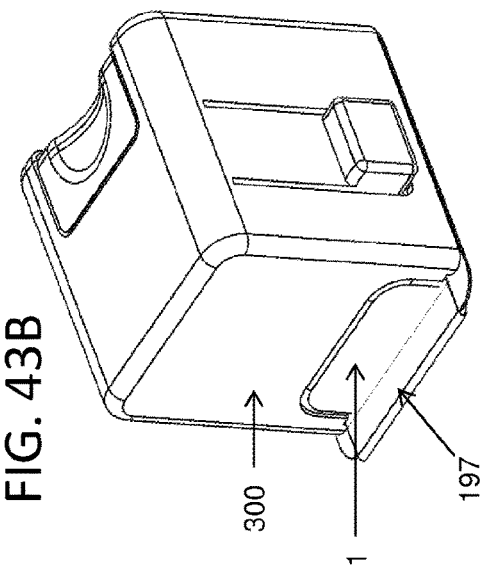
FIG. 43A
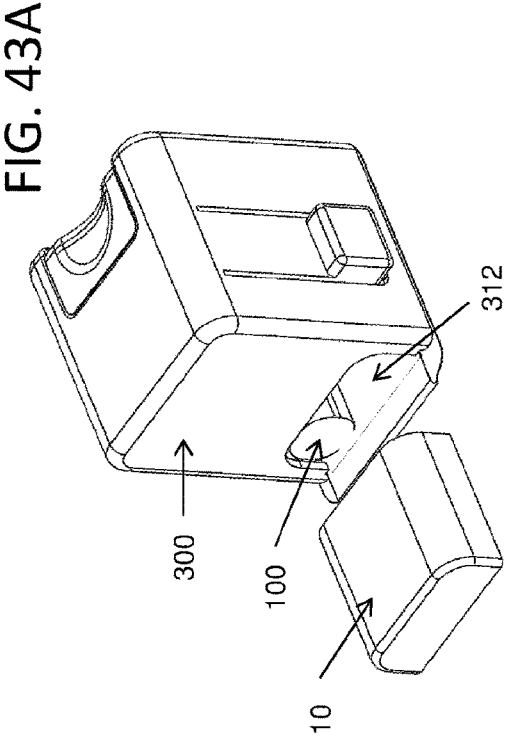
FIG. 43B
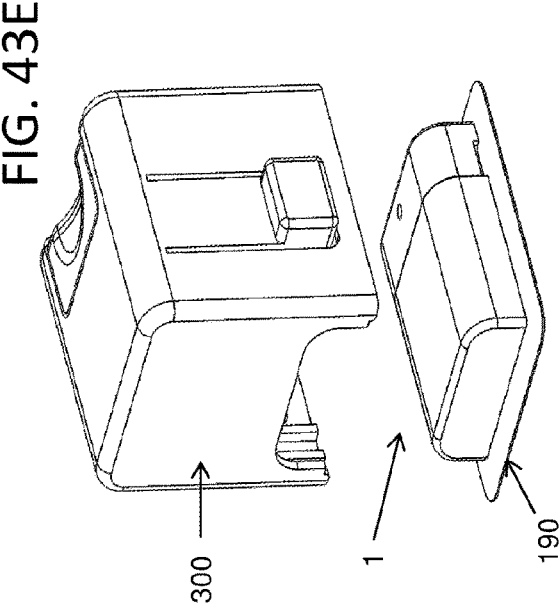
FIG. 43E
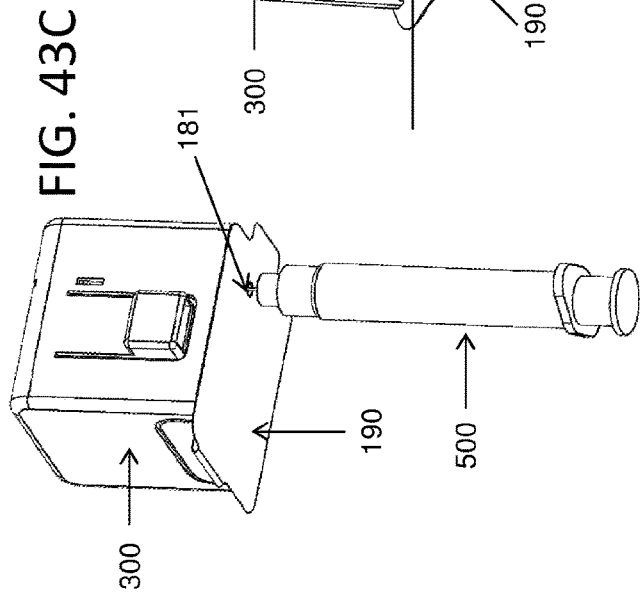
FIG. 43C
FIG. 43D

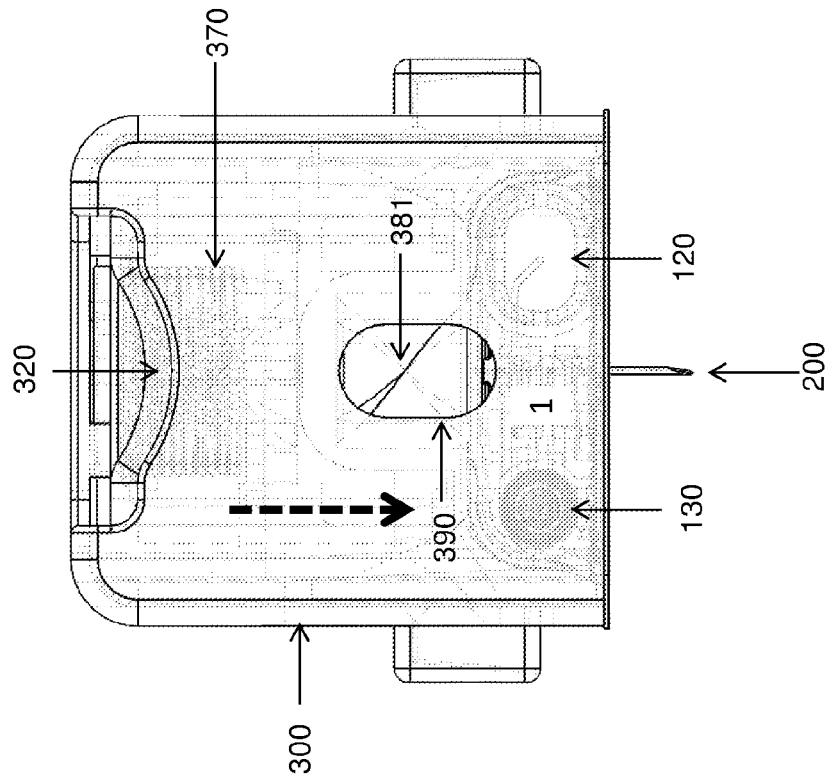
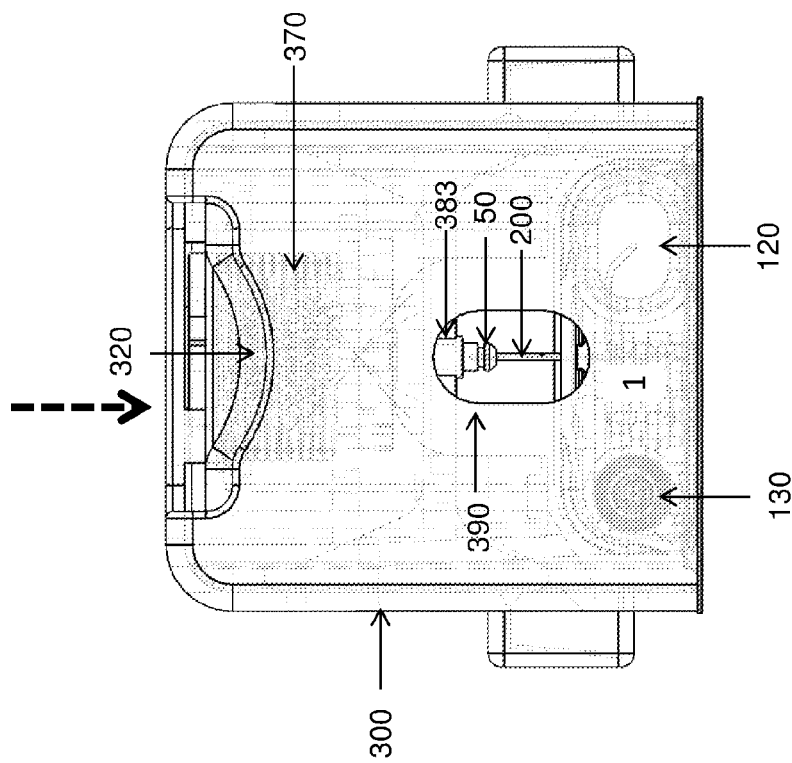
Fig. 45B
Fig. 45A

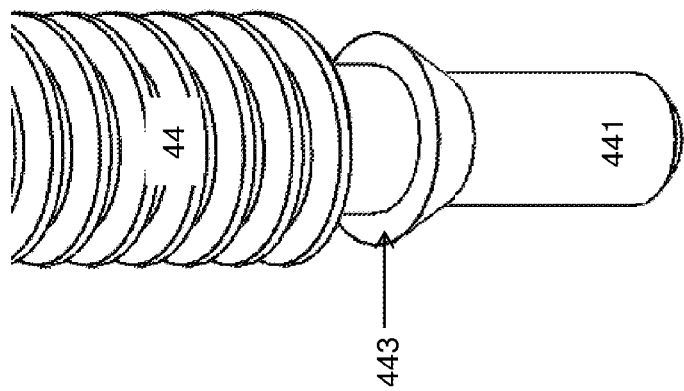
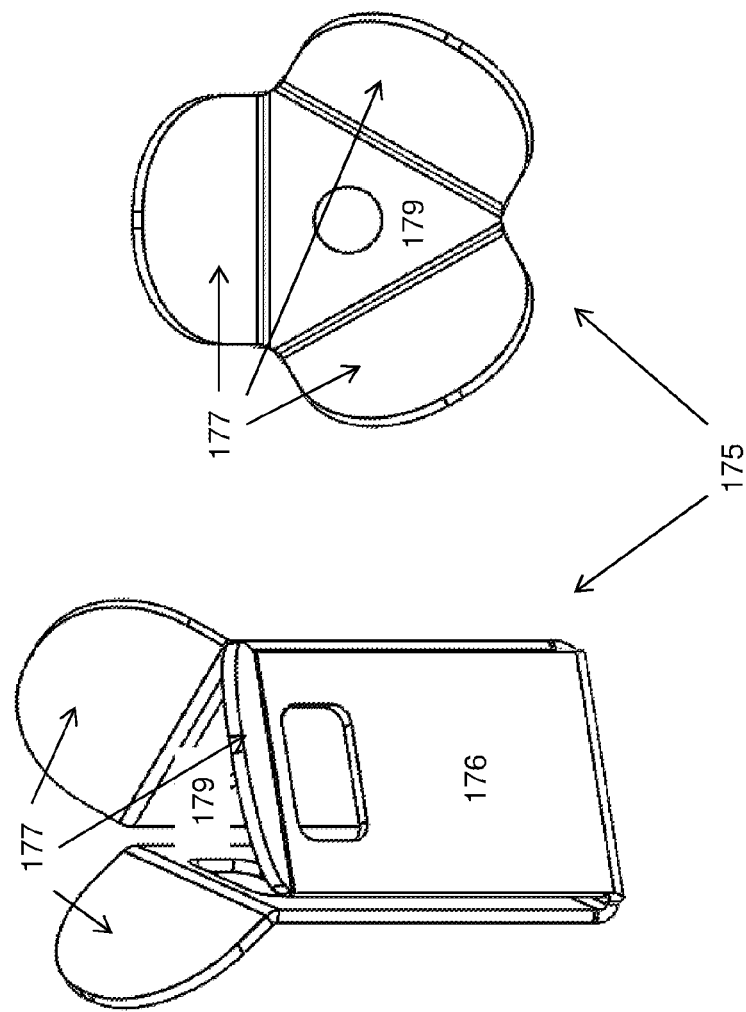
Fig. 47C
Fig. 47B
Fig. 47A

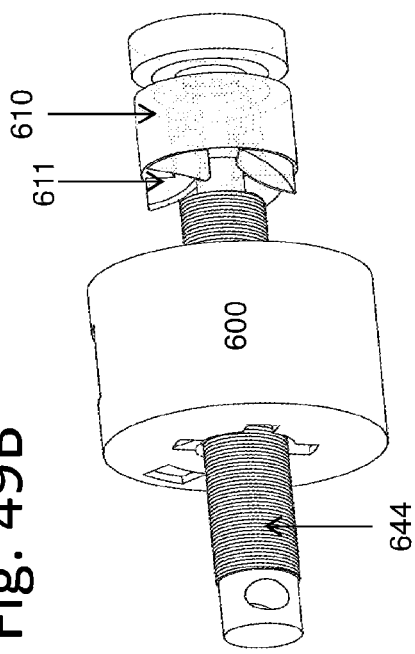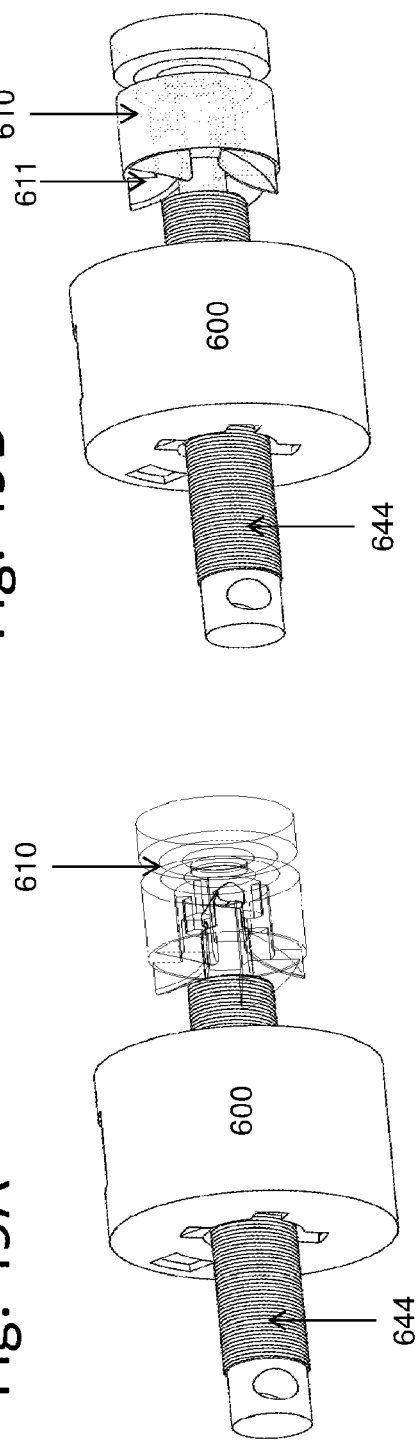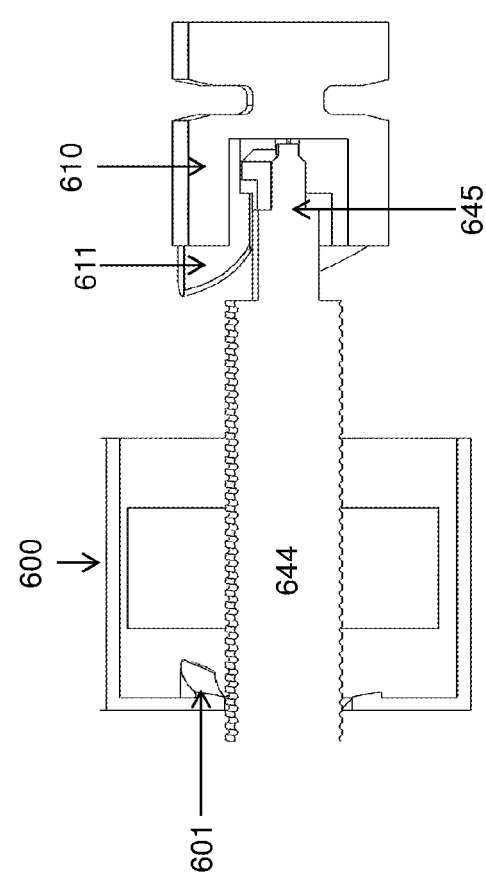
Fig. 49B
Fig. 49A
FIG. 49C

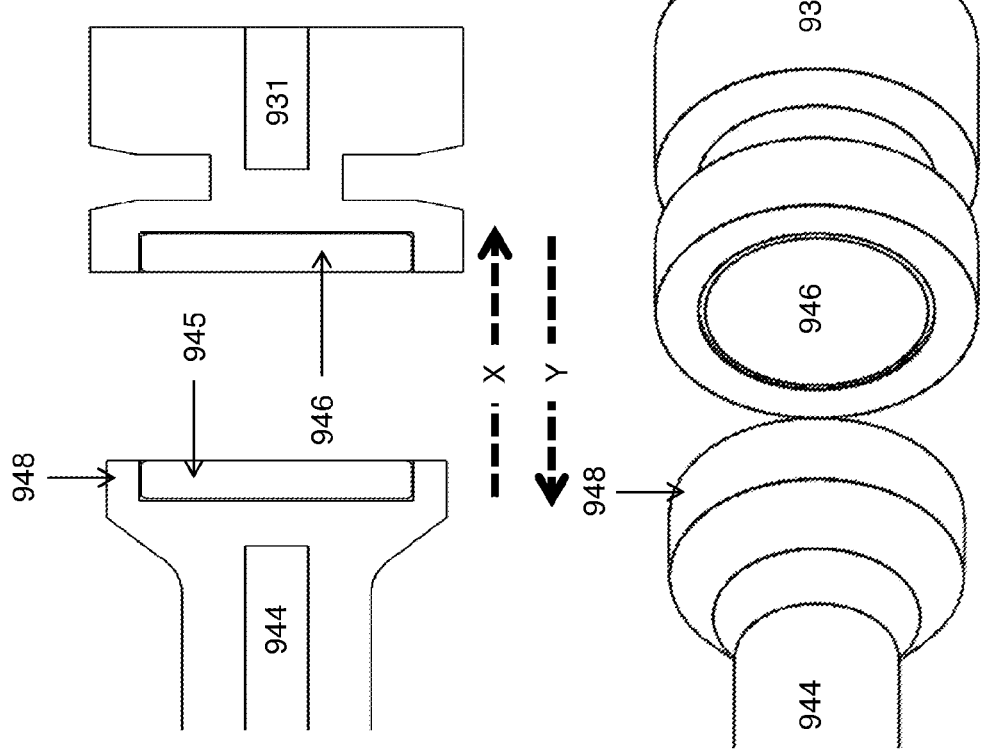

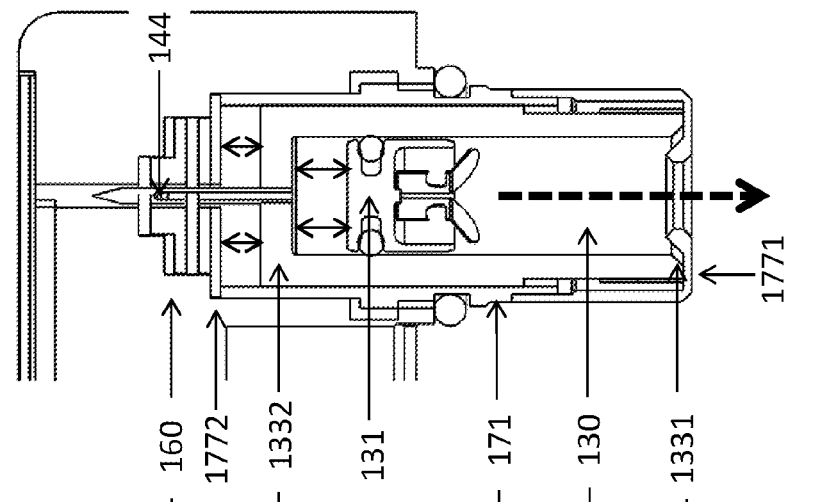
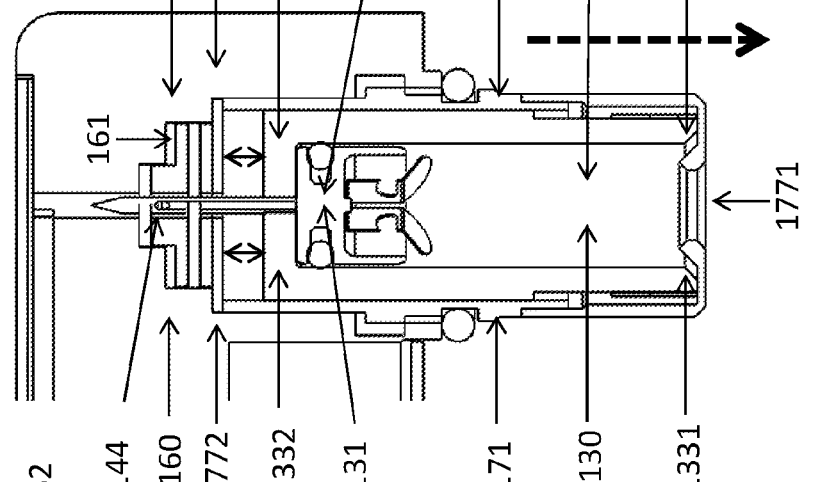
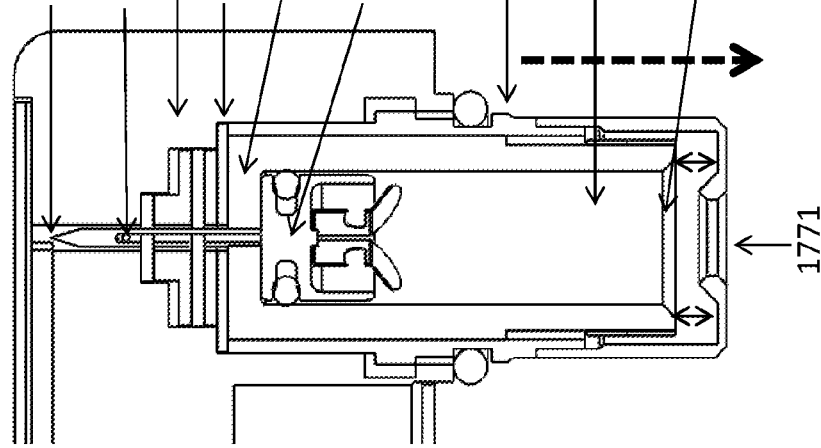

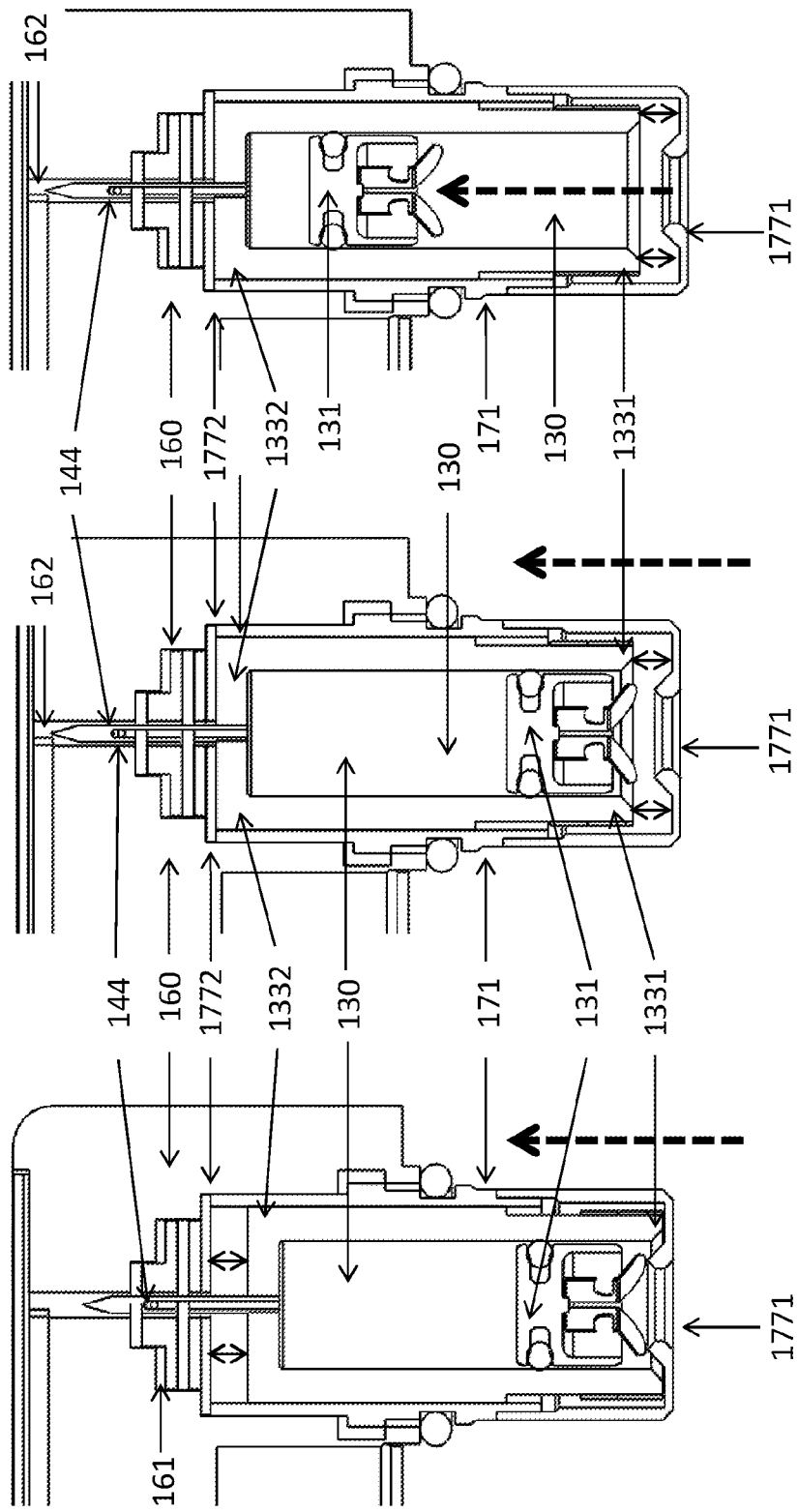

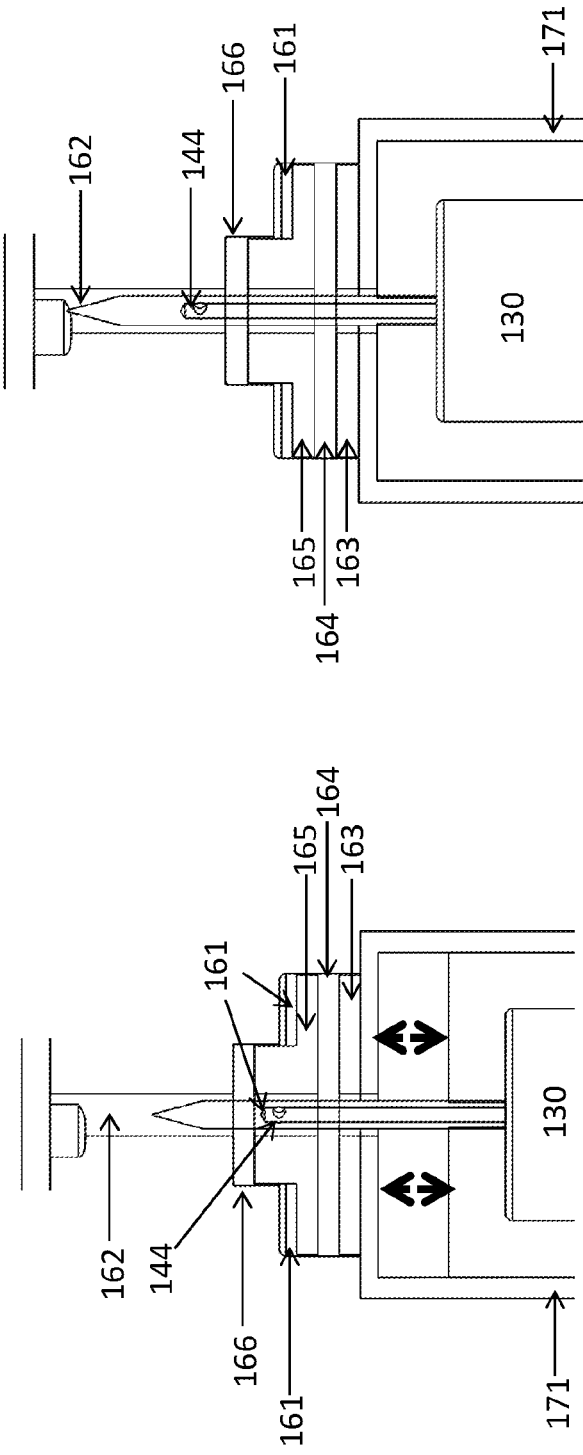

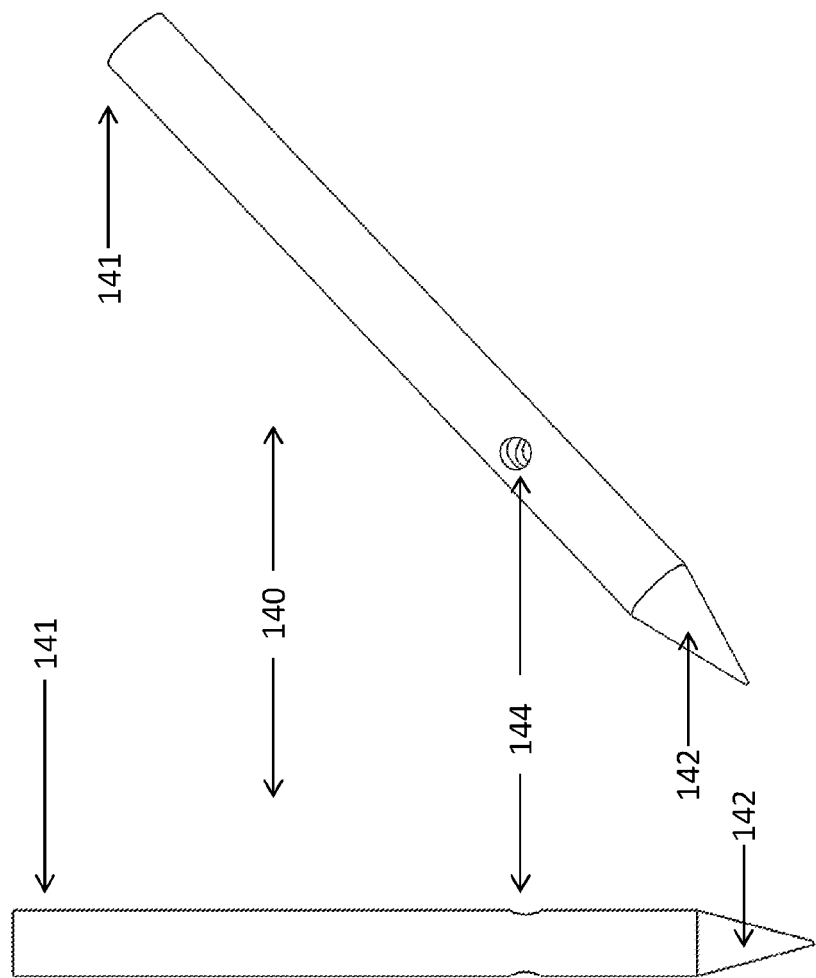

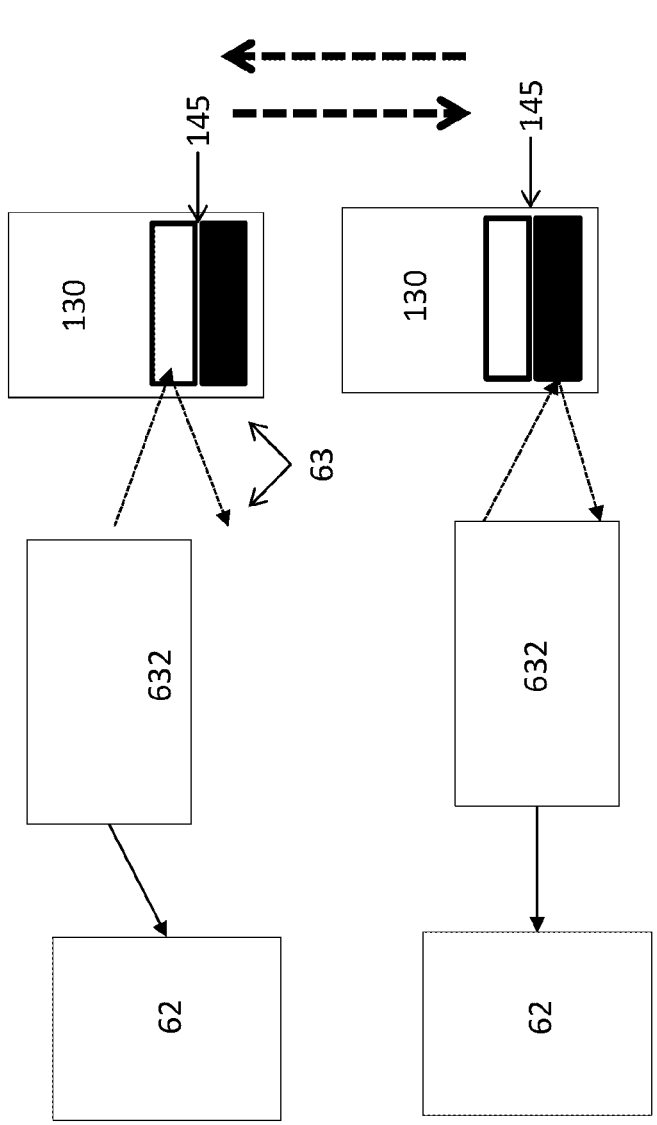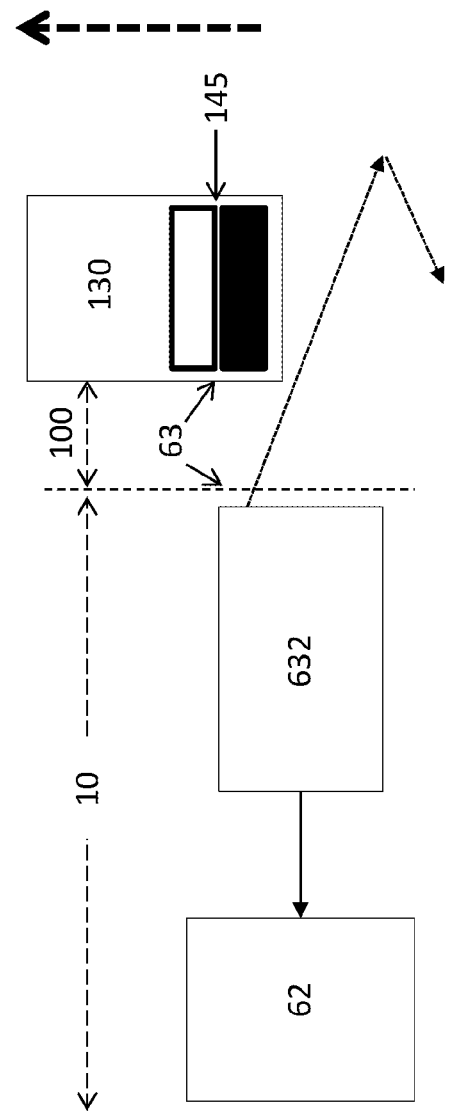

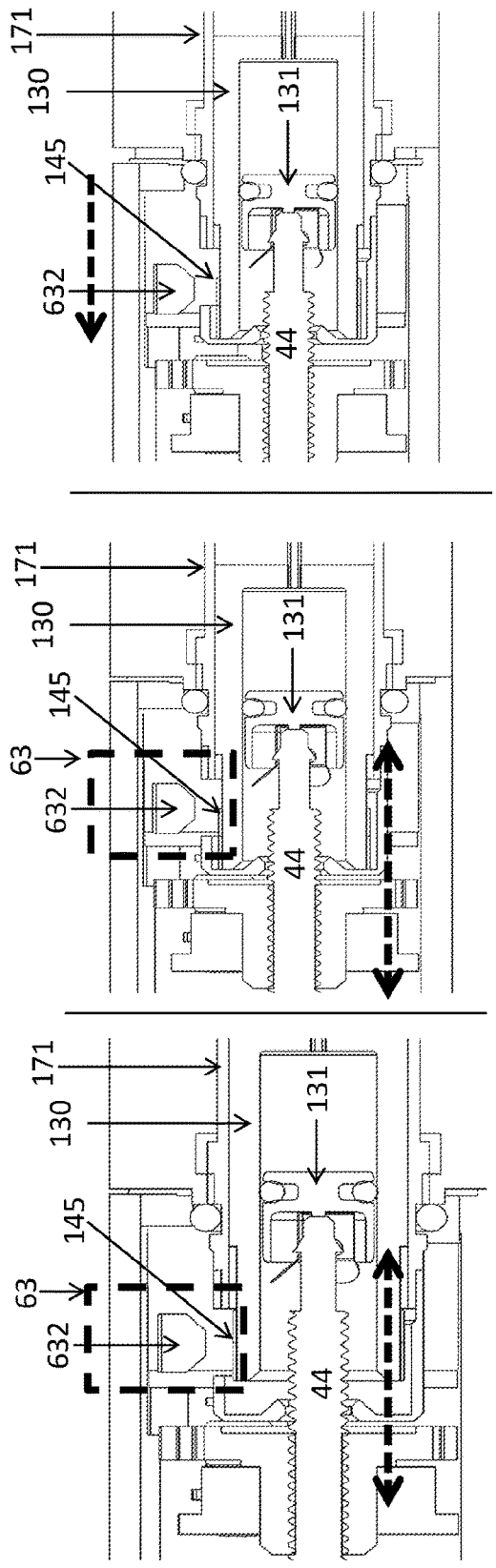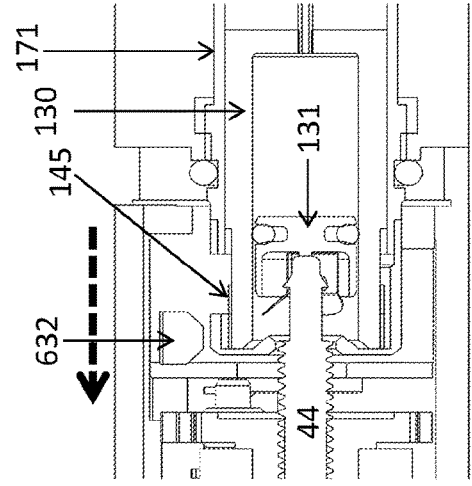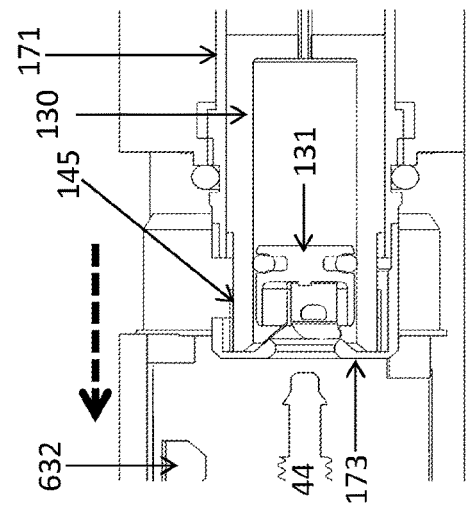

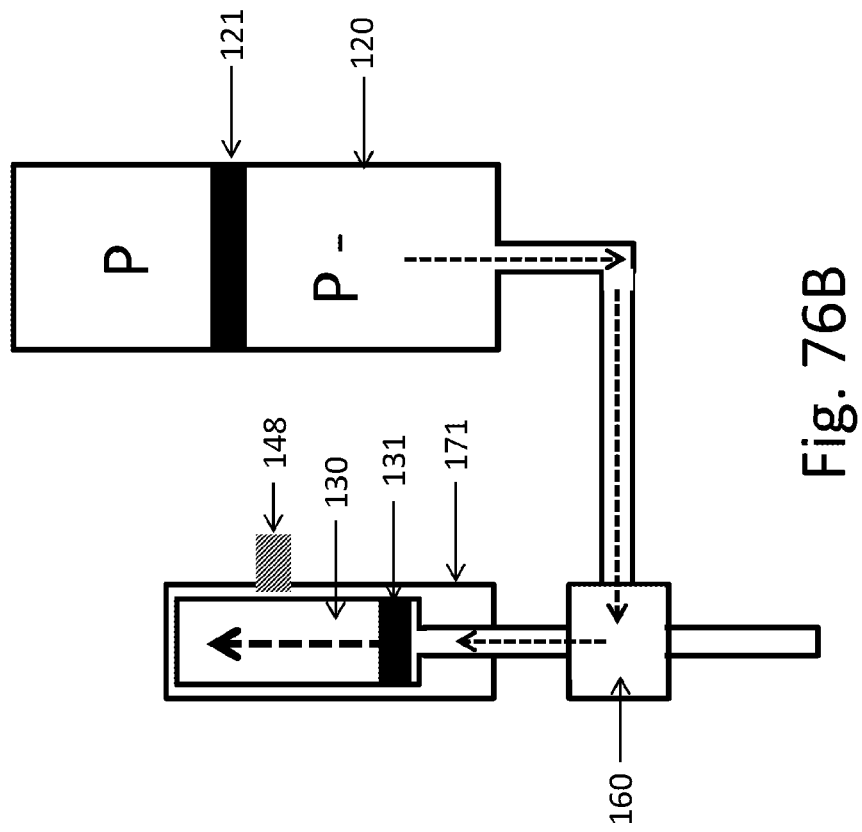
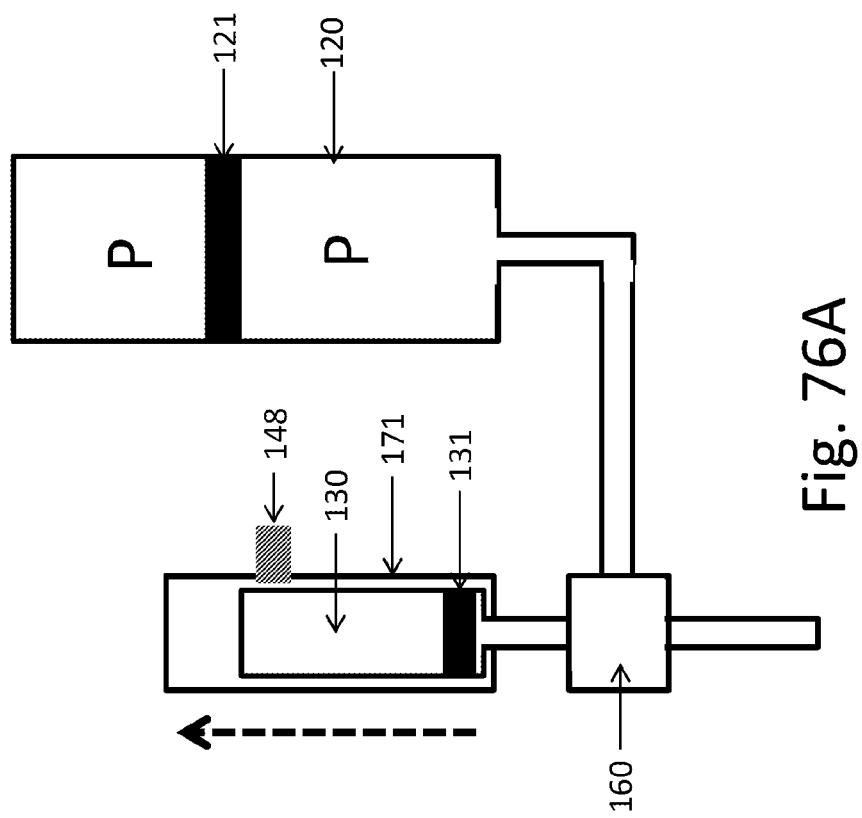
Fig. 76B
Fig. 76A

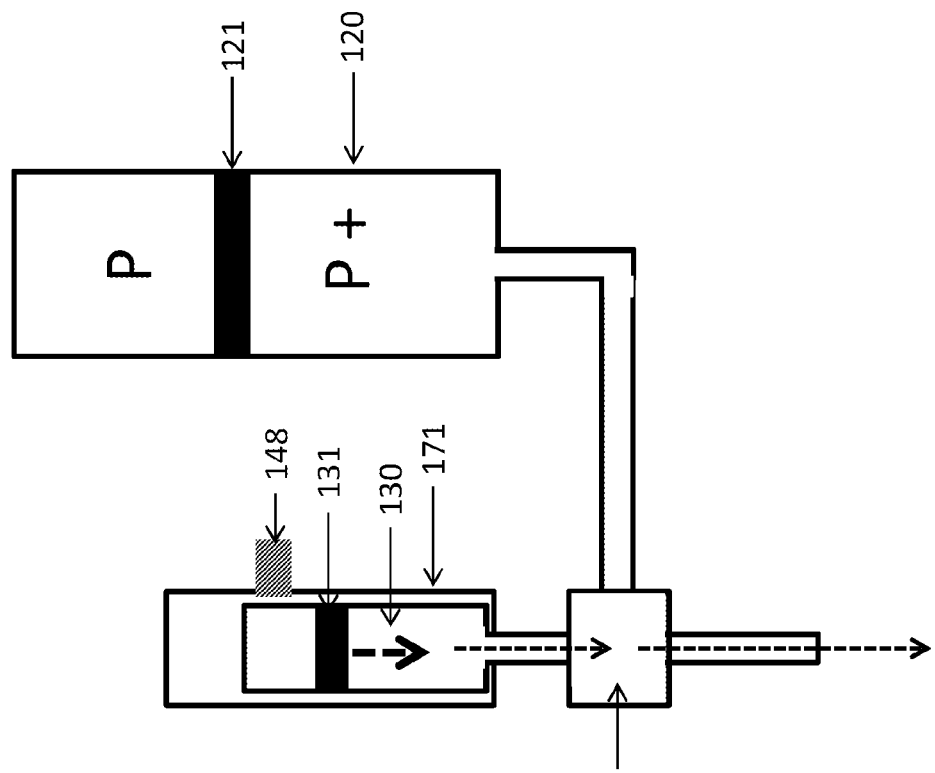
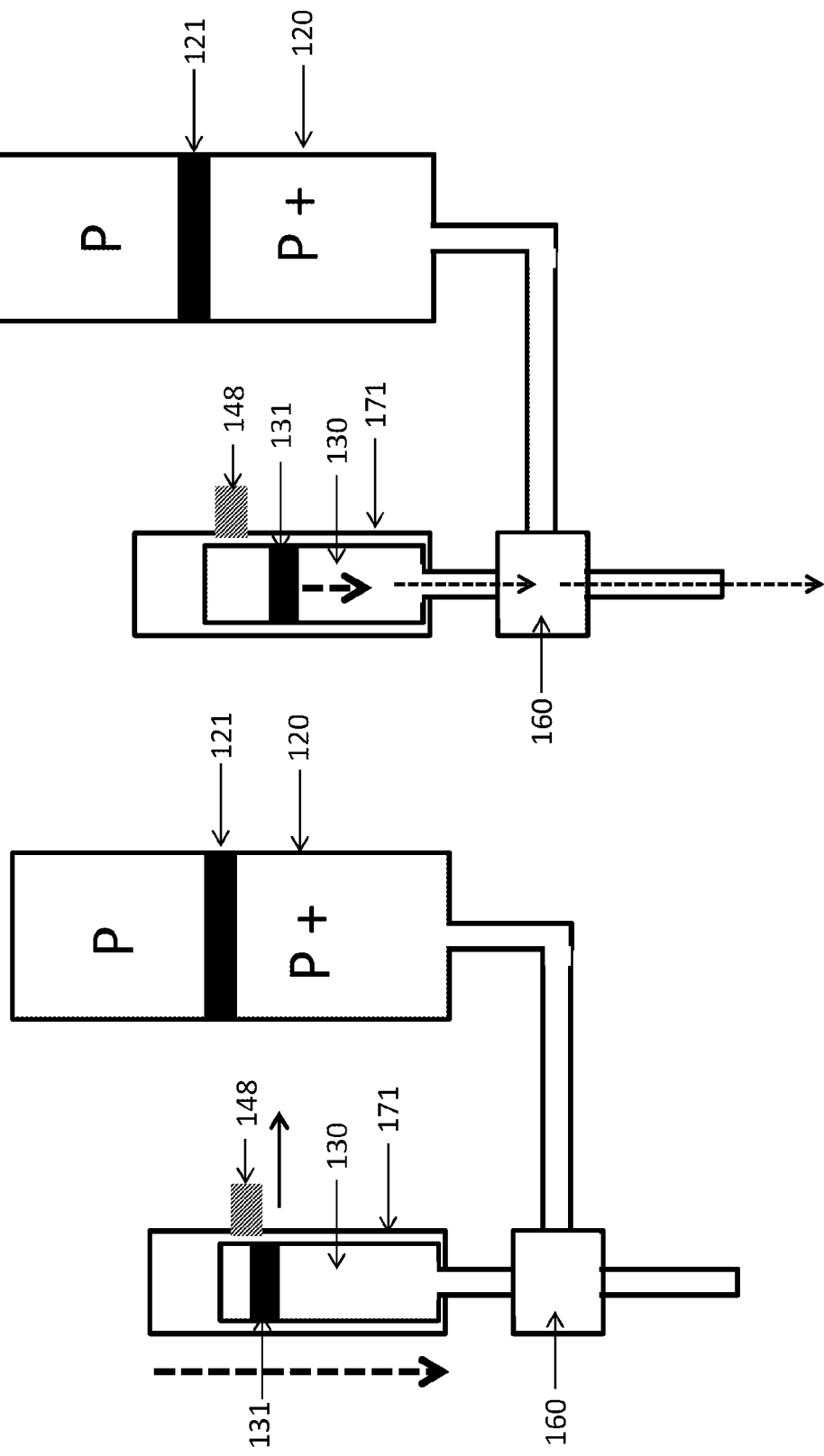
Fig. 78A
Fig. 78B

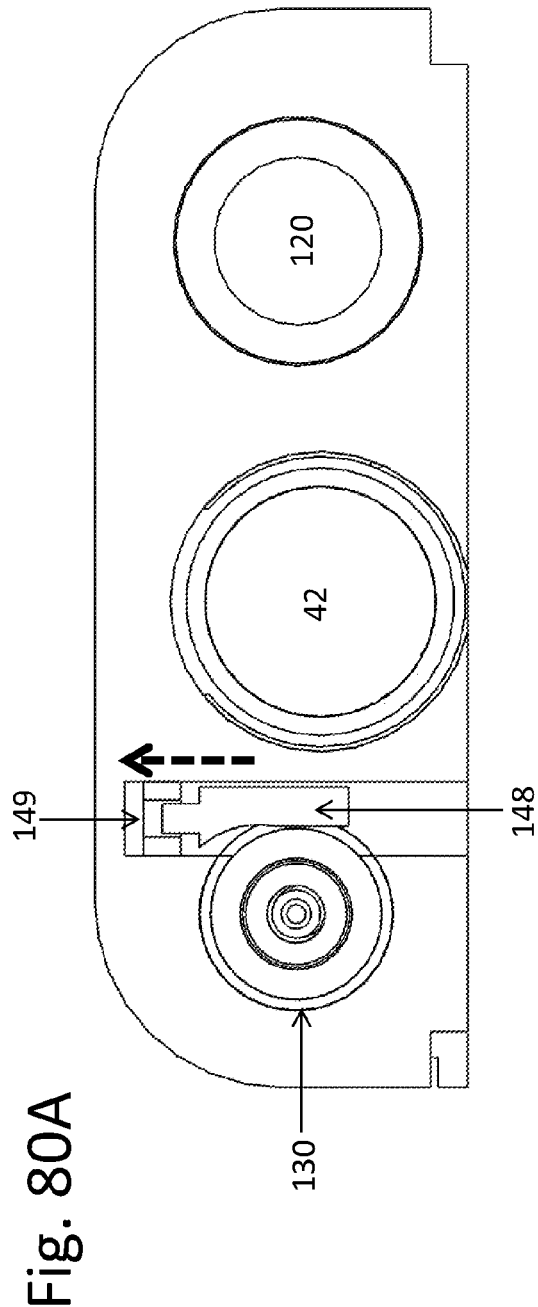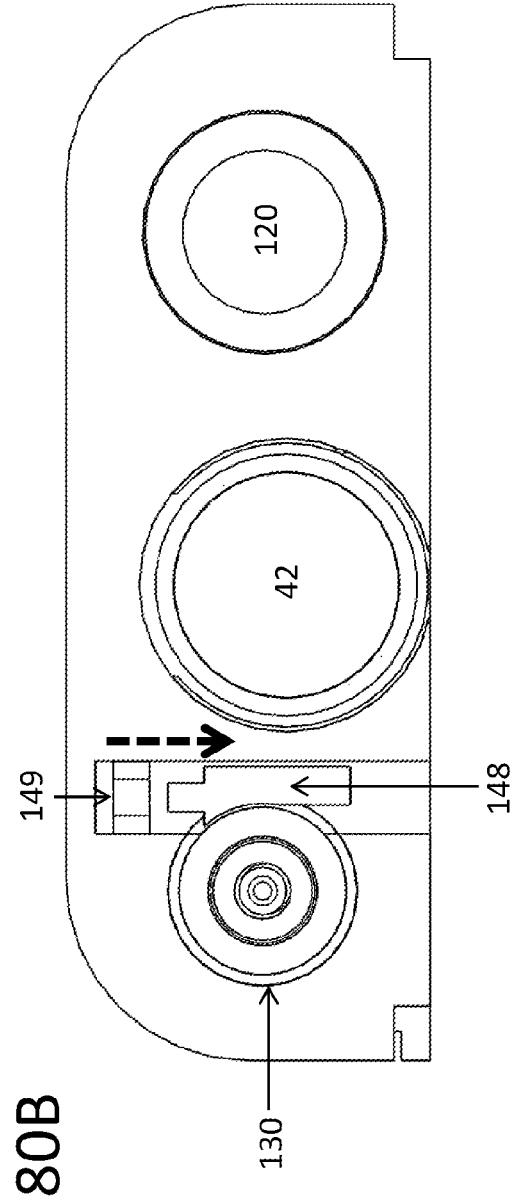

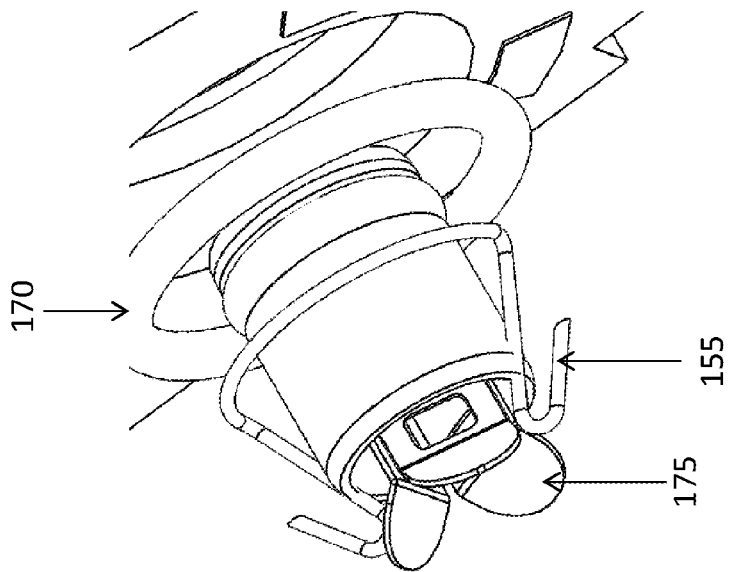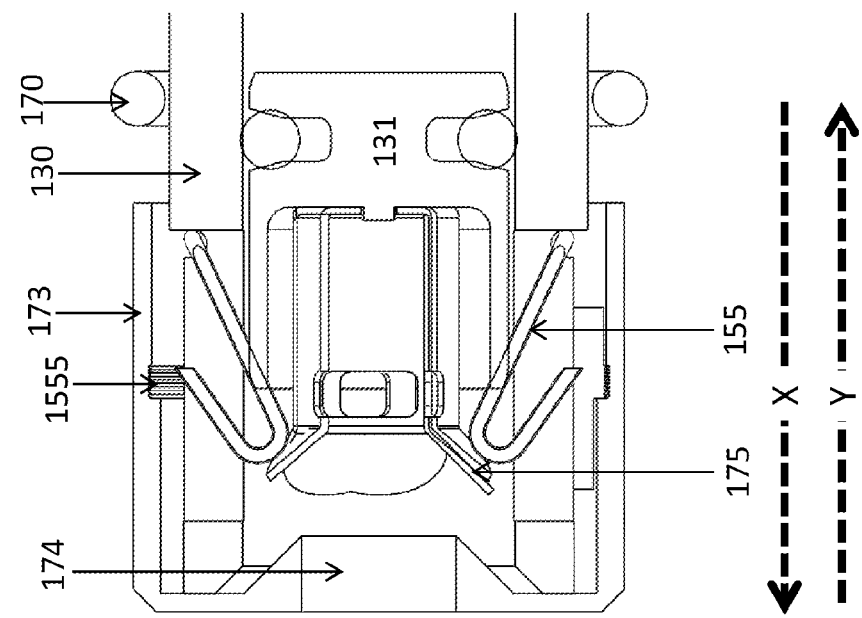

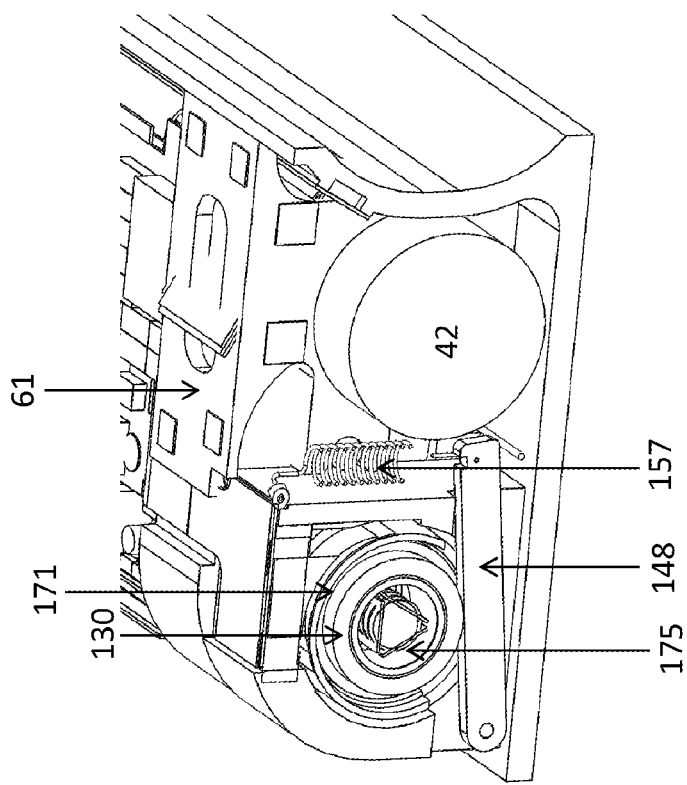
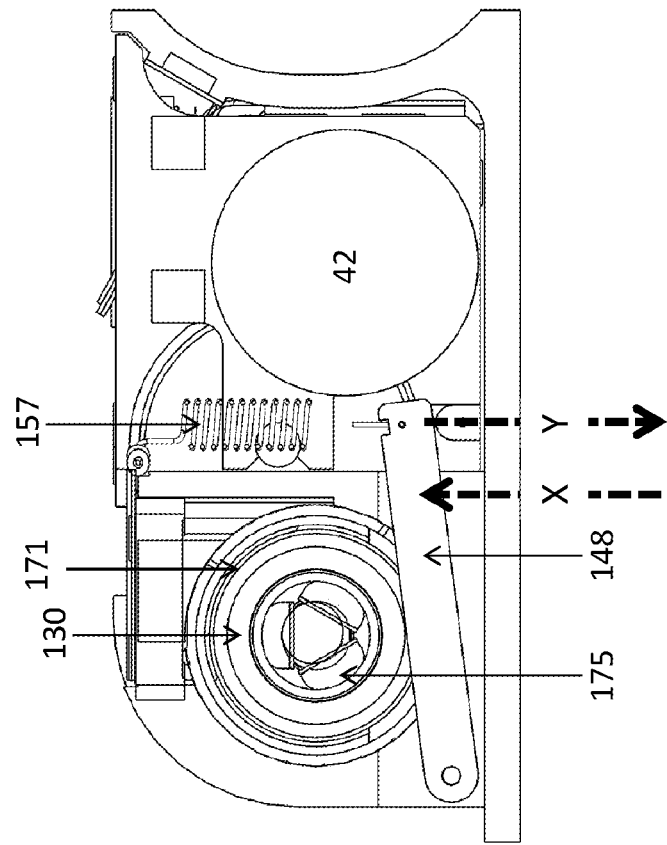

PATCH PUMP SYSTEMS AND APPARATUS FOR MANAGING DIABETES, AND METHODS THEREOF

RELATED APPLICATIONS

This application is a divisional of U.S. patent application Ser. No. 16/622,898, filed Dec. 13, 2019, entitled "Patch Pump System and Apparatus for Managing Diabetes, and Methods Thereof" which is a national stage entry of, and claims priority to International Application No. PCT/IL2018/050668, filed Jun. 15, 2018, entitled "Patch Pump System and Apparatus for Managing Diabetes, and Methods Thereof" as well as claims the benefit of and priority to U.S. provisional application No. 62/519,982, filed Jun. 15, 2017, entitled, "Patch Pump Systems and Apparatus for Managing Diabetes, and Methods Thereof". Each of these disclosures are herein incorporated by reference in their entireties.

FIELD OF THE DISCLOSURE

Embodiments of the current disclosure are directed toward systems, devices and methods for managing diabetes. More particularly, the present disclosure relates to a miniature, portable, skin-securable insulin patch pump for dispensing insulin to patients.

BACKGROUND OF THE INVENTION

Diabetes mellitus patients require administration of varying amounts of insulin throughout the day to control their blood glucose levels. Ambulatory portable insulin infusion pumps can be used as alternatives to multiple daily syringe injections of insulin, although such pumps can be bulky and complicated to handle.

SUMMARY OF SOME OF THE EMBODIMENTS

Embodiments of the present disclosure are directed at a diabetes management system that includes a miniature insulin patch pump. In some embodiments, skin securable, tubeless, insulin patch pumps may be desirable to "pager like" insulin pumps because they are less bulky and avoid tubing handling and complications. Despite pump miniaturization, however, it may be desirable for patch pumps to meet technical specifications and user's interface requirements that are at least similar to those of pager pumps. Although discussions of several embodiments in the current disclosure refer to insulin as the drug being delivered by the patch pump disclosed herein, it is to be understood that the use of the disclosed patch pump to other fluids is deemed to be within the scope of the inventive embodiments described herein.

In some embodiments, the patch pump may be controlled by a handheld controller having a wired or wireless communication means, an example of the latter including RF communication means such as but not limited to Bluetooth or Bluetooth Low Energy (BLE). The patch pump may be integrated in a diabetes management system that includes a continuous glucose monitor (CGM) and a blood glucose monitor (BGM). An artificial pancreas algorithm on the patch pump processor can control (e.g., automatically, when prompted, etc.) insulin delivery according to continuous or intermittent glucose readings received from a remote CGM ("closed loop system"). The patch pump may regularly (e.g., continuously) deliver insulin, receive glucose readings from a CGM and accordingly administer insulin, and receive bolus commands from the controller at meals. The controller may communicate with a smartphone and/or with one or more servers (e.g., in one-way or two-way communication lines to the cloud) such that data from the diabetes management system may be transmitted on line to remote locations. As an example, a controller of a patch pump worn by a child patient may transmit various data gathered and/or received by the patch pump to a smartphone of a parent and/or to one or more computer servers of the health care providers of the child.

In some embodiments, the patch pump may include one or more of: 1) a reusable part (RP) that may comprise a housing ("RP housing"), a connecting magnet/iron plate, one or more power sources such as batteries, a buzzer, a driving mechanism that includes a motor, a gear, and a lead screw, in some instances at least a part of the pumping mechanism, and an electronic module that includes a PCB, a microprocessor, and sensors; 2) a disposable part (DP) that may comprise a housing ("DP housing"), a connecting magnet/iron plate, an adhesives base, in some instances at least a part of pumping mechanism that may include a cannula, a first reservoir and a second reservoir ("doser"), a first plunger and a second plunger, a doser actuator, conductive conduits, a dual chamber valve mechanism, an inlet port, and an exit port ("well"); 3) a preloaded, disposable inserter assembly (which may also be referred to herein as a patch-pump assisting system, the phrases may be used interchangeably throughout) that may comprise a housing, a trigger, safety catches, a cannula insertion mechanism, a releasing mechanism, and a viewing window and 4) a charger.

In some embodiments, the RP comprises at least two compartments, a vented compartment in air communication with the atmosphere and a sealed compartment. The vented compartment comprises a cavity that is occupied by the first reservoir after RP-DP connection. The sealed compartment includes the driving mechanism, the electronic module, and a cavity that occupies the first reservoir (doser) after RP-DP connection. The driving mechanism includes a motor (e.g., stepper motor or DC motor), a gear, and a lead screw. A lead screw pin perpendicularly transverses an opening at the tail of the lead screw and can freely slide within grooves at the RP housing. During motor and gear operation (and rotation), the lead screw pin can prevent rotation of the lead screw and consequently, the lead screw is linearly displaced in one direction. Reversing the direction of rotation of the motor and the gear causes linear displacement of the lead screw in an opposite direction.

In some embodiments, the DP includes the pumping mechanism, and all or substantially all parts that are in contact with the delivered fluid (e.g., drug such as but not limited to insulin) including reservoirs, dual chamber valve mechanism, conduits, filling port, and exit ports. The dual chamber valve mechanism ("valve mechanism") may include an inlet chamber and an exhaust chamber. The main conduits are the first conduit that communicates between the first reservoir and the inlet chamber, and the second conduit that communicates between the exhaust chamber and the exit port. In some embodiments, the DP is provided with a sleeve—a cylinder that is rigidly connected to the DP housing and occupies the doser such that the doser can be freely, linearly displaced, within the sleeve. The sleeve is connected to a sleeve cover that holds the doser within the sleeve cavity. At least one gasket (e.g., RP-DP O-ring) in contiguity with the sleeve may provide sealing of the RP sealed compartment after RP-DP connection.

In some embodiments, the DP is provided with an adhesive base. The adhesive base comprises a flexed base that has sticky adhesive upper and bottom surfaces, a filling aperture (filling port) that is covered with a self-sealed rubber septum (filling septum), and a cannula aperture. Both sticky surfaces are covered before operation (e.g., before RP-DP connection takes place) with a folded removable liner. After RP-DP connection, the liner is removed, the upper sticky surface is adhering to the RP housing, and the bottom sticky surface is adhering to the patient's skin. A firm and reversible connection of RP and DP can be provided with concomitant forces of the connecting magnet and the upper sticky surface of the adhesives base. The connecting magnet and the iron plate can be interchangeably situated on the RP and/or DP.

In some embodiments, the DP is provided with a cannula that is inserted into the patient body after adhering the patch pump to the skin. The cannula can be rigid or at least substantially rigid (e.g., steel cannula) having a sharp tip at the distal end, a cap at the proximal end (cannula cap), and an opening at the cannula mid portion (cannula opening). The cannula can be linearly displaced within a groove in the DP housing (DP groove) that transverses the DP housing. The DP groove has an upper end, a lower end, and a mid-portion that has a cavity (well). The distal end of DP groove is in communication with the adhesives base cannula aperture and is sealed with a bottom seal and a bottom spacer. Before insertion, the cannula upper end is protruding from the DP housing, such that the cannula cap and the cannula opening are situated above the DP housing, and the sharp tip is situated within the well. During cannula insertion, the cannula cap is aligned with the DP housing, the cannula is crossing the bottom seal and the bottom spacer, and the cannula sharp tip is protruding below the DP housing through the adhesives base cannula aperture. After insertion, the cannula opening is aligned with the well, providing hydraulic communication between the exhaust chamber and the cannula via the second conduit.

In some embodiments, the patch pump IS operable when the RP and DP are connected. After RP-DP connection, the first reservoir resides within the RP vented compartment and the doser resides within the RP sealed compartment. The RP and DP are firmly and/or reversibly connected with the following interfaces: 1) an interface between a magnet (DP) and iron plate (RP) (or vice versa), and 2) an interface between adhesive (DP) and RP housing (RP). After use, the DP adhesive is peeled of the RP housing and magnet-iron plate are disengaged.

In some embodiments, a preloaded disposable inserter (inserter system, also known as the patch-pump assisting system) is provided. The inserter may include the inserter housing, an RP notch, safety catches, a viewing window, a trigger, DP holders, a preloaded spring, a rotating nut having a rotating thread and a splitter, and a hammer having a linear thread and a cannula pusher. The rotating thread and the linear thread can engage with each other. Upon pressing the trigger, the preloaded spring rotates the rotating nut, the rotating thread, and the splitter, the hammer is linearly displaced in the direction of the skin and the DP holders are displaced laterally. A fast linear displacement of the hammer and the hammer cannula pusher inserts the cannula into the body. After insertion, the inserter is removed and the patch pump is ready for operation.

In some embodiments, the inserter and the DP can be pre-assembled and provided in one sterile blister. The DP adhesives base may be situated at the bottom side of the inserter housing. The RP is inserted into the inserter housing through the RP notch and the RP is connected to the DP within the inserter housing. Following RP-DP connection, the first reservoir IS filled through the filling port and the patch pump is primed upon controller command.

In some embodiments, the first reservoir filling can be done with a syringe. After drawing fluid (e.g., drug such as insulin) from a vial, the drug can be injected from the syringe needle through the filling port into the first conduit and into the first reservoir. Air bubbles purging can be done automatically upon activation of the pumping mechanism with a controller command before cannula insertion. Fluid is dispensed (via the conduits and the dual chamber valve mechanism) from the first reservoir to the doser, from the doser to the well, from the well to the cannula tip (before insertion the cannula tip is situated within the well), and from the cannula tip to the cannula opening (before insertion, situated above the DP housing). When the inserter and DP housing are in upright position, trapped air may be purged from the cannula opening before the dispensed fluid. During priming, fluid drops dripping can be seen through the inserter viewing window. Viewing drops that are emerging from the cannula opening can notify the user that the patch pump is primed. After completion of priming, the inserter and the patch pump are adhered to the skin, the cannula is inserted, and the inserter is removed from the skin and disposed.

In some embodiments, the patch pump is provided with a reversible engagement mechanism between the RP lead screw and the DP second plunger. The engagement mechanism provides reversible rigid connection between the lead screw and the second plunger after RP-DP connection and allows disconnection of the lead screw from the second plunger during RP-DP disconnection. In some embodiments, the engagement mechanism comprises a scraper spring. The scraper spring is rigidly or substantially rigidly connected to the second plunger and comprises a flexible scaffold that is shaped with a recess than can be enlarged or diminished in size. In some embodiments, the scraper spring is comprised of a plurality of flat ribs (e.g., three flat ribs); each rib being folded outwardly in a petal like shape. In some implementations, the tip of the driving screw has a conical protrusion and the sleeve cover has a protrusion ("sleeve cover protrusion"). During RP-DP connection, the conical protrusion of the driving screw (part of the RP) is at least substantially rigidly engaged with the scraper spring (part of the DP). When the second plunger reaches the proximal end of the doser, the scraper spring is engaged with the sleeve cover protrusion and is slightly enlarged, the lead screw can be freely disengage from the scraper spring, and the RP can be freely disengage from the DP.

In some embodiments, the pumping mechanism may comprise a first reservoir, a first plunger, a second reservoir (doser), a second plunger, a dual chamber valve mechanism (valve mechanism), a first conduit, a second conduit, and a well. The dual chamber valve mechanism comprises two chambers, an inlet chamber and an exhaust chamber, and a sliding needle that is at least substantially rigidly connected to the doser. The sliding needle has a proximal end in hydraulic communication with the doser, a closed dead end at the distal end, and at least one opening at the mid-point. The first conduit communicates between the first reservoir and the inlet chamber ("first conduit") and the second conduit communicates between the exhaust chamber and the exit port. The first conduit is in hydraulic communication with the filling port. During first reservoir filling, fluid is injected (e.g., using a needle syringe) through the filling port and the first conduit into the first reservoir. The DP exit port (well) is comprised of a sealed cavity in communication with the second conduit. The cavity is sealed with a top seal and a bottom seal. During pump operation, fluid is delivered from the exhaust chamber through the second conduit into the well and from the well through the cannula into the patient's body.

In some embodiments, both the first reservoir and the second reservoir have a proximal end and a distal end. When the reservoir (first and second) is empty, the plunger is positioned at the distal end. While the reservoir is filling, the plunger is displaced in the direction of the proximal end, and when the reservoir is filled to maximal capacity, the plunger is positioned at the most proximal end. In some embodiments, the first reservoir has a shape of a cylinder, having a wall and a cavity. The cylinder cross section can be oval, elliptical, four arches, round, or any other symmetrical or nearly symmetrical configuration. The doser and the sliding needle may be linearly displaced, relative to the first reservoir, by a linear displacement of the lead screw and consecutively a linear displacement of the second plunger. When the second plunger is displaced in one direction, the doser and sliding needle are linearly displaced at the same first direction (e.g., forward direction) and the sliding needle opening is positioned within the inlet chamber. At this delivery phase (dosing filling phase) fluid is delivered from the first reservoir via the first conduit into the inlet chamber and into the doser. When the second plunger is displaced in the opposite direction, the doser and the sliding needle are linearly displaced in the same opposite direction (e.g., backward direction), and the sliding needle opening is positioned within the exhaust chamber. At this delivery phase (doser emptying phase) fluid is delivered from the doser via the exhaust chamber, the second conduit to the well, and from the well to the cannula. In some embodiments, the first plunger comprises a piston and two gaskets, a first proximal gasket and a second distal gasket. In some embodiments, the plunger comprises one piece that is made of a sealing material (e.g., rubber) and having two circumferential contact surfaces with the first reservoir cavity.

In some embodiments, the patch pump is provided with a doser sensor. Linear displacement of the second plunger induces two consecutive motions: first, displacement of the doser relative to the first reservoir and RP housing, and second, displacement of the second plunger relative to the doser. The patch pump is provided with a sensor that detects linear displacements of the doser relative to the first reservoir and RP housing (doser sensor). The doser sensor can be used for at least substantially precisely defining initiation of fluid delivery (e.g., by calculating insulin dosing) and/or detection of RP-DP connection/disconnection. When the second plunger is linearly displaced in one direction by the lead screw, the doser is displaced in the same direction due to frictional forces between the doser and the second plunger. When the doser reaches a rigid stopper (e.g., distal end of sleeve), further displacement of the second plunger displaces fluid within the doser at the same direction (e.g., insulin delivery). In some embodiments, the sensor is comprised of a photo-detector that is rigidly connected to the RP electronic module. The doser sensor detects linear movements of the doser sticker which can be a sliding identifier that is rigidly connected to the doser and is positioned in line of sight with the photo-detector. A non-limiting example of an identifier can be a barcode that may be comprised of a simple rectangular shaped tag containing black and white colors (in equal amounts, for example). In such example, black color can be interpreted and converted by the photo-detector to a relatively low current (or voltage). At initiation of the doser displacement in forward direction, the microprocessor of the electronic module activates the photo-detector. When the doser is further displaced in forward direction, the black tag gradually occupies the photo-detector window view and output voltage is reduced. When the doser displacement is stopped, output voltage remains constant and the microprocessor interprets the signal as no relative movement between photo-detector and doser sticker (and no relative movement between doser and RP housing). The doser sensor can provide alerts to the user of the patch pump in cases of improper RP-DP connection and/or inadvertent RP-DP disconnection during pump operation.

The operation cycle of the patch pumps includes at least two phases: 1) doser filling phase, and 2) doser emptying phase. In the doser filling phase, fluid is delivered from the first reservoir to the doser; in the doser emptying phase, fluid is delivered from the doser to the exit port. In the doser filling phase, displacement of the second plunger within the doser induces a negative pressure (relative to atmospheric pressure) in the inlet chamber, first conduit and first reservoir. Due to pressure gradient between the atmosphere and the first reservoir, fluid is delivered from the first reservoir to the second reservoir (doser) and the first plunger is displaced in the direction of fluid displacement. Pressure gradient between the atmosphere and the first reservoir forces air entry into the reservoir through the interface between the first plunger and the first reservoir. Air entry into the first reservoir forms air bubbles within the delivered fluid (insulin, for example) and may jeopardize the diabetes pump user with injection of air instead of injection of insulin. Moreover, during consecutive delivery cycles, air bubbles volume is increased and the total air bubbles volume may occupy a major portion of the first reservoir volume.

Embodiments of the current disclosure provide solutions to avoid air entry into the first reservoir, including active solutions and passive solutions. In the active solutions, the relative negative pressure in the first reservoir is actively increased to above atmospheric pressure, while in the passive solutions entry of air into the first reservoir is at least substantially prevented. In some embodiments of the active solution, the negative pressure is mitigated by reversal of the direction of fluid delivery at the end of the doser filling phase when there is a fluid communication between the doser and the first reservoir. Flow delivery from the doser into the first reservoir increases the pressure within the first reservoir above atmospheric pressure and thus, air movement is now following the reversed pressure gradient from the first reservoir to the outside atmosphere. The reversal of direction of fluid delivery is achieved by reversal of direction of displacement of the second plunger (from filling phase to emptying phase). At the beginning of the second plunger displacement (emptying phase), a doser locker is activated and temporarily, the doser is rigidly fixed in place. At this stage, displacement of the second plunger displaces fluid from the doser into the first reservoir. Upon deactivation of the doser locker, doser fixation is removed, and further displacement of the second plunger displaces the doser and the sliding needle until the openings of the sliding needle are positioned in the exhaust chamber. At this stage, further displacement of the second plunger displaces fluid from the doser into the exhaust chamber, second conduit, well, cannula, and into the patient body. The doser locker may be operated by, for example, a nitinol wire, solenoid, piezoelectric actuator, and/or the like. In the nitinol based doser locker, the nitinol wire is pre-shaped in the form of a spring; when electric current is delivered to the spring, the total length of the spring coils is decreased (as a result of nitinol constriction phenomenon, for example), and consequently the doser locker is displaced and engaged with the doser. When the electric current is stopped, the nitinol wire resumes its length, the doser locker is disengaged from the doser, and the doser can be freely displaced.

In some embodiments of the passive solution, air entry into the first reservoir is prevented by a fluid that resides between the two gaskets of the first plunger. The fluid can be, for example, oil or any other high viscosity fluid that may be injected between the two gaskets. In some embodiments, the fluid is insulin that is injected between the gaskets during the first reservoir filling. The first reservoir is provided with a circumferential cavity at the distal end that is slightly larger than the other portions of the reservoir cavity. The first plunger is provided with a slot that is in communication to the outside atmosphere, the slot allowing air purging and blocking fluid purging (fluid restrictor). During filling of the first reservoir, the plunger is situated at the first reservoir distal end, the fluid initially occupies the space between the gaskets, and air is purged through the fluid restrictor to the atmosphere. When the space between the gaskets is fully occupied with fluid, additional fluid injected into the first reservoir displaces the plunger in the direction of the proximal end of the first reservoir. At this stage of the first reservoir filling, the first gasket of the first plunger is in closed contact with the first reservoir wall, and sealing between the first reservoir cavity and wall is maintained.

In some embodiments, the patch pump is provided with reservoir sensor. The reservoir sensor may include an axial pole magnet that can be attached to the first reservoir plunger and two hall sensors that reside in the RP sealed compartment in close proximity to the first reservoir. The hall sensors can be transducers that change their outputs voltage in response to a magnetic field. With a known magnetic field, their distance from the axial pole magnet (and first reservoir plunger) can be determined and the relative position of the plunger can be deduced. The axial pole magnet and plunger are displaced within the first reservoir during first reservoir filling and during pump operation. It is to be noted that, although discussions of embodiments in the current disclosure related to the magnet refer to an axial pole magnet, the use of any other magnet type is deemed to be within the scope of the inventive embodiments described herein (and as such not limited to axial pole magnets).

In some embodiments, the patch pump is ready for use after filling the first reservoir, inserting the RP within the inserter housing, connecting the RP and the DP with the magnet/iron plate and adhesives base, purging air (priming), adhering the adhesives base to skin, pressing the inserter trigger, inserting the cannula, and disposing the inserter. At the end of the patch pump use (which may be, in some instances, after 2-5 days of usage), the pump can be removed from the body by disconnecting the bottom surface of the adhesives base from the skin. After pump removal, the adhesives base can be folded over the cannula, protecting the patient from inadvertent self-pricking. The RP is then disconnected from the DP by disconnecting the RP iron plate from the DP magnet (or vice versa). Following RP-DP disconnection, the RP is placed in the charger to recharge the RP battery for additional operating cycle, and the DP is disposed.

Some of the advantages of the embodiments of the present disclosure include the miniature size of the devices (as such, conveniently portable), their accuracy and ease of integration. For example, the devices and systems may possess the ability to integrate with closed and open loop diabetes management systems. Further, they can be utilized for a much longer duration than can be the case with conventional systems. In addition, the present embodiments disclose methods of removing air bubbles from fluids, a feature that distinguishes these features from conventional methods and systems.

In some embodiments, a portable device that contains an insulin reservoir m communication with a subcutaneous cannula and a method for continuous (basal) and on-demand (bolus) delivery of insulin is disclosed. Basal and bolus administration rates may contribute to enhanced accuracy for the delivery of insulin. In some embodiments, an ambulatory skin adherable insulin pump (patch pump) that is substantially smaller, less bulky, thinner and lighter than previously known insulin delivery systems is disclosed. Further, the skin adherable patch pump can be concealable. In some embodiments, the device may not have operating buttons and/or may be remotely controlled. In addition, the patch pump can be controlled with a variety of consumer electronic devices that may be used by the patient such as but not limited to smartphone, smart-watch, tablet, and/or PC.

Some embodiments of the current disclosure disclose a patch-pump assisting system configured to at least function to insert a cannula in tissue, the system comprising: a housing; a disposable part (DP) of a patch-pump drug delivery system removably affixed to the housing; a notch or opening formed in a side of the housing and configured to receive at least a reusable part (RP) of the patch-pump drug delivery device; at least two safety catches arranged on the housing; and an insertion mechanism configured to insert a cannula upon activation thereof.

The above-noted embodiments (as well as other embodiments disclosed in the present disclosure), may include at least one or another (or a plurality of any) of the following features, structures, functionality, providing yet further embodiments of the present disclosure:

the patch-pump assisting system comprises a trigger for activating the insertion mechanism;

upon the notch receiving the RP, the RP and DP can become connected;

the patch-pump assisting system comprises a releasing mechanism configured to release the connected DP and RP after activation of the insertion mechanism;

the DP includes a reservoir, and the housing can be configured to receive an external supply of a drug for filling the reservoir via a filling aperture;

the RP of the patch-pump includes a motor configured to effect priming of the patch-pump automatically upon connection with the DP;

the cannula is configured with at least two openings, a first opening configured for priming the patch-pump and a second opening configured to deliver the drug once inserted into tissue;

the first opening is arranged at or adjacent a proximal end of the cannula and the second opening is arranged at or adjacent the distal end of the cannula, the distal end being inserted first into tissue;

the first opening is in fluid communication with the reservoir of the DP;

the cannula is inserted via triggering of the insertion mechanism and upon concomitant pressing of the at least two safety catches;

the cannula is configured to be inserted into the tissue through the DP of the patch-pump;

the patch-pump assisting system may further comprise a cannula cap configured to seal a groove in the proximal end of the cannula;

upon insertion of the cannula into tissue, the cannula is rigidly connected to the patch-pump and in fluid communication therewith;

at least one of the insertion mechanism and a releasing mechanism includes a pivoting rod, a rotating nut, a spring, a trigger, and a hammer;

the trigger includes a trigger stopper, and a rotating nut stopper;

the rotating nut stopper includes a rotating thread and a splitter;

the hammer includes at least one of a hammer linear thread, a hammer lead, and a cannula pusher;

the rotating thread is configured for engagement with the hammer linear thread;

the movement of the trigger and the rotating nut stopper allows rotation of the spring and the rotating nut;

energy stored in the spring rotates the rotating nut, the rotating thread, and the splitter;

the rotation of the rotating nut causes linear displacement of at least one of the hammer and the cannula pusher;

the rotation of the splitter causes linear displacement of one or more DP holders, which is configured to release the system after cannula insertion;

the patch-pump assisting system is configured to at least one of: align the RP and DP during connection thereof; hold the patch-pump during at least one of filling, priming, and skin adhesion thereof; and semi-automatic cannula insertion upon trigger activation;

the patch-pump assisting system may comprise a window configured to provide one or more views for observing drug release during patch-pump priming;

upon activating the trigger, the rotating nut stopper linearly displaces and the rotating nut is free to rotate around the pivoting rod;

the hammer lead is configured to maintain linear displacement of the hammer during movement in a first direction;

upon activation of the system, the cannula pusher pushes the cannula in the first direction;

the trigger stopper is released by depressing or otherwise moving a safety catch;

the patch-pump assisting system may further comprise at least one disposable part (DP) holder, wherein the DP holder is configured to hold an adhesive base of a disposable part (DP) of the patch pump substantially in place at a bottom side of the assisting system prior to activation of the insertion mechanism and cannula insertion;

after the insertion mechanism is activated, the DP holder is laterally displaced and the adhesive base is released;

the DP holder is configured to hold the adhesive base substantially in place prior to activating the insertion mechanism;

after the insertion mechanism is activated, the DP holder is laterally displaced to release the adhesive base for removal of the assisting system;

the insertion mechanism comprises at least a rotational element and a first linear displacement element, and upon activation of the insertion mechanism by the trigger, rotational movement of the rotational element is converted to linear movement of the first linear displacement element to insert the cannula into the tissue;

the rotational movement of the rotational element occurs in a first plane, and the linear movement of the first linear displacement element occurs m a second plane approximately perpendicular to the first plane;

the insertion mechanism includes a second linear displacement element, and the rotational movement of the rotation element linearly displaces the first linear displacement element in a first plane, orthogonal to the plane of rotation, and linearly displaces the second linear element in a second plane, orthogonal to both the rotational element and first linear displacement element; and the patch-pump assisting system further comprises a liner removably affixed to the adhesive base.

Some embodiments of the current disclosure disclose a method for using a patch-pump drug delivery system. Such a method may comprise the steps of providing patch-pump drug delivery system having a reusable part (RP) and a disposable part (DP); providing the patch-pump assisting system disclosed above; and receiving, via the notch of the assisting system, the reusable part (RP) of the patch-pump such that the RP of the patch pump is connected with the DP of the patch pump.

The above-noted embodiments (as well as other embodiments disclosed in the present disclosure), may include at least one or another (or a plurality of any) of the following features, structures, functionality, method steps, providing yet further embodiments of the present disclosure:

folding the/a liner of the adhesive base around upper and bottom sides of the adhesive base of the DP;

filling a reservoir of the DP of the patch-pump with a drug for delivery by the patch-pump via a filling aperture;

priming the patch-pump;

viewing at least one of the DP, a cannula and a cannula cap via a window of the assisting system;

viewing drops of liquid emerging from an opening in a proximal portion of the cannula via a window in the assisting system, where in some embodiments, the cannula is configured to elude drop of the drug during priming from one or more first openings arranged on a proximal end thereof;

automatically activating priming of the patch-pump upon connection of the RP with the DP via a motor in the RP;

removing the liner and adhering the patch pump to the skin of the user;

depressing the trigger and the at least two safety catches concomitantly to activate the insertion mechanism for insertion of the cannula in tissue; and activating the insertion mechanism to effect at least one of insertion of the cannula and detachment of the patch-pump.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 10A-B show a longitudinal cross section view of the driving mechanism, according to some embodiments.

FIGS. 11A-B show a cross section view and a spatial view of the RP, according to some embodiments.

FIGS. 19A-D show spatial views and longitudinal cross section views of the DP before and after cannula insertion, according to some embodiments.

FIGS. 20A-B show longitudinal cross section views through the DP cannula grove and filling conduit, before and after cannula insertion, according to some embodiments.

FIGS. 21A-D show longitudinal cross section views of the DP groove, according to some embodiments.

FIG. 28 shows a spatial view of the adhesive base, according to some embodiments.

FIGS. 30-34 show sequential processes of the patch pump handling including RP-DP connection, liner removal, cannula insertion, patch pump removal, flex base folding, and RP-DP disconnection, according to some embodiments-, in particular, and according to some embodiments:

FIG. 30A shows an inserter 300 with the DP;
FIG. 30B shows the insertion of the RP into the inserter;
FIG. 30C shows the RP within the inserter;
FIG. 30D shows a liner peeling in process.

FIGS. 35-44 show the inserter 300, inserter activation, and inserter operation including inserter components, mechanism of action, and user interface, according to some embodiments. In particular, and according to some embodiments:

FIGS. 45A-B show cross section, partially transparent views (viewing window perspective) of the inserter and the patch pump before and after cannula insertion, according to some embodiments.

FIGS. 46-54 show reversible engagement mechanisms between the RP lead screw and the DP doser plunger, according to some embodiments. In particular, and according to some embodiments:

FIGS. 47A-C show magnified spatial views of the spring scraper and the lead screw.

FIGS. 49A-C show spatial views (FIGS. 49A-B) and cross-sectional view (FIG. 49C) of a bayonet engagement mechanism;

FIG. 52 shows a cross sectional view of an O-ring engagement mechanism;

FIGS. 53A-B shows cross sectional (FIG. 53A) and spatial view (FIG. 53B) of a pot magnet engagement mechanism;

FIGS. 59-64B show the disposable components of the pumping mechanism and the operation cycle of the pumping mechanism, according to some embodiments. In particular, with reference to FIG. 64A-B, FIG. 64A is a cross-section view, and FIG. 64B is a spatial view of a sliding needle;

FIGS. 68A-70 show the components and operation modes of the doser sensor, according to some embodiments. In particular, and according to some embodiments:

FIGS. 68A-B show a doser sensor operation during a pump operation cycle, and FIG. 68C shows the operation of the doser sensor during RP-DP disconnection, and FIGS. 70A-E shows cross section views of the doser sensor during pump operation and during RP-DP disconnection—FIG. 70A (doser emptying phase), FIG. 70B (doser filling phase), FIG. 70C (a first stage of RP-DP inadvertent disconnection), FIG. 70D (a next consecutive stage of RP-DP disconnection), and FIG. 70E (completion of RP-DP disconnection).

FIGS. 74-83 show the components and the operation modes of air bubbles protection means, according to some embodiments.

DETAILED DESCRIPTION OF SOME OF THE EMBODIMENTS

Figure 1:
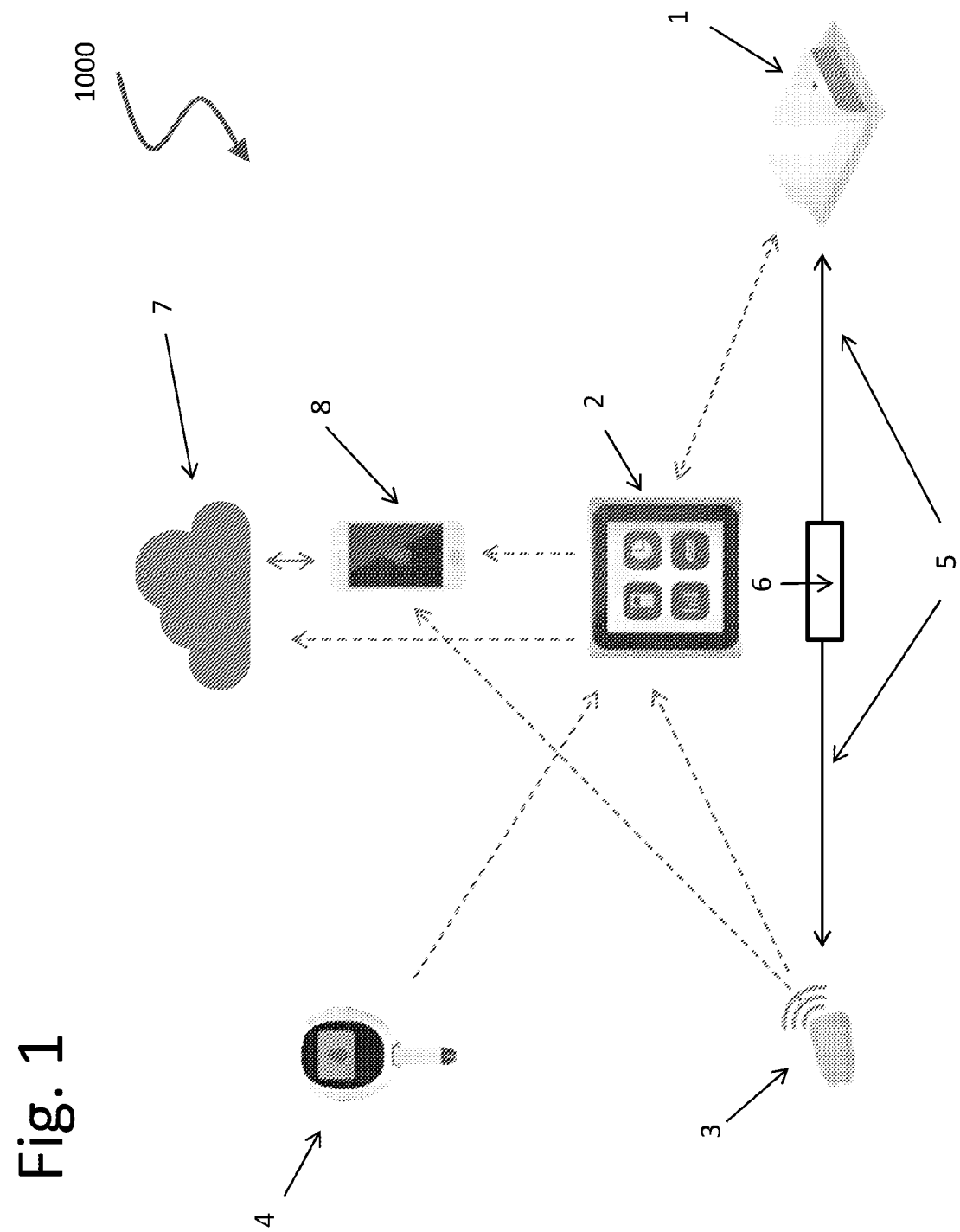
FIG. 1 shows a diabetes management system, according to some embodiments.

FIG. 1 shows a scheme of a diabetes management system 1000, according to some embodiments. The system includes at least one of the following components: insulin patch pump 1, controller 2, smartphone 8, continuous glucose monitor (CGM) 3, blood glucose monitor (BGM) 4, and a cloud 7 of server(s). System 1000 components may be configured to communicate with each other in one- and/or two-way communication channels. For example, a two-way communication may occur between pump I and controller 2, while a one way communication may occur between the pump I and the smartphone 8 (e.g., from the pump to the smartphone) or between the pump I to the cloud 7 (e.g., from the pump to the could). Communication protocols could be one or more of Bluetooth, Bluetooth Low Energy (BLE), WiFi®, and any other RF protocol (including proprietary ones) such as but not limited to RFID. Pump controller 2 may provide an interface for the user with pump I for commanding basal and bolus doses and profiles and for receiving alerts, alarms, log files, etc. Communication between CGM 3 and pump I may provide artificial pancreas (closed loop system 5) functionality in which insulin doses are automatically administered according to monitored glucose levels of CGM 3 and algorithm 6. Transmitted readings from BGM 4 and/or CGM 3 to pump controller 2 and/or smartphone 8 provide the user with glucose readings for calculating insulin dosing. Real time and stored data from pump 1, pump controller 2, CGM 3, and BGM 4 may be transmitted to smartphone 8 to be presented or stored. Two-way cellular communication of smartphone 8 with cloud 7 may provide the patient with ability to download personal data stored at a remote server. Data in cloud 7 may be downloaded, processed, and transmitted to and from a PC, remote smartphone, or any other BLE or wireless communication enabled consumer product.

Figure 2:
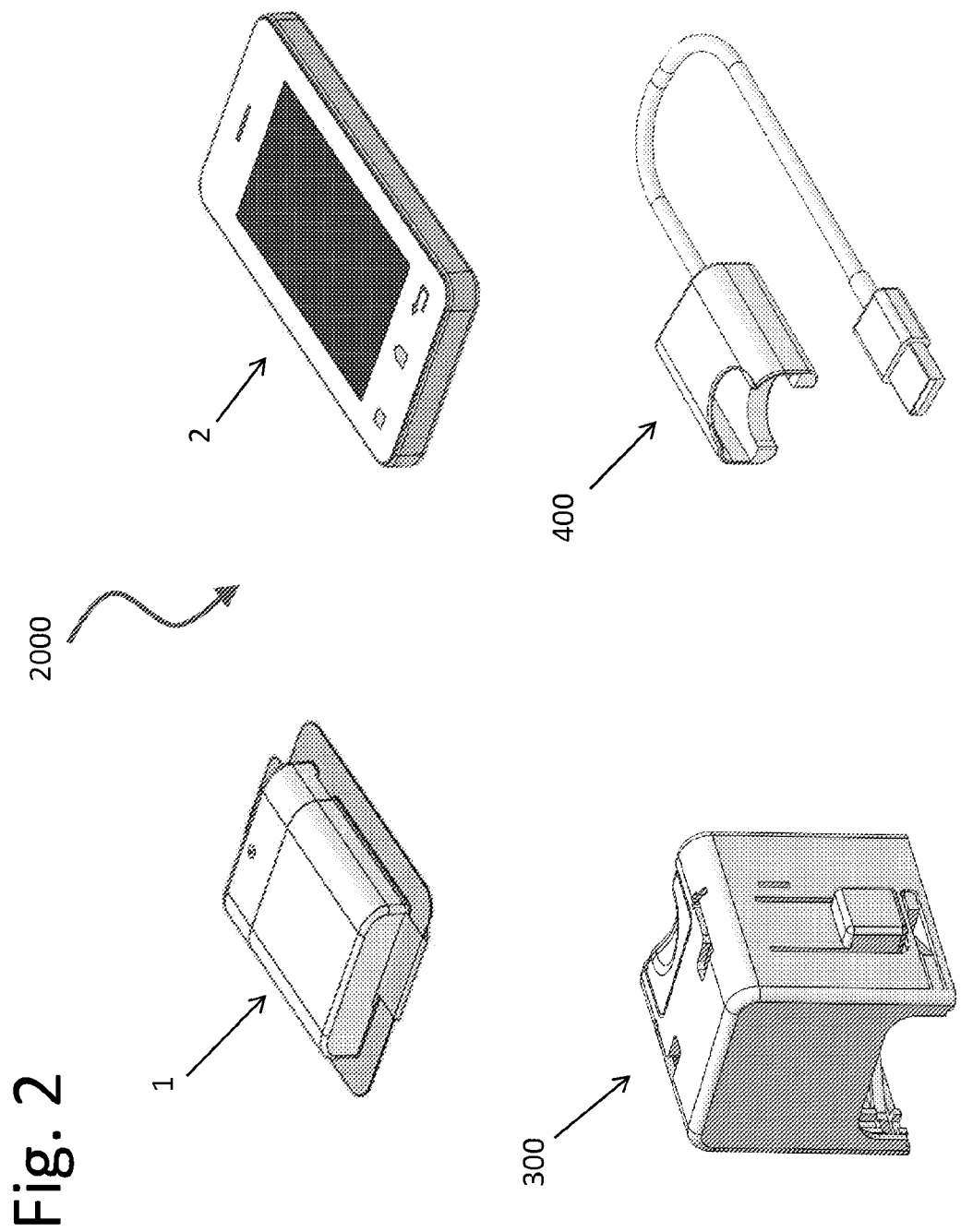
FIG. 2 shows the top level components of the insulin delivery system, according to some embodiments.

FIG. 2 shows the top level components of the insulin delivery system 2000, according to some embodiments. The system 2000 may include a patch pump 1, a controller 2, an inserter 300 for inserting the insulin delivery cannula into the subcutaneous tissue (interchangeably referred to as a patch-pump assisting system throughout the instant disclosure), and a charger 400 for charging the RP power source, such as a battery. In some embodiments, the length of the patch pump 1 may be in the range from about 30 mm to about 50 mm, from about 32 mm to about 45 mm, from about 35 mm to about 40 mm, about 37 mm, including values and subranges therebetween. In some embodiments, the width of the patch pump 1 may be in the range from about 20 mm to about 40 mm, from about 24 mm to about 36 mm, from about 22 mm to about 32 mm, about 30 mm, including values and subranges therebetween. In some embodiments, the height of the patch pump 1 may be in the range from about 4 mm to about 20 mm, from about 6 mm to about 14 mm, from about 8 mm to about 12 mm, about 10 mm, including values and subranges therebetween. In some embodiments, the weight of the patch pump 1 (including the weight of a fluid drug such as insulin when filled with it) may be in the range from about 0.2 oz to about 1 oz, from about 0.3 oz to about 0.8 oz, from about 0.4 oz to about 0.6 oz, about 0.56 oz, including values and subranges therebetween.

Figure 3:
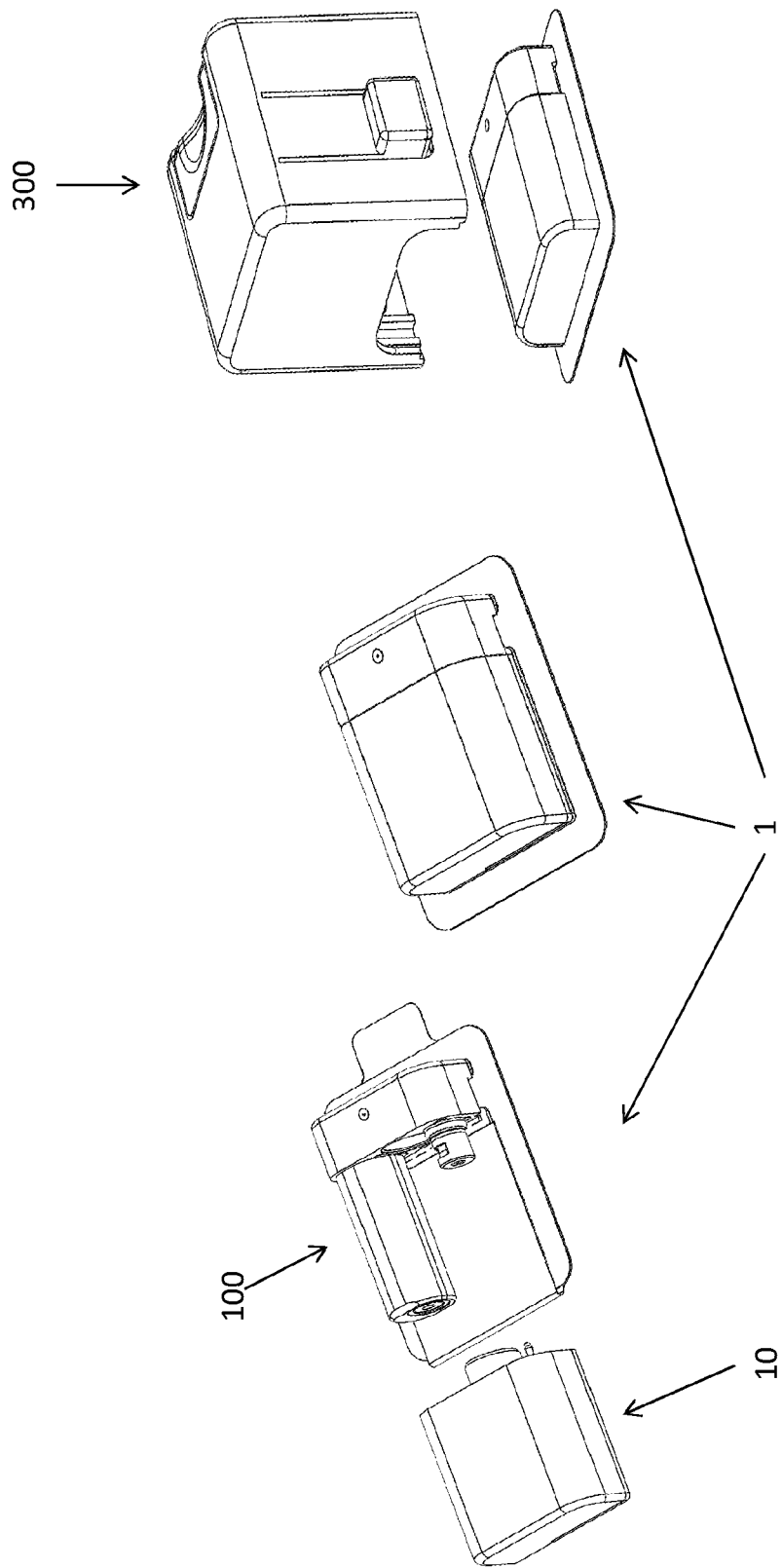
FIGS. 3A-C show the patch pump before RP-DP connection (FIG. 3A), after RP-DP connection (FIG. 3B), and after inserter removal (FIG. 3C), according to some embodiments.

FIGS. 3A-C show the patch pump 1 before RP-DP connection (FIG. 3A), after RP-DP connection (FIG. 3B) and after inserter 300 removal (FIG. 3C), according to some embodiments. The patch pump 1 is comprised of a reusable part (RP) 10 and a disposable part (DP) 100.

Figure 4:
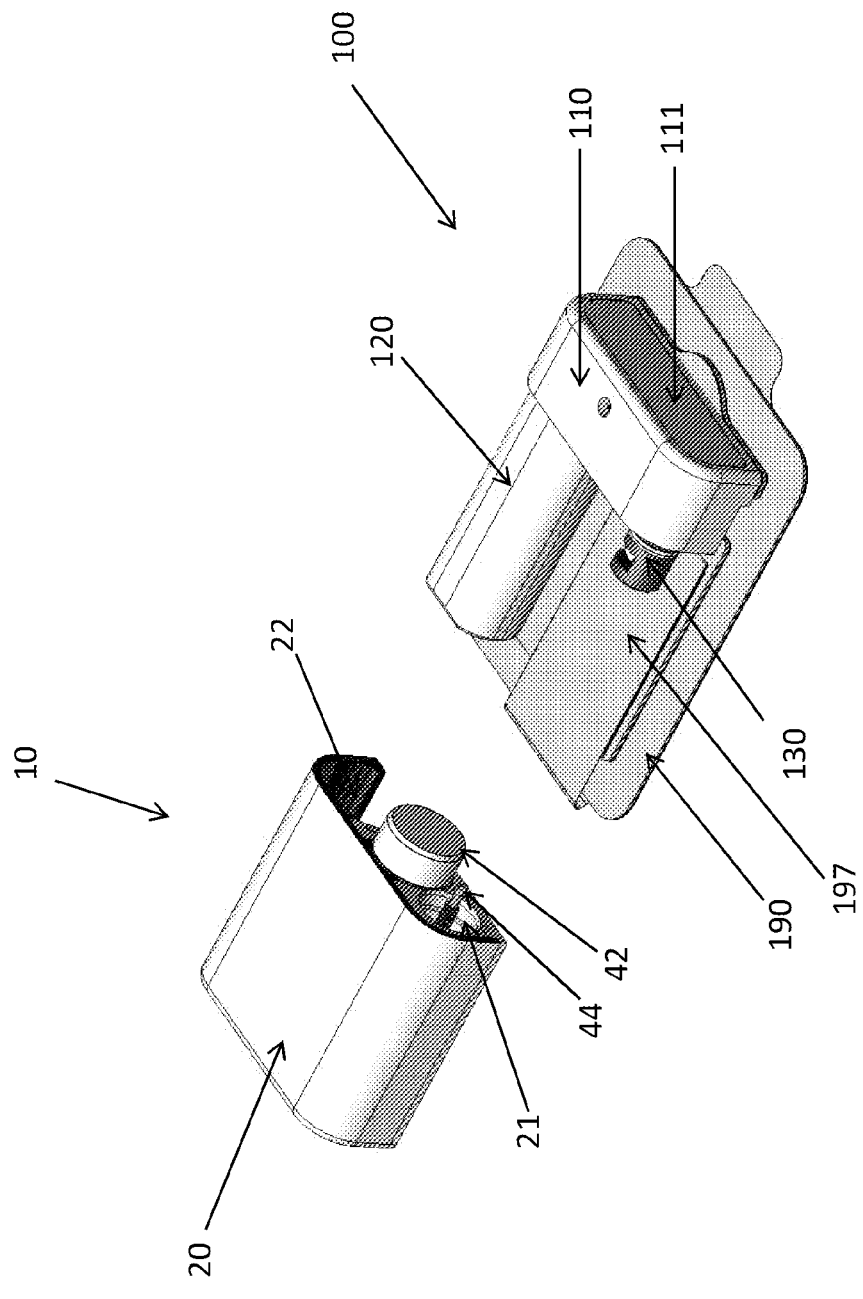
FIG. 4 shows the main components of the RP and the DP, according to some embodiments.

FIG. 4 shows the main components of the RP 10 and the DP 100, according to some embodiments. The RP 10 may include a housing 20 and at least two compartments, including a vented compartment 22 and a sealed compartment 21. The RP driving mechanism may include a motor 42 and a lead screw 41. The DP 100 may include a housing 110, a front foil 111, a first reservoir 120, a second reservoir (doser) 130, and an adhesive base 190. Before RP-DP connection, the adhesive base 190 may be covered with a removable liner 197.

Figure 5:
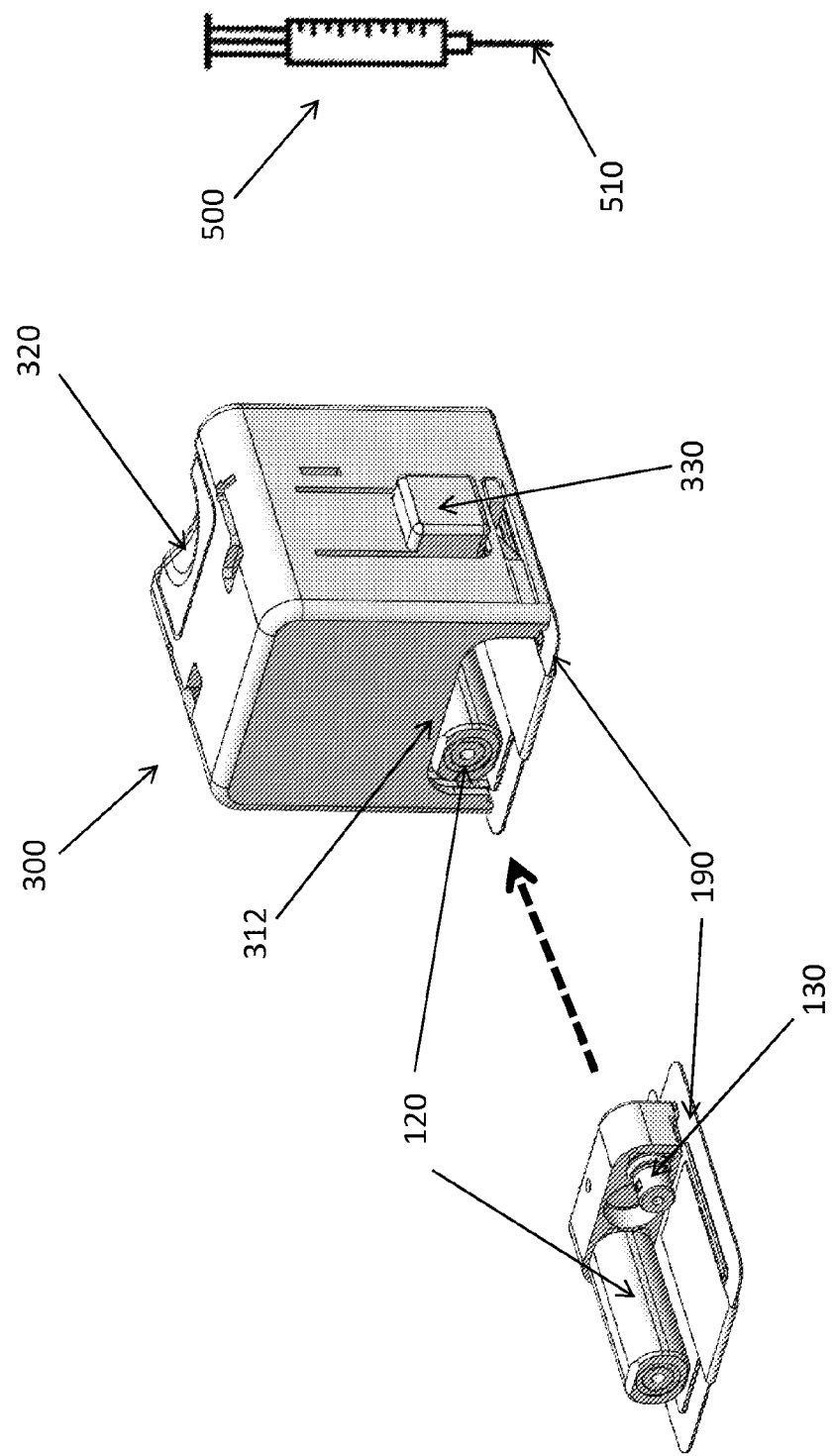
FIG. 5 shows the assembly of the DP within the inserter, according to some embodiments.

FIG. 5 shows the assembly of the DP 100 within the inserter 300, according to some embodiments. The DP includes the first reservoir 120, the doser 130, and the adhesive base 190. The inserter 300 includes a trigger 320, safety catches 330, and an RP notch 312. After the process of assembly (doted arrow) of the DP 100 within the inserter 300, the adhesive base 190 is situated at the bottom side of the inserter 300. In some embodiments, a filling syringe 500 is provided. The syringe 500 is used to draw fluid (e.g., insulin) from a vial and fill the first reservoir 120 using the syringe needle 510. In some embodiments, the assembled inserter-DP and syringe 500 are provided within one sterile blister (not shown).

Figure 6:
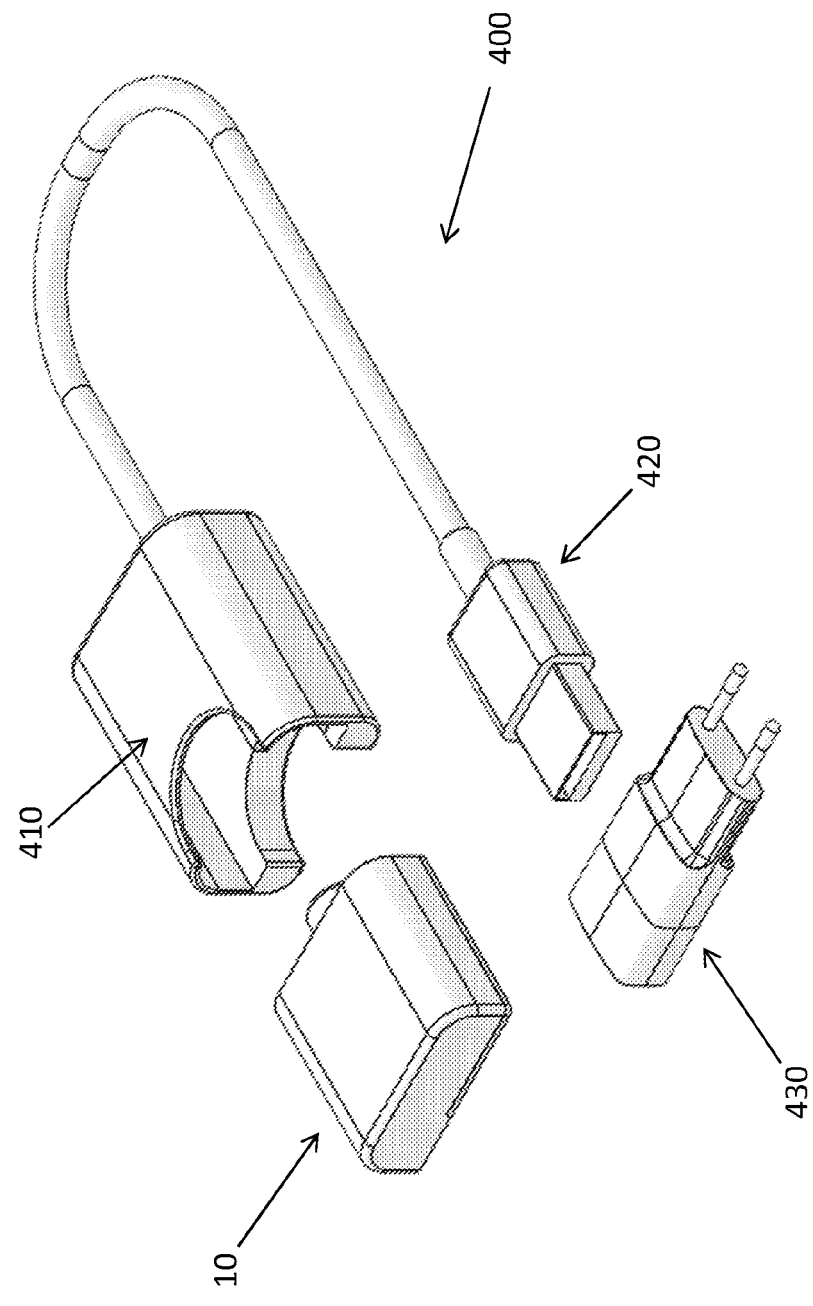
FIG. 6 shows the components of the charger, according to some embodiments.

FIG. 6 shows the components of the charger 400 including charging adaptor 410, USB plug 420, and electric plug 430, according to some embodiments. In some embodiments, the insulin delivery system may include a plurality of RPs. For example, the insulin delivery system may include two RPs 10, and in such embodiments, when one RP 10 is operating and the second RP 10 is connected to the charger 400 for battery charging. Battery charging can be done with any other connector that can be directly plugged into the RP (USB, micro USB, pin connector, etc.).

Figure 7:
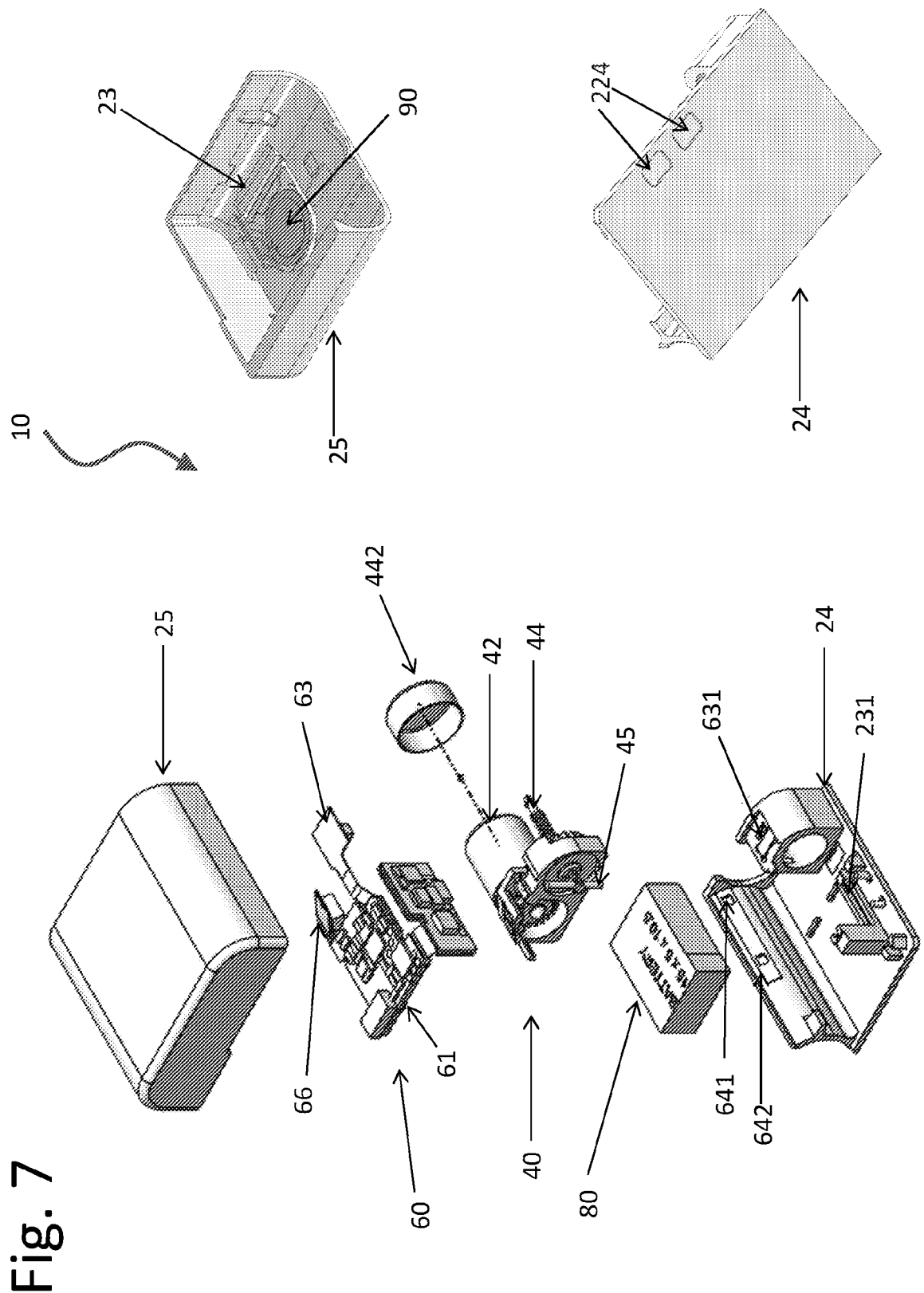
FIG. 7 shows the main components of the RP, according to some embodiments.

FIG. 7 shows some of the main components of the RP 10, according to some embodiments. The RP housing (20, not shown) is composed of the RP cover 25 and RP base 24. The RP cover 25 includes a buzzer 90 that is embedded within the RP cover 25 and the upper RP groove 23. The RP base 24 includes the two embedded charging pads 224 (bottom side), bottom RP groove 231, doser sensor socket 631, reservoir sensors socket one 641, and reservoir sensor socket two 642. The RP 10 includes the driving mechanism 40, electronic module 60, and battery 80. The driving mechanism 40 includes a motor 42, a motor cover 442, a lead screw 44, and a lead screw pin 45. The lead screw pin 45 is freely sliding within the bottom RP groove 23 and the upper RP groove 231 and prevents rotation of the drive screw 44 during motor 42 operation. The electronic module 60 may include a PCB 61, a doser sensor 63, and an encoder sensor 66.

Figure 8:
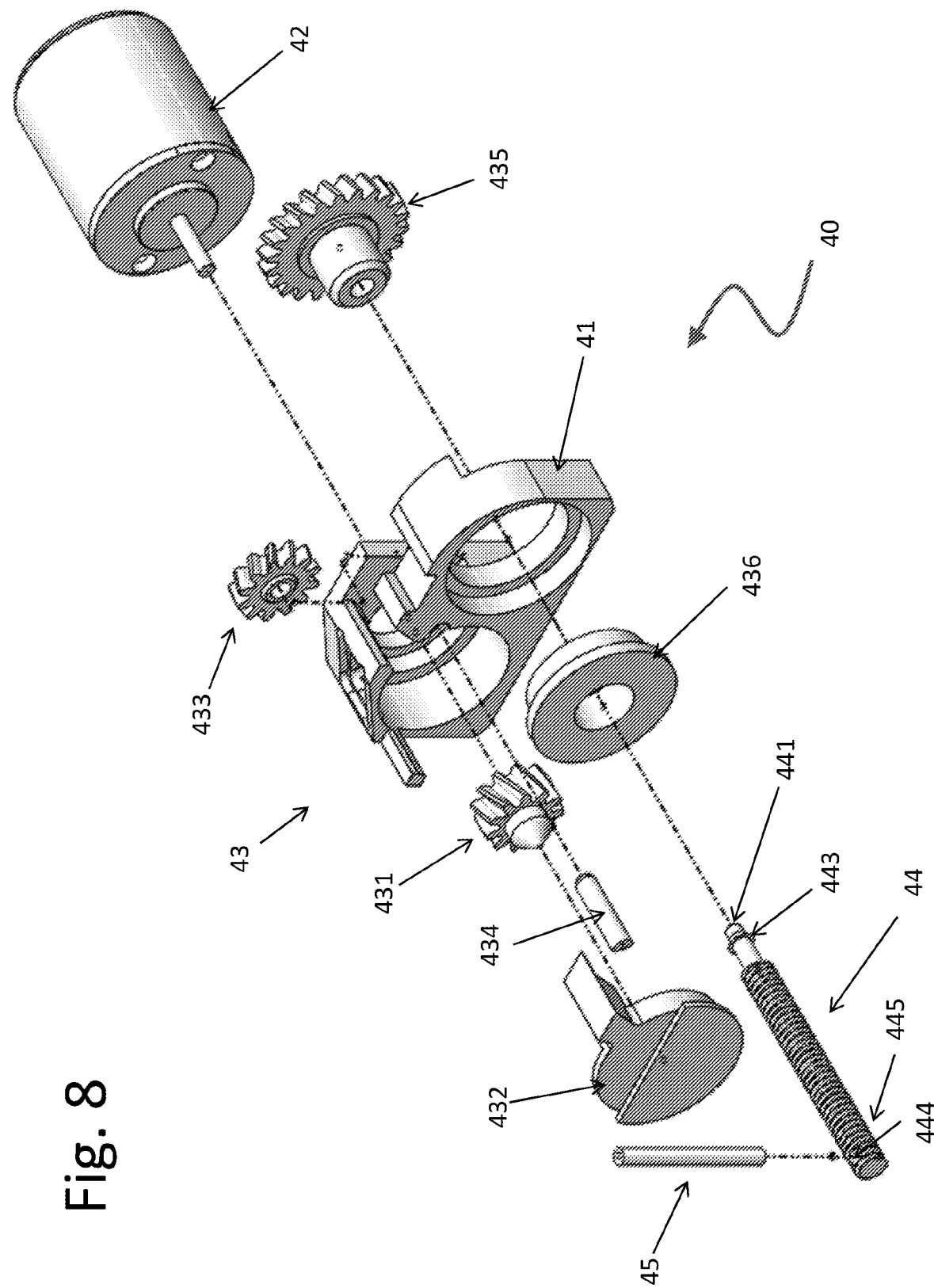
FIG. 8 shows an exploded view of some parts of the driving mechanism, according to some embodiments.

FIG. 8 shows an exploded view of some of the parts of the driving mechanism 40 that includes the gear 43, motor 42, and lead screw 44, according to some embodiments. The driving mechanism base 41 is a chassis that aligns the three gear cogwheels—pinion 431, idler 433 and rotating nut 435. The three cogwheels can be spur or helical or of any other kind. A pinion cover 432 holds the pinion 431 in place. In some embodiments, a bearing 436 provides free rotation of the rotating nut 436 within the driving mechanism base 41 and the idler 433 pivots around an idler shaft 434. The lead screw 44 comprises a lead screw tip 441, a lead screw tail 445, a lead screw protrusion 443, and a lead screw opening 444. The lead screw 44 is engaged with the rotating nut 425. In some embodiments, a lead screw pin 45 transverses perpendicularly the lead screw opening 444 and prevents rotation of the lead screw 44 during motor 42 operation. Operation of the motor 42 may rotate the pinion 431, idler 433, and rotating nut 435, and linearly displace the lead screw 44 in one direction. Reversal of motor 42 direction of revolution linearly can displace the lead screw 44 in the opposite direction.

Figure 9:
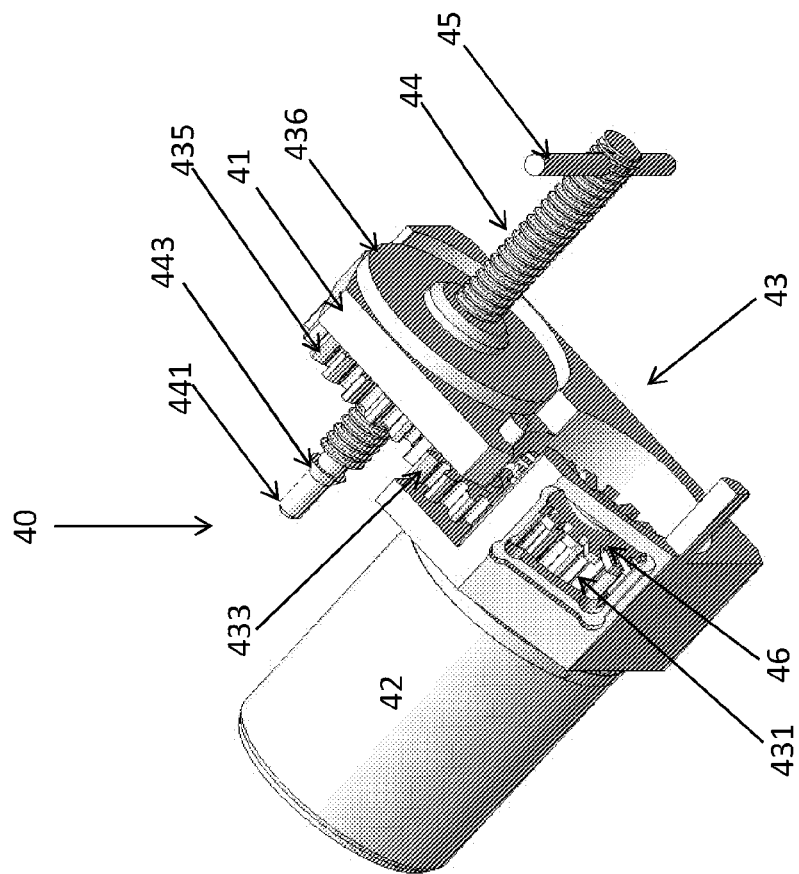
FIG. 9 shows a spatial view of the assembled driving mechanism, according to some embodiments.

FIG. 9 shows a spatial view of the assembled driving mechanism 40, according to some embodiments. The driving mechanism 40 comprises the driving mechanism base 41 that serves as a chassis for the motor 42, assembled gear 43, and lead screw 44. The gear includes the pinion 431, idler 433, rotating nut 435, and rotating nut bearing 436. The motor sensor (encoder) 46 is attached to the pinion 431. The lead screw 44 is engaged with the rotating nut 435, and includes the lead screw tip 441 and lead screw protrusion 443. The lead screw pin 45 prevents rotation of lead screw 44 during motor 42 and gear 43 operation.

FIGS. 10A-B show a longitudinal cross section view of the driving mechanism 40 without the lead screw 44 (FIG. 10A) and with the lead screw 44 (FIG. 10B), according to some embodiments. The driving mechanism base 41 supports the motor 42, pinion 431, pinion cover 432, idler 433, rotating nut 435, bearing 436, and encoder 46. The lead screw 44 is engaged with the rotating nut 435 (FIG. 10B) and includes a lead screw tip 441, a lead screw tail 445, and a lead screw opening 444.

FIGS. 11A-B show a cross sectional view (FIG. 11A) and a spatial view (FIG. 11B) of the RP 10, according to some embodiments. The RP 10 is comprised of an RP housing 20 and is divided (dashed lines) to at least two compartments, including a vented compartment 22 and a sealed compartment 21. The vented compartment 22 includes a cavity 222 that occupies the DP first reservoir and the sealed compartment 21 includes a cavity 221 that occupies the DP second reservoir (after RP-DP connection). The sealed compartment 21 has an opening (sealed compartment opening 26), the opening 26 can be sealed by the DP-RP O-ring (FIG. 12) after RP-DP connection. The sealed compartment 21 includes a motor 42, a gear 43, a battery 80, and a lead screw 44*a-b*. The lead screw (44*a-b*) is shown in its most forward (distal) position 44*a* and backward (proximal) position 44*b*. A magnet/iron plate 70 is attached to the motor cover 442, providing firm interface with the DP magnet/iron plate.

Figure 12:
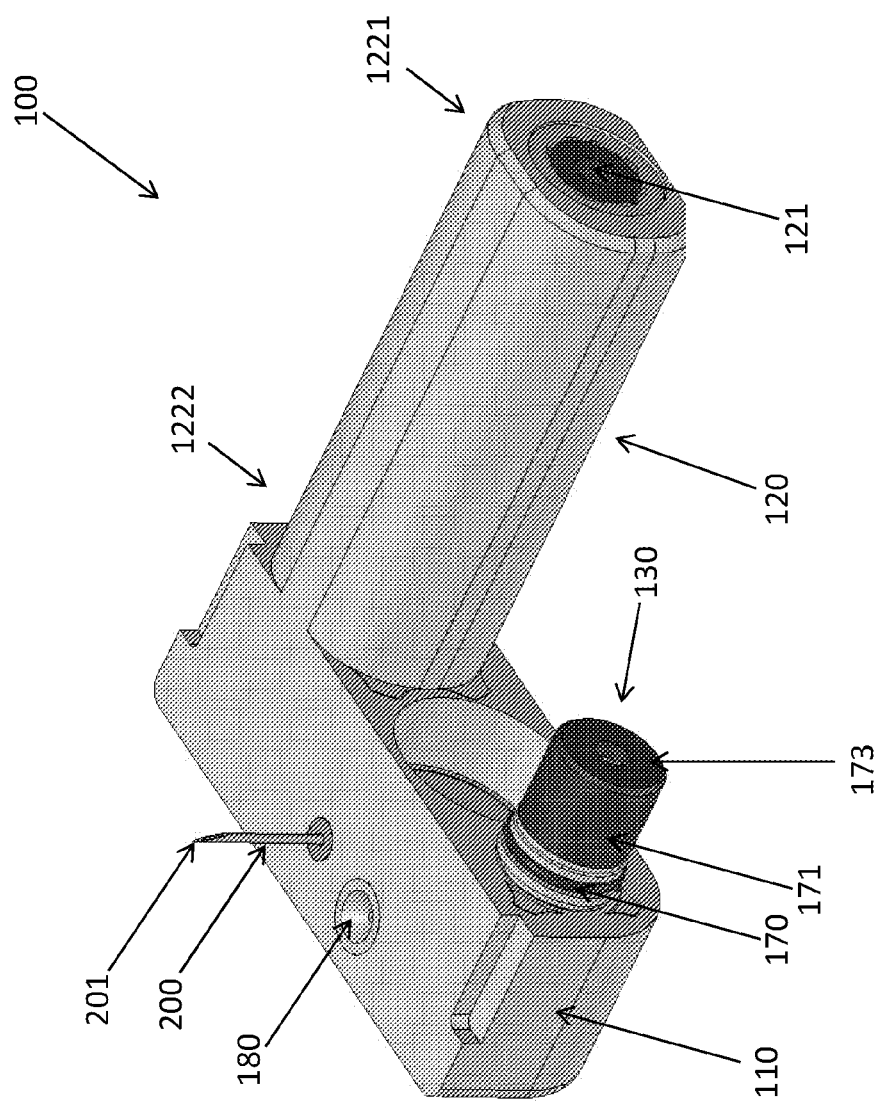
FIG. 12 shows a spatial view (bottom side) of some of the components of the DP, according to some embodiments.

FIG. 12 shows a spatial view (bottom side) of some of the components of the DP 100, according to some embodiments. The DP 100 includes a housing 110, a first reservoir 120, a second reservoir (doser) 130, a sleeve 171, a filling port 180, and a cannula 200. In some embodiments, the cannula is rigid (steel cannula) having a sharp tip 201. The first reservoir 120 has a first plunger 121, a proximal end 1221, and a distal end 1222. The doser 130 (covered with sleeve 171) can freely move within the sleeve 171. The sleeve 171 has a sleeve cover 173 and it is encircled by the DP-RP O ring 170.

Figure 13:
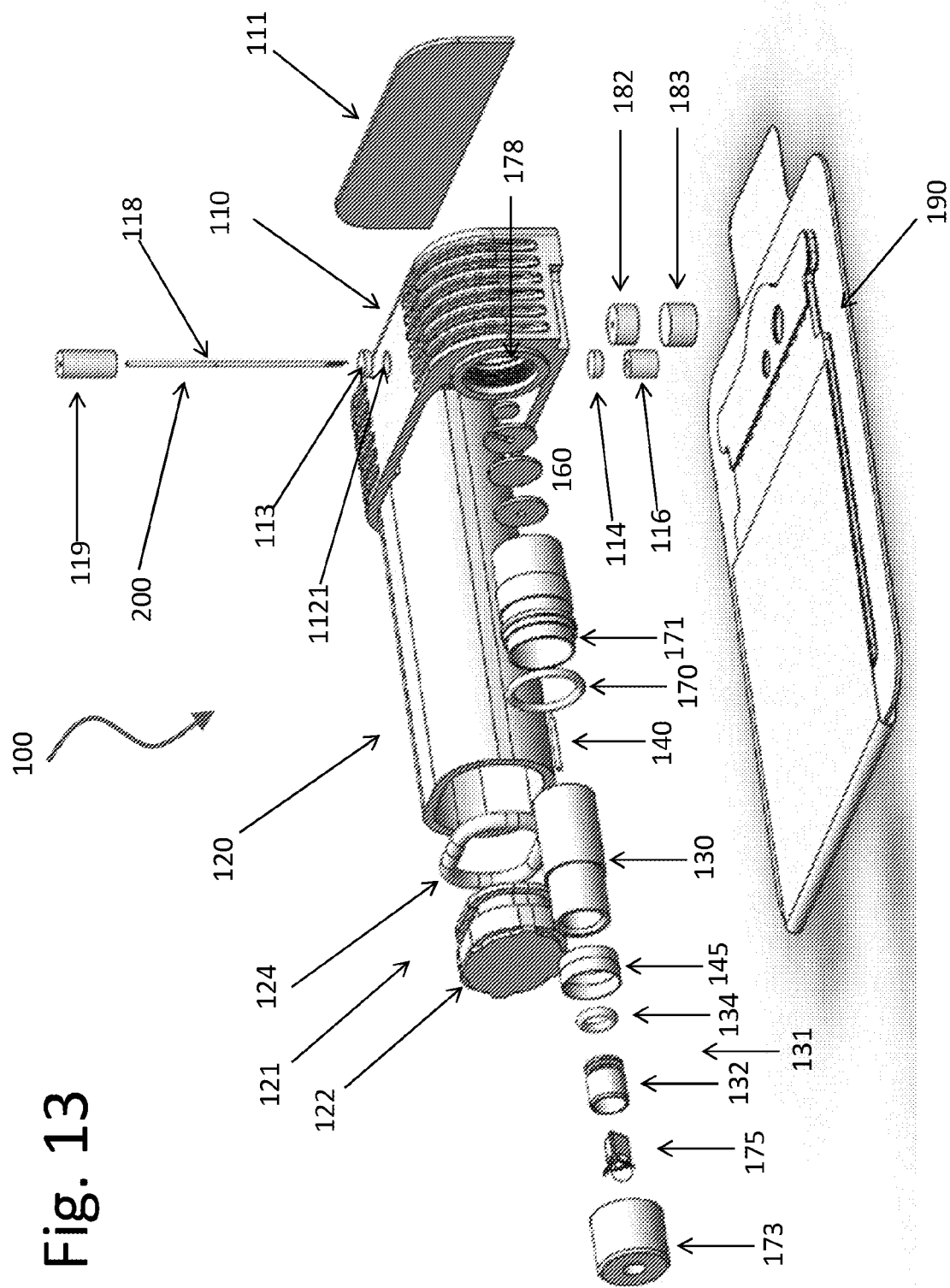
FIG. 13 shows an exploded spatial view of some of the components of the DP, according to some embodiments.

FIG. 13 shows an exploded spatial view of some of the components of the DP 100, according to some embodiments. The DP 100 includes a housing 110, a front foil 111, an opening (DP opening 178), and an adhesive base 190. A DP groove (upper end 1121 is shown) transverses the DP housing 110 and occupies the cannula 200 before and after cannula 200 insertion. The cannula 200 includes at least one opening 118 (hereinafter "cannula opening").

The DP grove includes a cannula spacer 119 (interchangeably "upper spacer" or "upper cannula spacer"), a top seal 113, a bottom seal 114, and a bottom spacer 116. The cannula opening 118 is positioned above the DP grove before insertion and within the DP groove after insertion. The filling port (bottom side, not shown) includes a filling septum 182 and a septum cover 183. The first reservoir 120 includes a plunger 121 that is comprised of a piston 122 and a gasket 124. The first reservoir has a shape of a cylinder, having a cross section that can be oval, elliptical, four arches, round, or any other symmetrical or nearly symmetrical configuration. In some embodiments, the plunger 121 may include more than one gasket 124 and/or may be comprised of one piece made of an air tight material (e.g., rubber, EPDM, bromobutyl and/or the like) that has at least one circumferential contact point with the first reservoir 120. The second reservoir (doser) 130 includes the second plunger (doser plunger) 131 that is comprised of a doser piston 132 and a doser gasket 134, a sticker 145 (a barcode for the doser sensor), a scraper spring 175 (reversible connector with the RP lead screw), and a sliding needle 140. The second reservoir 130 can be linearly displaced within the sleeve 171 that is connected to a sleeve cover 173 and a circumferential gasket, a DP-RP O-ring 170. The sleeve 171 is connected with the DP opening 178 by a screw-thread engagement, gluing, and/or welding.

Figure 14:
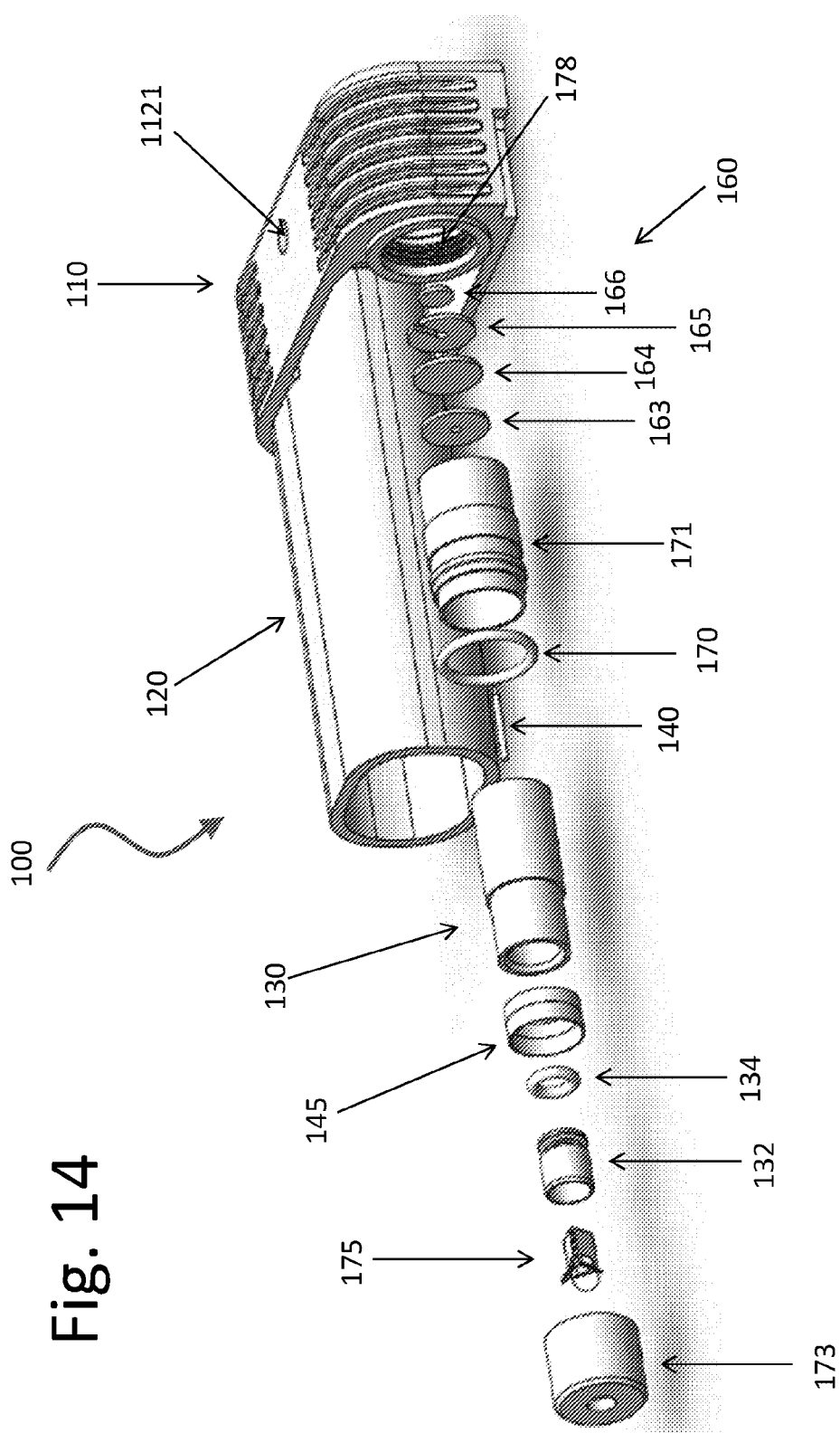
FIG. 14 shows an exploded spatial view of some of the components of the DP, according to some embodiments.

FIG. 14 shows an exploded spatial view of some of the components of the DP 100, according to some embodiments. The DP housing 110 includes the first reservoir 120, the upper end of the DP grove 1121, and the DP opening 178. The preassembled parts of the doser 130, sleeve, 171, and dual chamber valve mechanism 160 are shown from left to right as following: sleeve components—sleeve 171, sleeve cover 173, and DP-RP O-ring 170; doser components—doser 130, spring scraper 175, doser piston 132, doser plunger 134, doser sticker 145, and sliding needle 140; and dual chamber valve mechanism 160—front spacer 163, seal-4 164, back spacer 165, and seal-2 166.

Figure 15:
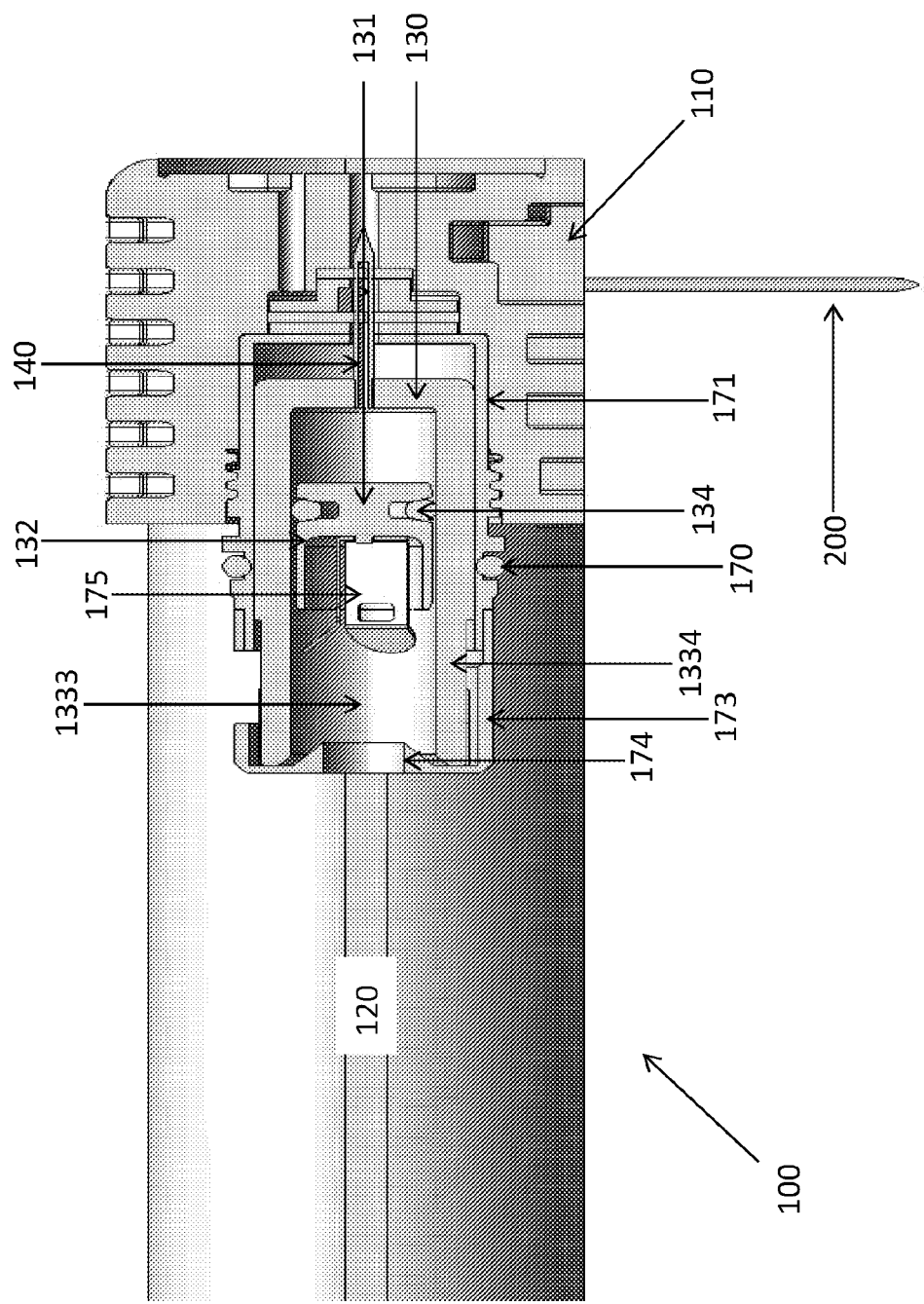
FIG. 15 shows a cross section longitudinal view of the assembled pump, according to some embodiments.

FIG. 15 shows a cross section longitudinal view (though the doser 130) of the assembled DP 100, according to some embodiments. The cannula 200 is connected to the DP housing 110. The doser 130 is comprised of the doser wall 1334, doser cavity 1333, and a sliding needle 140 that is in hydraulic communication with the doser cavity 1333. The doser plunger 131 is comprised of the doser piston 132, doser gasket 134, and scraper spring 175. The doser plunger 131 can be linearly displaced within the doser 130. The doser 130 can be linearly displaced within the sleeve 171 and the sleeve cover 173. The sleeve cover 173 includes a sleeve protrusion 174 that is engaged with the scraper spring 175 when the plunger 131 is in the proximal location (e.g., most proximal location). The DP-RPO ring 170 that encircles the sleeve 171 provides sealing of the RP sealed compartment after DP-RP connection.

Figure 16B:
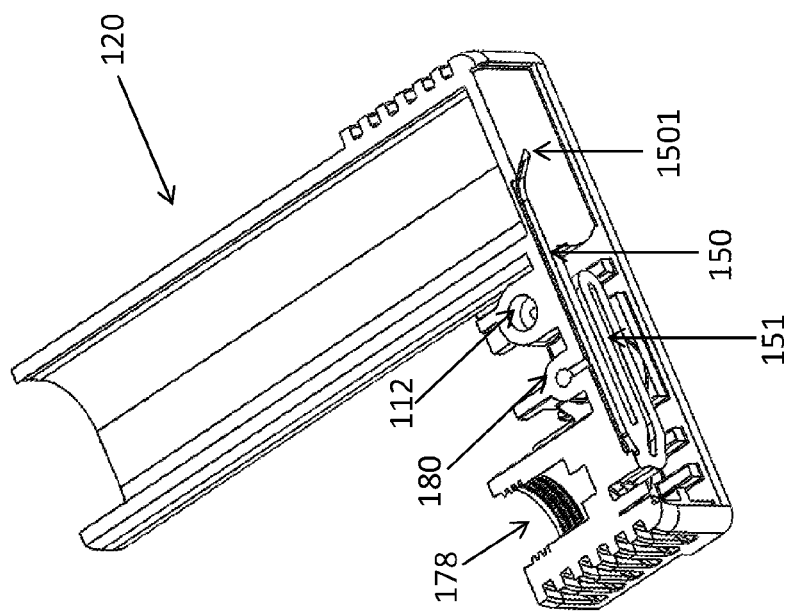
FIGS. 16A-B show longitudinal cross section views of the DP, according to some embodiments.
Figure 16A:
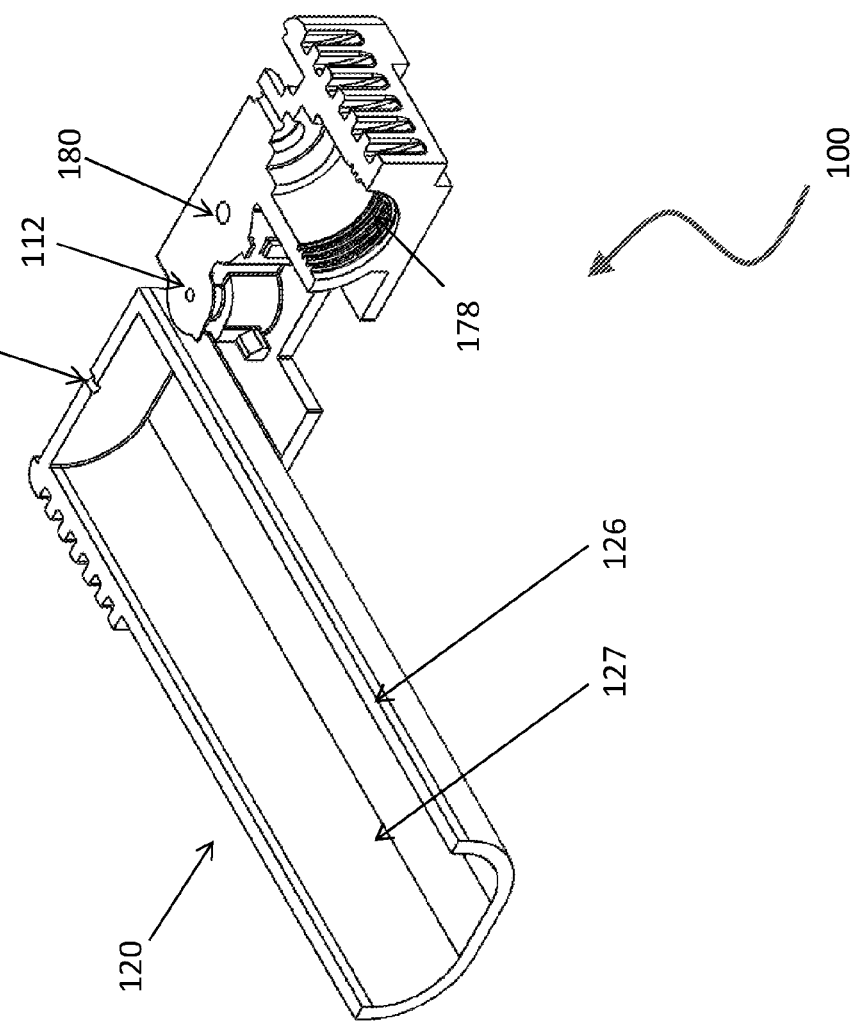

FIGS. 16A-B shows longitudinal cross section views of the DP 100 (rear view: FIG. 16A, front view: FIG. 16B), according to some embodiments. The first reservoir 120 is comprised of a reservoir wall 126, a cavity 127, and first conduit-first reservoir passage 1551. The DP housing 110 includes the DP cannula groove 112, the filling port 180, and the DP opening 178. FIG. 16B shows the first conduit 150, the second conduit 151 and the first conduit-first reservoir passage 1551.

Figure 17:
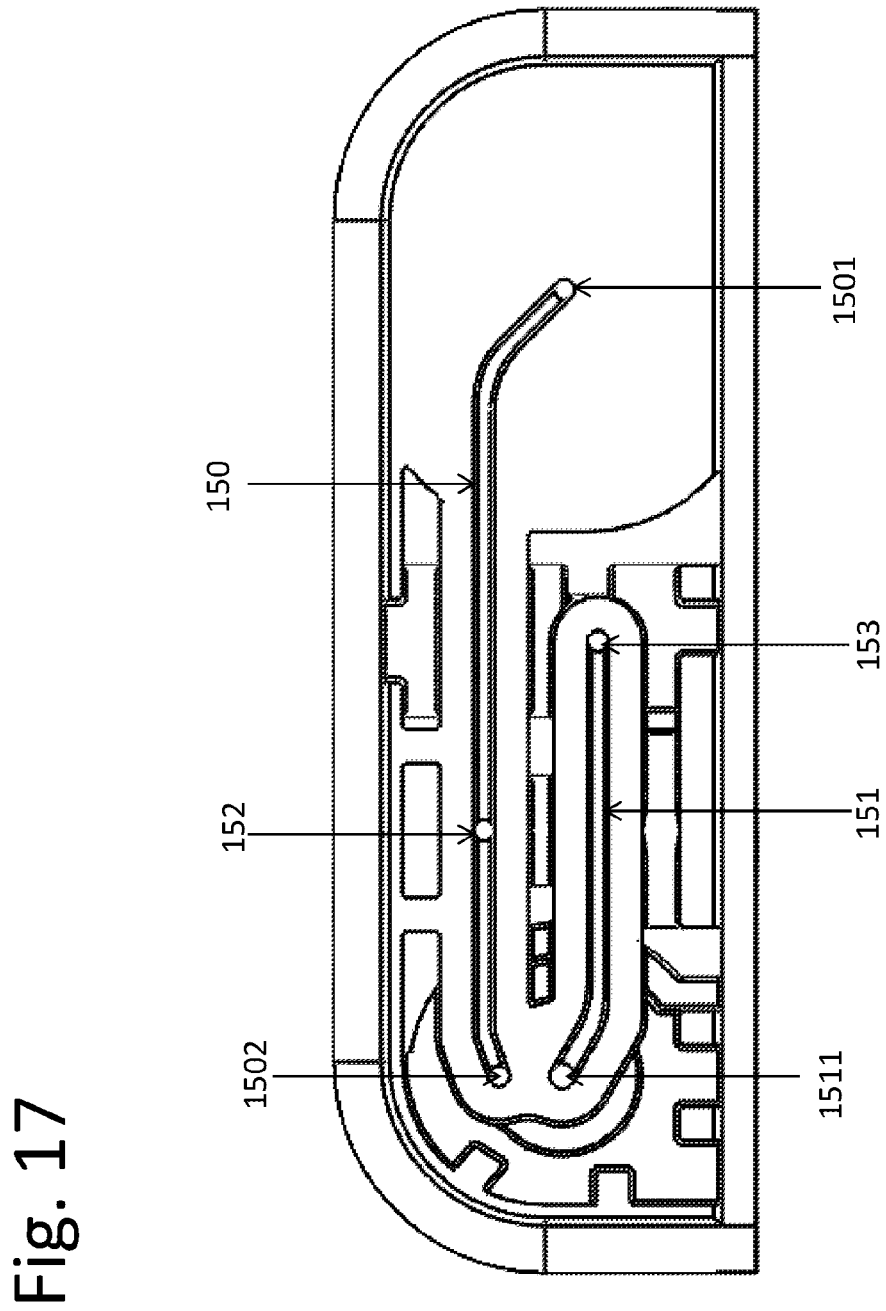
FIG. 17 shows a transverse cross section front view of the insulin delivery conduits, according to some embodiments.

FIG. 17 shows a transverse front view of the insulin delivery conduits, according to some embodiments. The first conduit 150 communicates between the first reservoir and the inlet chamber of the valve mechanism (FIGS. 59-62). The second conduit 151 communicates between the exhaust chamber of the valve mechanism and the exit port (well). During the doser filling phase (FIG. 55), insulin is delivered from the first reservoir via the first conduit-first reservoir passage 1501 and via the first conduit-inlet chamber passage 1502 into the inlet chamber. During the doser emptying phase (FIG. 56), insulin is delivered from the exhaust chamber via the exhaust chamber-second conduit passage 1511, via the second conduit 151, and via the delivery conduit 153 into the exit port. A filling conduit 152 communicates between the filling port and the first conduit 150. During first reservoir filling, fluid such as insulin can be delivered via the filling conduit 152, via the first conduit 150 and through the first conduit-first reservoir passage 1501 into the first reservoir.

Figure 18A:
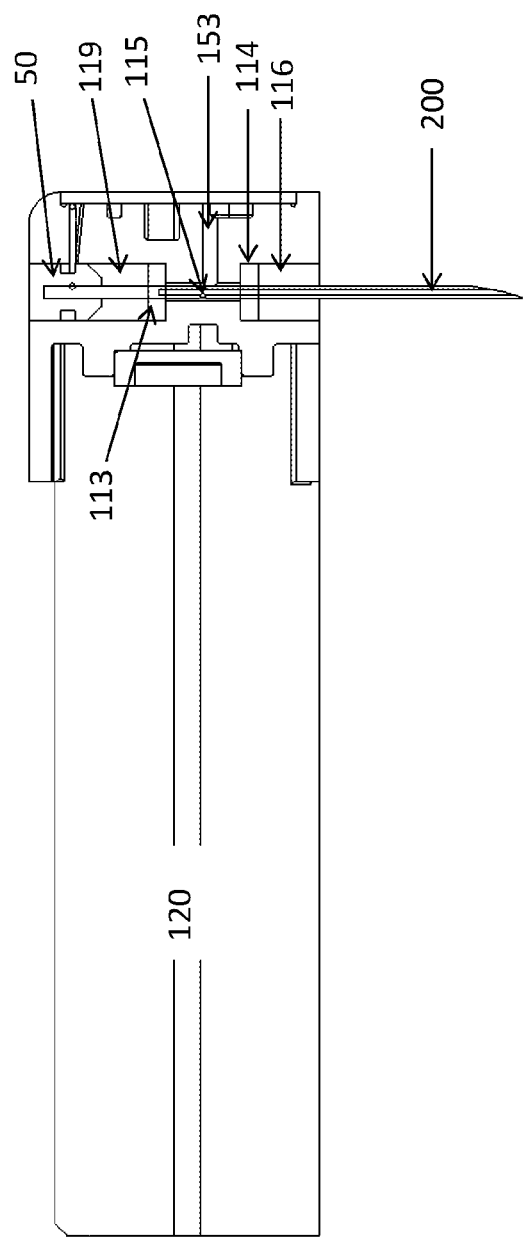
FIGS. 18A-B show longitudinal cross section views through the DP cannula groove and exit port and through the filling port, according to some embodiments.
Figure 18B:
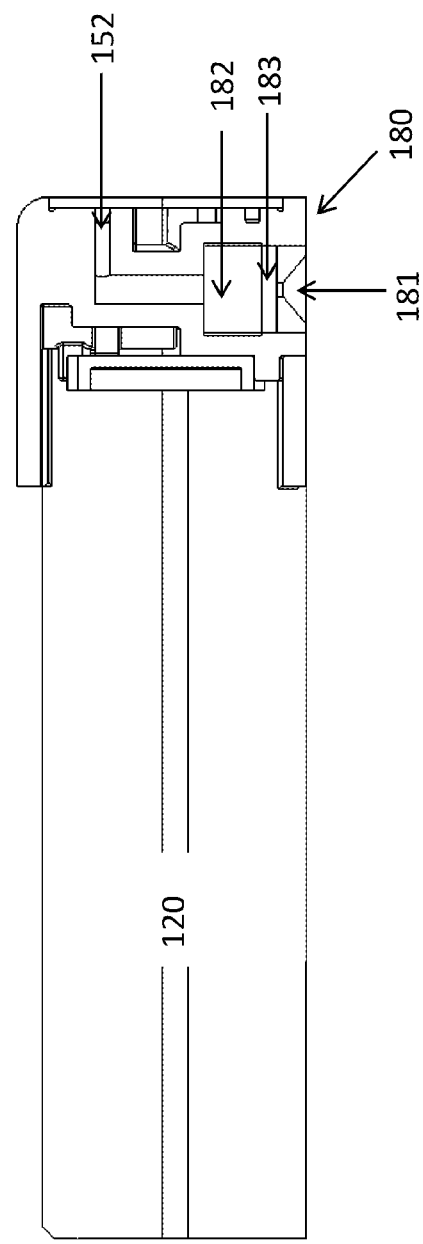

FIG. 18A-B show longitudinal cross section views through the DP cannula groove and exit port (FIG. 18A) and through the filling port (FIG. 18B), according to some embodiments. FIG. 18A shows the cannula 200, cannula cap 50, cannula spacer 119, upper seal 113, bottom seal 114, and bottom spacer 116. Insulin is delivered through the delivery conduit 153 into the well 115 and from the well 115 through the cannula 200 into the patient. FIG. 18B shows the filling port 180 that includes the filling aperture 181, filling septum 182, and septum cover 183. During first reservoir filling, a syringe needle (FIG. 5) is introduced through the filling septum 182 and insulin is delivered via the filling conduit 152 to the first reservoir (via the first conduit).

FIGS. 19A-D show spatial views (FIG. 19A and FIG. 19B) and longitudinal cross sectional views (FIG. 19C and FIG. 19D) of the DP 100 before (FIG. 19A and FIG. 19C) and after (FIG. 19B and FIG. 19D) cannula 200 insertion, according to some embodiments. The DP includes a DP housing 110, first reservoir 120, doser 130, adhesive base 190 (covers with liner 197), and the upper end of the DP cannula groove 1121. Before cannula 200 insertion, the cannula cap 50 is situated above the DP housing 110. After insertion, the cannula cap 50 is aligned with the top side DP housing 110.

FIGS. 20A-B show longitudinal cross section views through the DP cannula grove 112 and filling conduit 153, before (FIG. 20A) and after (FIG. 20B) cannula 200 insertion, according to some embodiments. The DP cannula groove 112 (dashed line rectangular) includes a cannula spacer 119, a top seal 115, a well 115, a bottom seal 114, and a bottom spacer 116. The cannula 200 includes a cannula cap 50, a cannula opening 118, and a cannula tip 117. Before cannula 200 insertion, the cannula cap 50 and cannula opening 118 are situated above the DP groove 112. After cannula 200 insertion, the cannula cap 50 resides within the DP groove 112 and the cannula opening 118 resides within the well 115.

FIGS. 21A-D show longitudinal cross section views of the DP groove, according to some embodiments. FIG. 21A shows the DP groove upper end 1121, the DP groove lower end 1122, the upper seal 113, and the lower seal 114. Both upper seal 113 and lower seal 114 are shaped as coins and are made of a flexible elastomer (e.g., rubber, silicone, etc.). The well 115 is a sealed compartment in fluid communication with the delivery conduit 153. FIG. 21B shows the cannula spacer 119 and lower spacer 116. Both spacers are shaped as cylinders that are made of a flexible elastomer (e.g., rubber, silicone, etc.). FIG. 21C and FIG. 21D show the cannula 200 within the DP groove before (FIG. 21C) and after (FIG. 21D) insertion. The cannula 200 includes the cannula cap 50 and cannula opening 118.

Figure 22B:
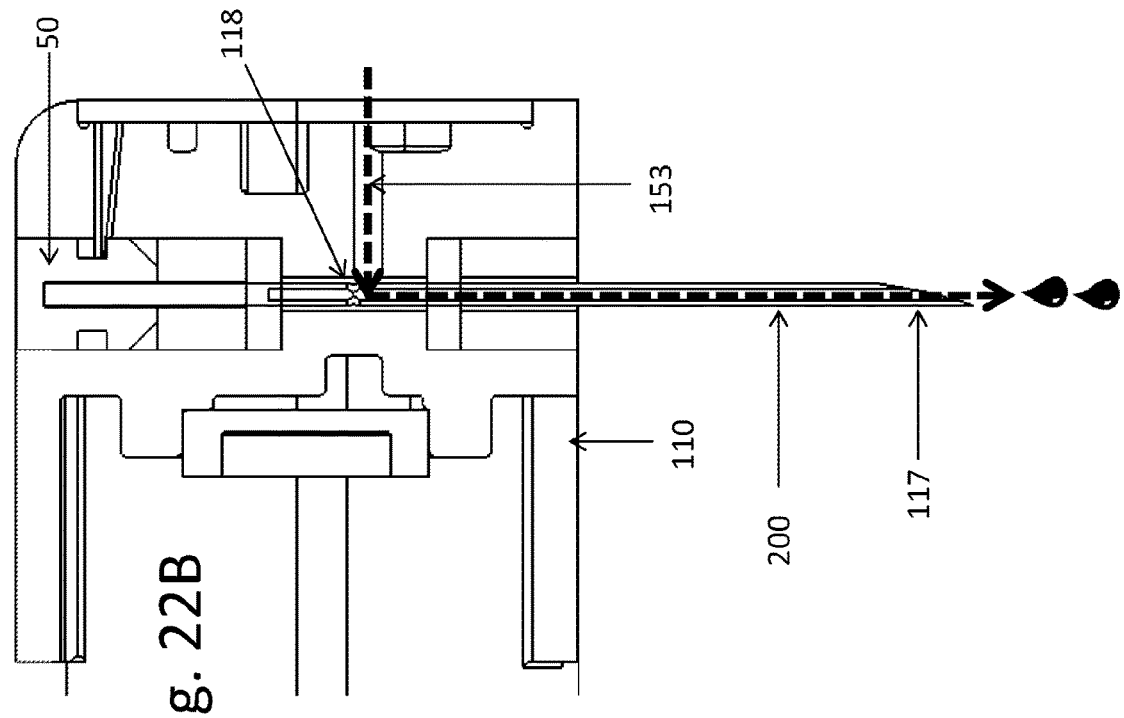
FIGS. 22A-B show cross section views of the DP groove during priming and operation, according to some embodiments.
Figure 22A:
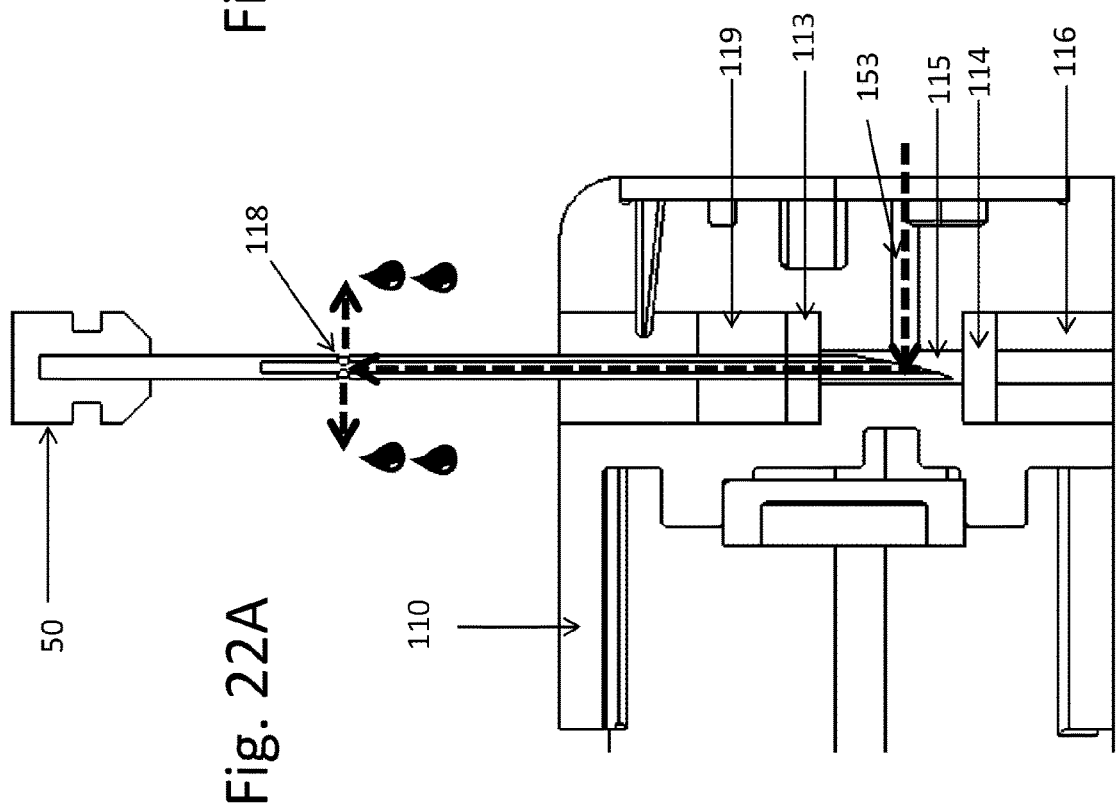

FIGS. 22A-B show cross sectional views of the DP groove during priming (FIG. 22A) and operation (FIG. 22B), according to some embodiments. The DP grove includes the cannula spacer 119, top seal 113, bottom seal 114, bottom spacer 116, and well 115. The well 115 is in hydraulic communication with the filling conduit 153. The cannula 200 includes the cannula cap 50, cannula opening 118, and cannula tip 117. During priming (FIG. 22A), the cannula tip 117 is situated within the well 115 and the cannula opening 118 and cannula cap 50 are situated above the DP housing 110. Insulin is delivered through the delivery conduit 153 into the well 115 and from the well 115 via the cannula 200 into the opening 118. Priming is done when the patch pump is in the upright position. Priming is continuing until insulin drops are seen emerging from the cannula opening 118 and there is no residual air in the system. During pump operation (FIG. 22B), the cannula opening 118 is situated within the well 115 and the cannula tip 117 is situated below the DP housing 110. Insulin is delivered through the delivery conduit 153 into the well 115 and from the well 115 via the cannula 200 into the cannula tip 117 and the patient's body.

Figure 23:
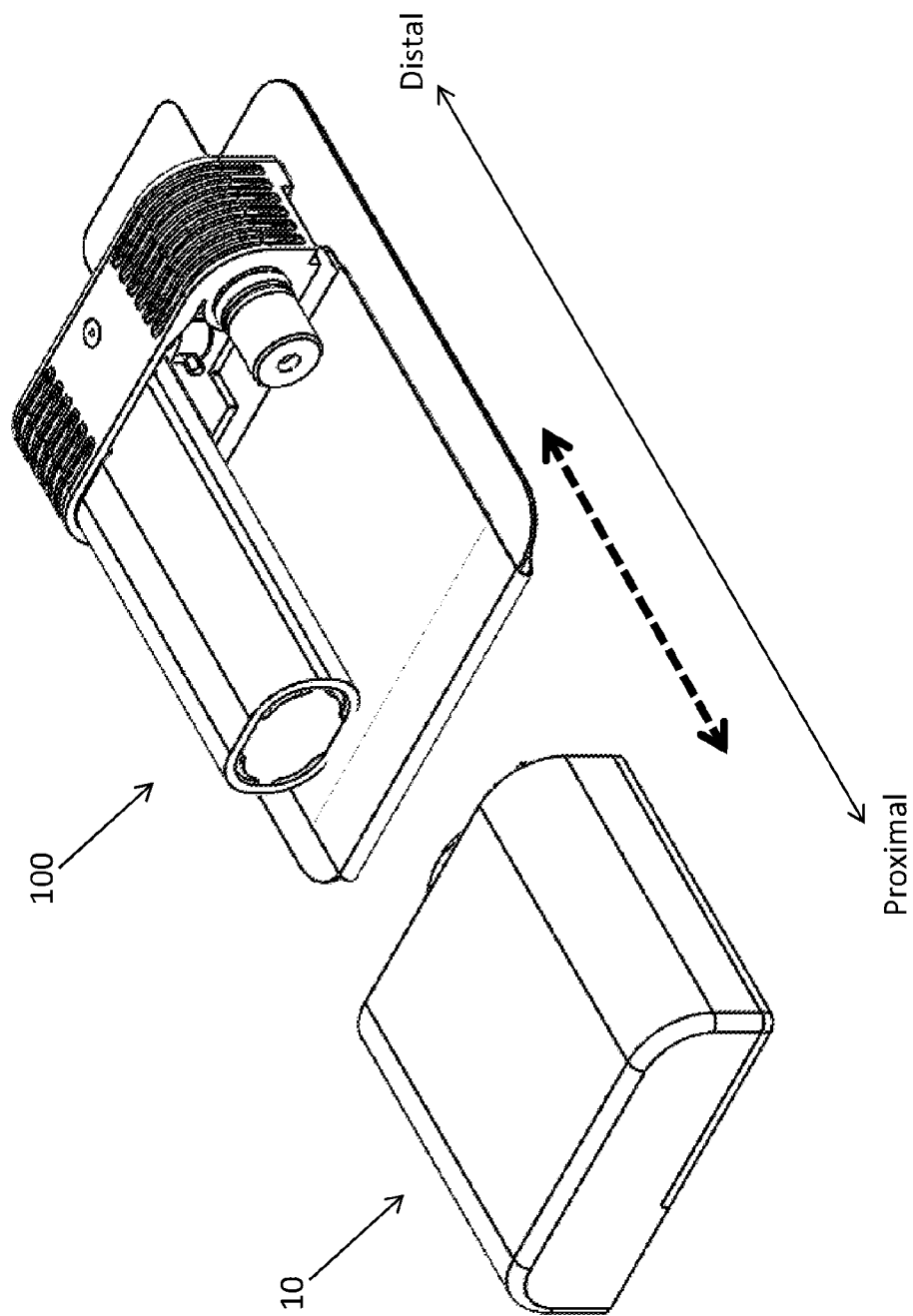
FIG. 23 shows spatial views of the RP and DP, according to some embodiments.

FIG. 23 shows spatial views of the RP 10 and DP 100, according to some embodiments. The bold double-arrow dashed line shows the direction of RP-DP connection and disconnection. The light-double arrow line shows the proximal and distal directions of the patch pump parts and components.

FIGS. 24A-B show planar cross sectional views of the patch pump 1, according to some embodiments. The patch pump I may include the first reservoir 120, second reservoir 130, driving mechanism 40, valve mechanism 160, battery 80, motor 42, and adhesive base 190. The dashed line (FIG. 24A) shows the boundaries of the RP sealed compartment.

Figure 25:
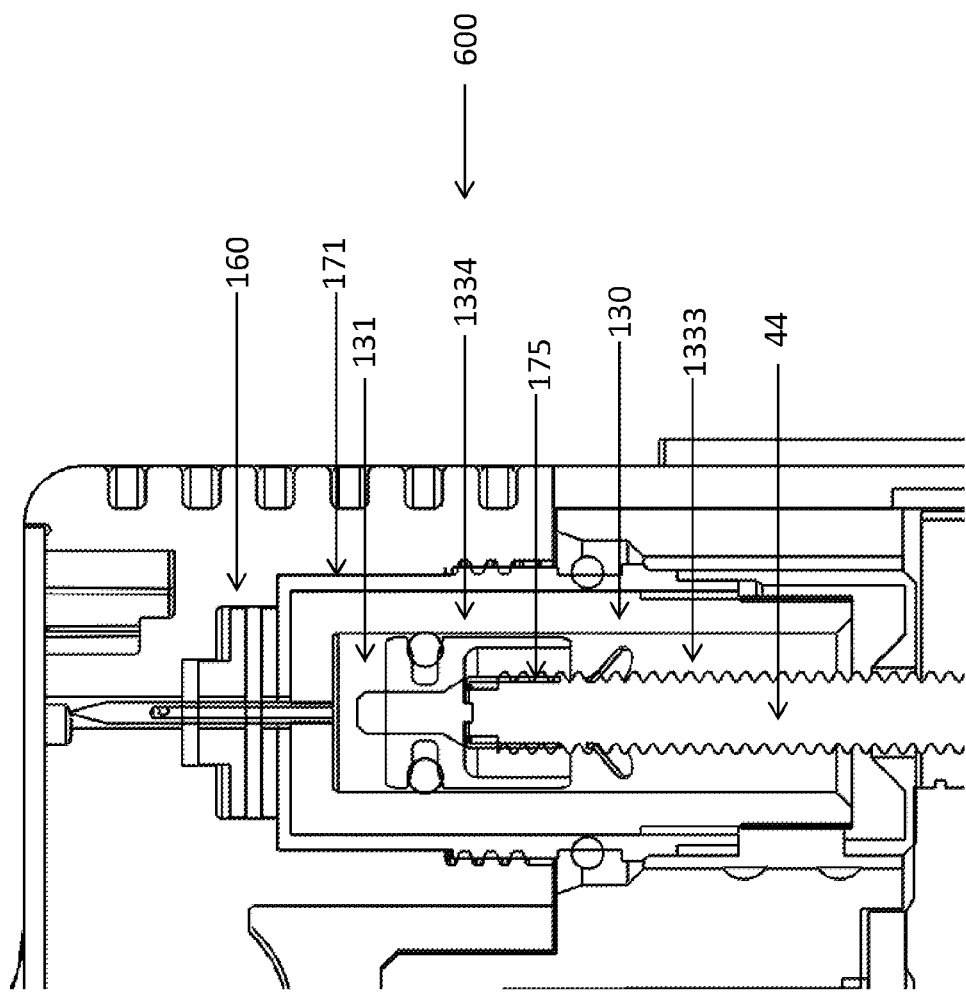
FIG. 25 shows a scheme of the RP-DP interface after RP-DP connection and the pumping mechanism, according to some embodiments.

FIG. 25 shows a scheme of the RP-DP interface after RP-DP connection and the pumping mechanism 600, according to some embodiments. In some embodiments, the pumping mechanism 600 includes the RP lead screw 44 and the DP doser 130, valve mechanism 160, doser plunger 131, and scraper spring 175. Such instances may include embodiments where the pumping mechanism 600, or at least a part thereof, is included in the RP only, in the DP only, or in both the RP and the DP. In some embodiments, the doser 130 is comprised of a wall 1334 and a cavity 1333. The doser plunger 131 is rigidly connected to the scraper spring 175. The lead screw 44 is reversibly connected to the scraper spring 175.

Figure 26A:
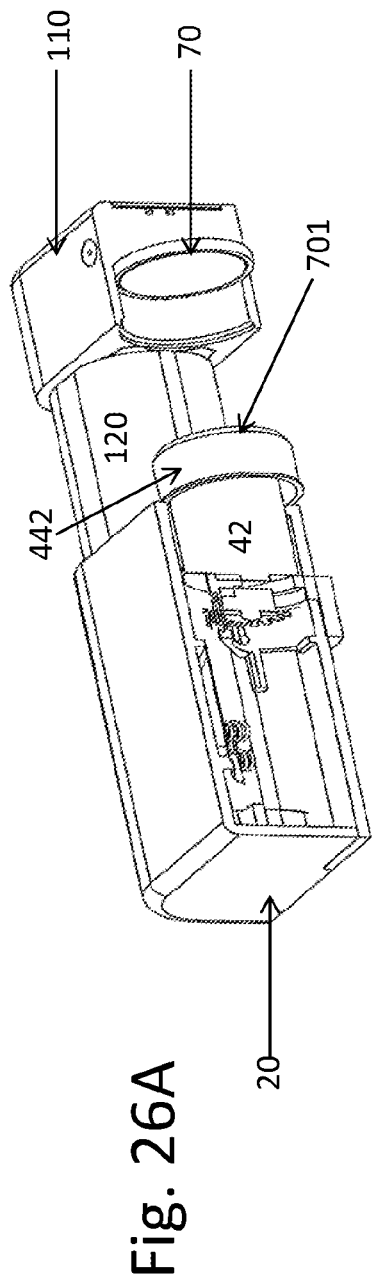
FIGS. 26A-C show spatial and cross section view of the magnet and iron plate before RP-DP connection and after RP-DP connection, according to some embodiments.
Figure 26B:
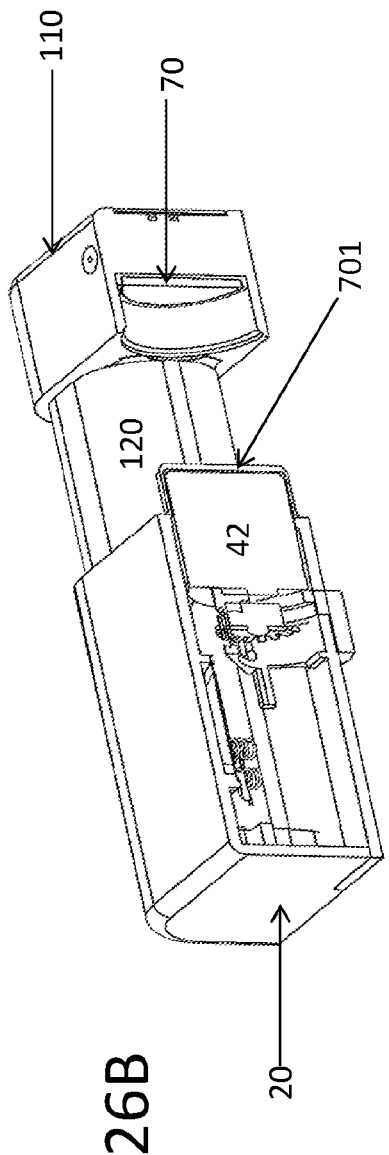
Figure 26C:
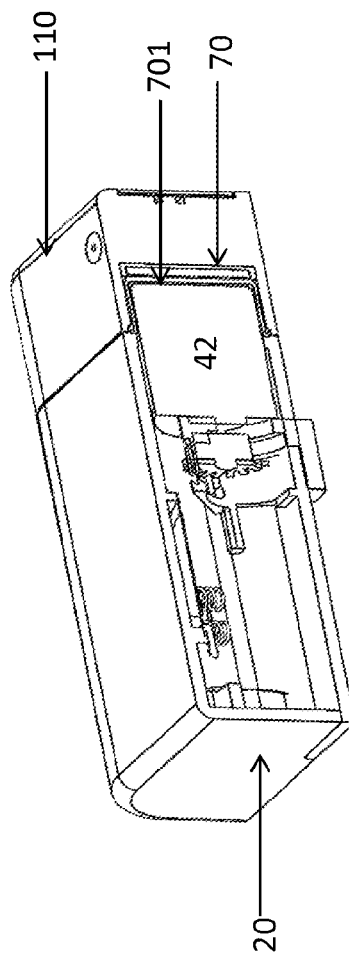

FIGS. 26A-C show spatial (FIG. 26A) and cross section view (FIG. 26A and FIG. 26B) of the magnet 70 and iron plate 701 before RP-DP connection (FIG. 26A) and after RP-DP connection (FIG. 26B and FIG. 26C), according to some embodiments. The magnet 70 provides removable firm connection between the RP housing 20 and the DP housing 110. The magnet 70 is rigidly connected to the DP housing 110 and the iron plate is rigidly connected to the motor cover 442 which covers the motor 42. After RP-DP connection the magnet 70 and iron plate 701 are touching each other. The magnet 70 and iron plate 71 can be interchangeably replaced in positions.

Figure 27B:
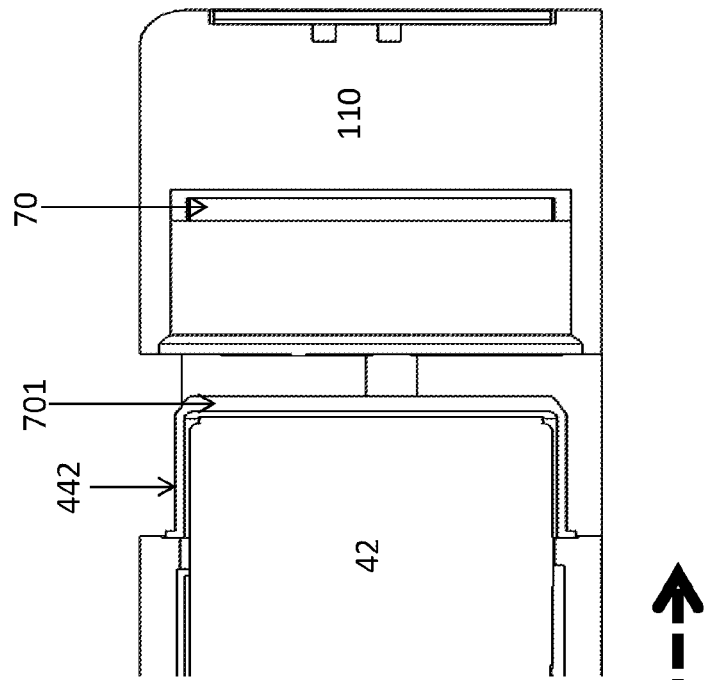
FIGS. 27A-B show magnified schemes of the magnet and iron plate before and after RP-DP disconnection, according to some embodiments.
Figure 27A:
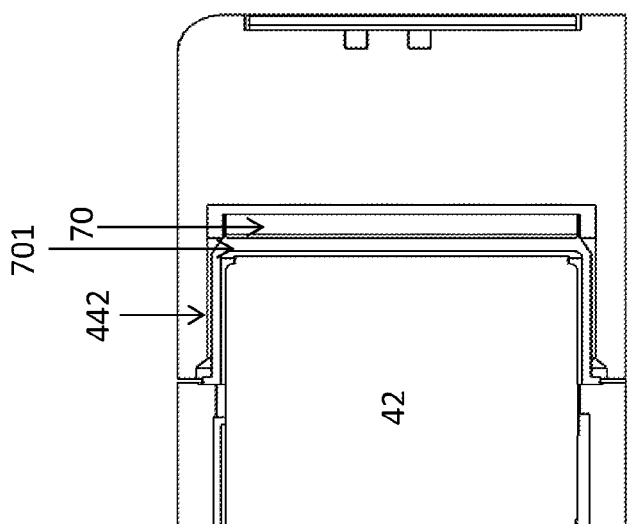

FIGS. 27A-B show magnified schemes of the magnet 70 and iron plate 701 before (FIG. 27A) and after (FIG. 27B) RP-DP disconnection, according to some embodiments. The iron plate 701 is rigidly connected to the motor cover 442 and the magnet 70 is rigidly connected to the DP housing 110. The dashed arrow shows the direction of movement during disconnection.

FIG. 28 shows a spatial view of the adhesive base 190, according to some embodiments. The adhesive base 190 is comprised of the flex base 191, bend line 196, filling aperture 181, and cannula aperture 193. The flex base 191 includes two adhesive surfaces (showed in dashed arrows)—upper adhesive surface 194 and bottom adhesive surface 195. Both adhesive surfaces (194 and 195) are covered with a folded liner 197. The liner 197 can be removed by grasping the liner flange 198 and peeling the liner 197 from the bottom 195 and upper 194 adhesive base surfaces. The flex based 191 can be folded at the pivot bend line 196. The adhesive base upper surface 194 provides a removable firm connection between the DP and RP. The adhesive base bottom surface 195 provides a removable firm connection between the patch pump and the skin.

Figures 29A, 29B:
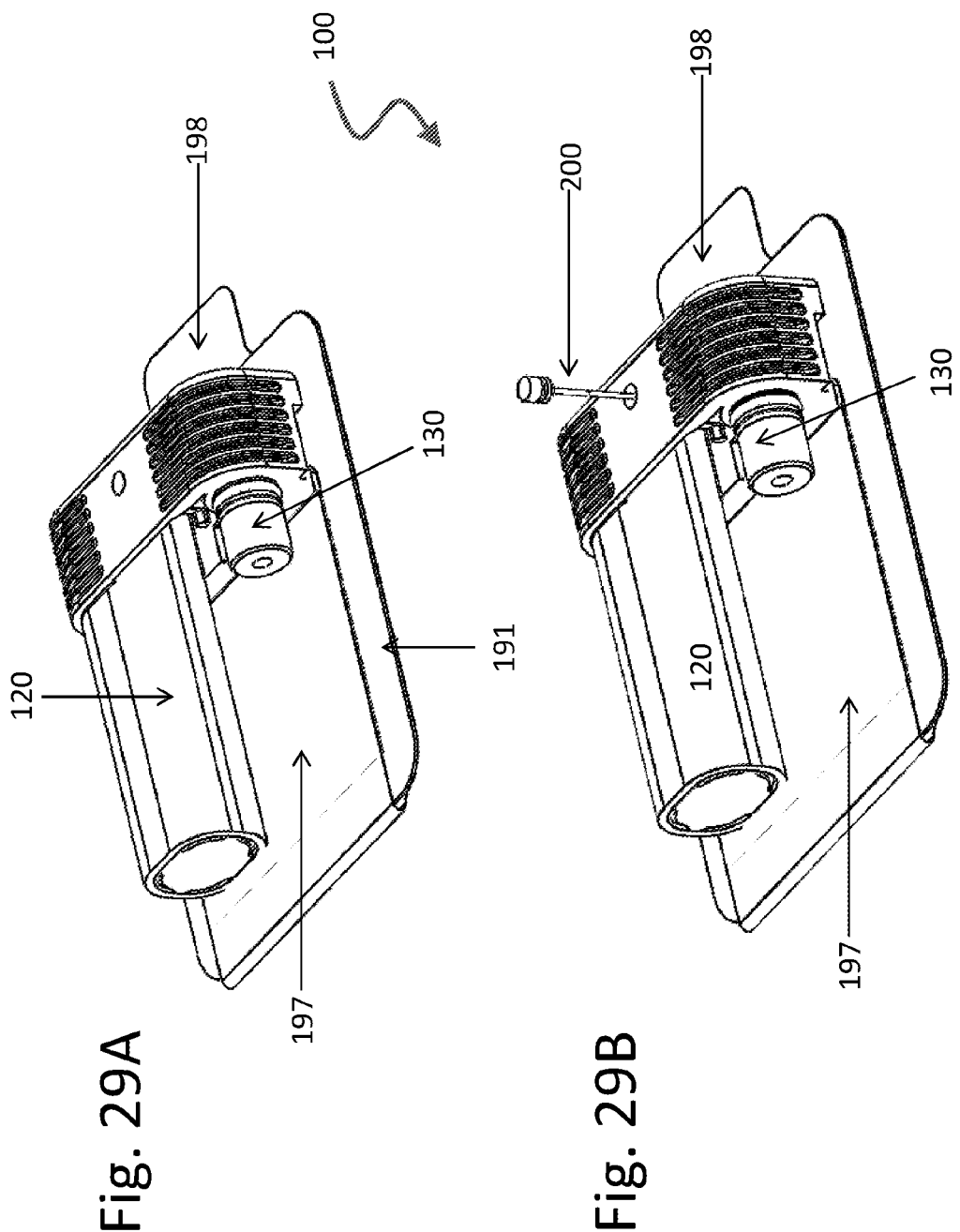
FIGS. 29A-B show spatial views of the DP without (FIG. 29A) and with (FIG. 29A) the cannula (before insertion), according to some embodiments.
Figure 31C:
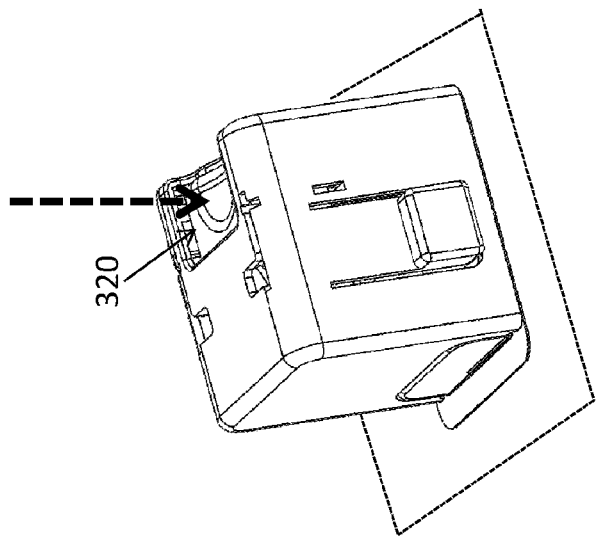
Figure 31B:
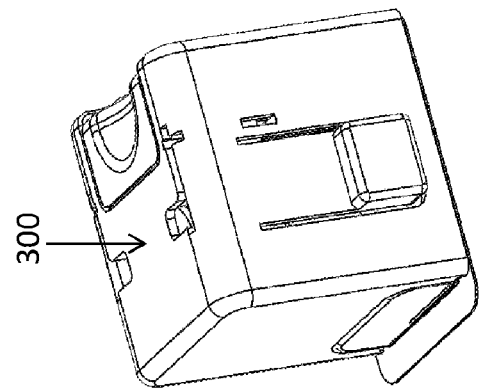
FIG. 31B shows the inserter and patch pump (partially concealed) after complete removal of liner removal;
shows the inserter on the skin (square in dashed light line), the adhesive base bottom surface is adhered to the skin, and the trigger is pressed (dashed bold line arrow) for FIG. 31C cannula insertion.
Figure 31A:
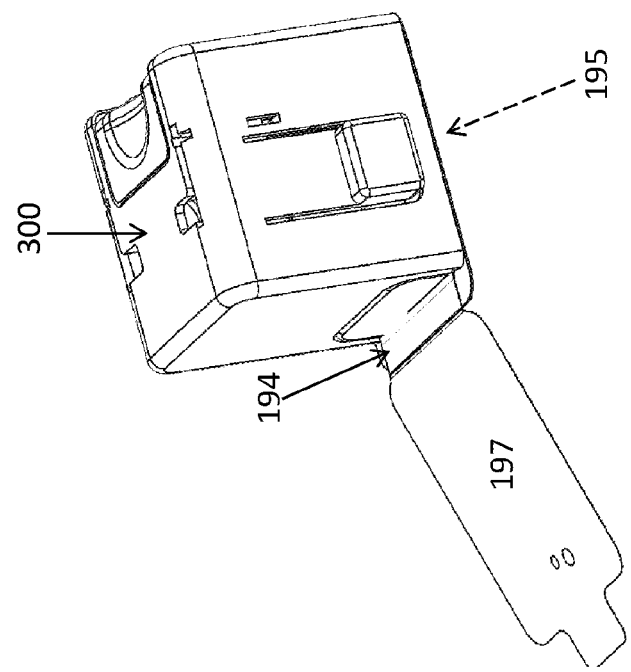
FIG. 31A shows a next stage of liner peeling.

FIGS. 29A-B show spatial views of the DP 100 without (FIG. 29A) and with (FIG. 29B) the cannula 200 (before insertion), according to some embodiments. The DP 100 includes the first reservoir 120, doser 130, flex base 191, liner 197, liner flange 198, and cannula 200.

FIGS. 30-34 show sequential processes of the patch pump handling including RP-DP connection, liner removal, cannula insertion, patch pump removal, flex base folding, and RP-DP disconnection, according to some embodiments. For example, in some embodiments, FIGS. 30A-D and 31A-C show spatial views of the patch pump I handling including RP-DP assembly, liner peeling, skin adhesion, and cannula insertion. FIG. 30A shows the assembled inserter 300 with the DP (reservoir 120 is shown) which is attached to the bottom side of the inserter (see details in FIGS. 35-43). The liner 197 covers both sides of the adhesive base 190 (concealed, presented in dashed line). FIG. 30B shows the insertion of the RP 10 into the inserter 300 in the direction of the dashed arrow. FIG. 30C shows the RP 10 within the inserter 300 (RP and DP are connected). Liner 197 peeling is initiated by grasping the liner flange 198. FIG. 30D shows the liner 197 peeling in process, the liner 197 is partial removed from the adhesive base lower surface (concealed). FIG. 31A shows the next stage of liner 197 peeling, the liner 197 is removed from the adhesive base bottom surface 195 (concealed, showed in dashed line) and still covers the adhesive base upper surface 194. FIG. 31B shows the inserter 300 and patch pump (partially concealed) after complete removal of liner 197 from both adhesive base surfaces (194 and 195). At this stage, the adhesive base upper surface 194 adheres to the RP and provides removable firm connection between the RP and DP. FIG. 31C shows the inserter 300 on the skin (square in dashed light line), the adhesive base bottom surface is adhered to the skin, and the trigger 320 is pressed (dashed bold line arrow) for cannula insertion.

Figure 32C:
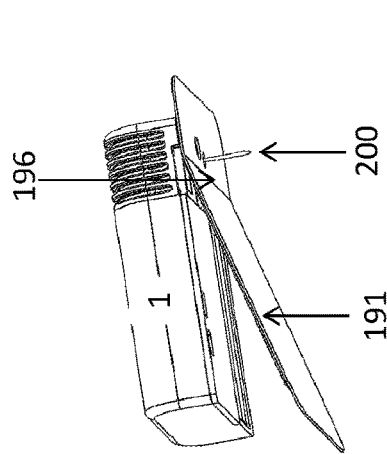
FIG. 32C shows the initiation of the flex base folding.
Figure 32B:
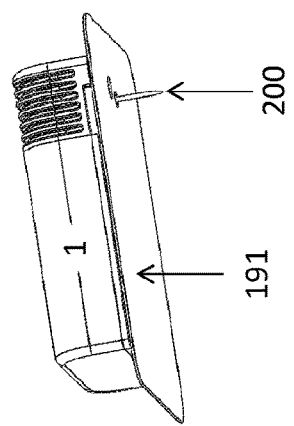
FIG. 32A and FIG. 32B show a patch pump, a cannula, and a flex base after patch pump removal from skin
Figure 32A:
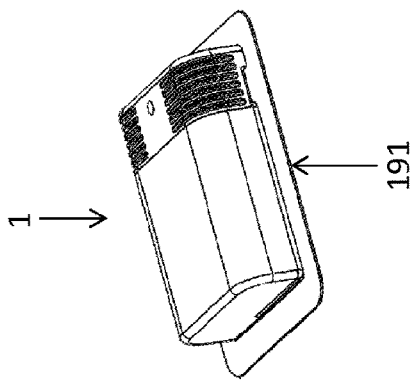
Figure 32F:
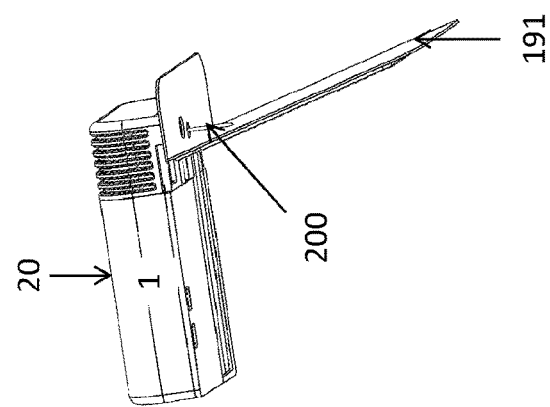
FIGS. 32D-F show further folding of the flex base.
Figure 32E:
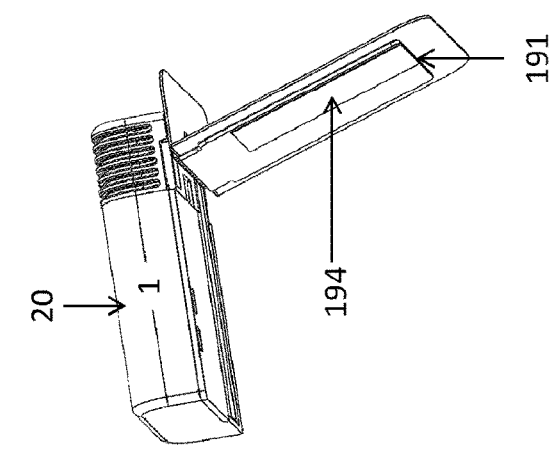
Figure 32D:
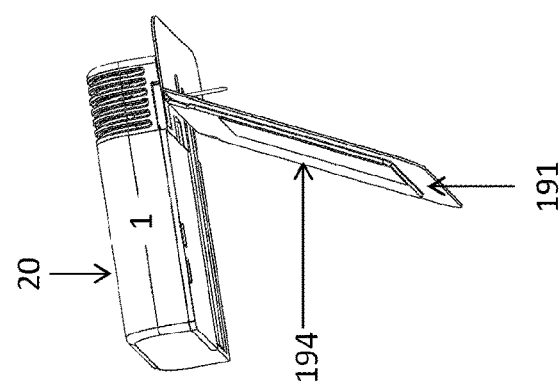
Figure 33A:
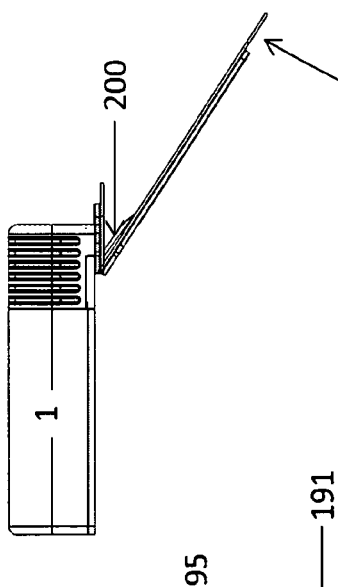
FIGS. 33A-E show further folding of the flex base.
Figure 33B:
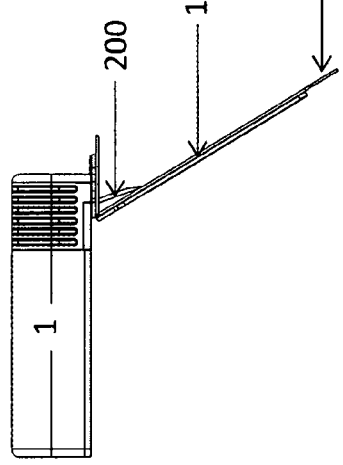
Figure 33C:
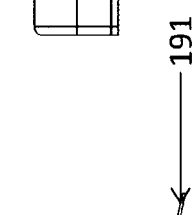
Figure 33D:
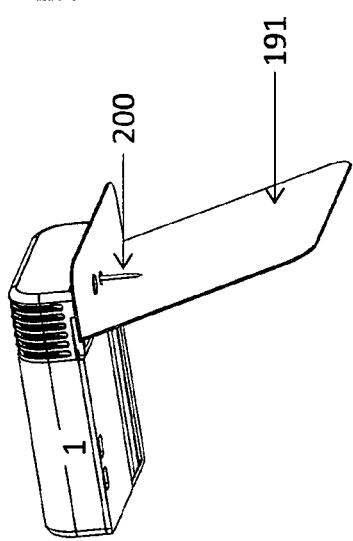
Figure 33E:
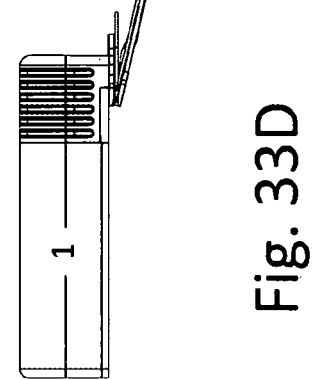
Figure 34A:
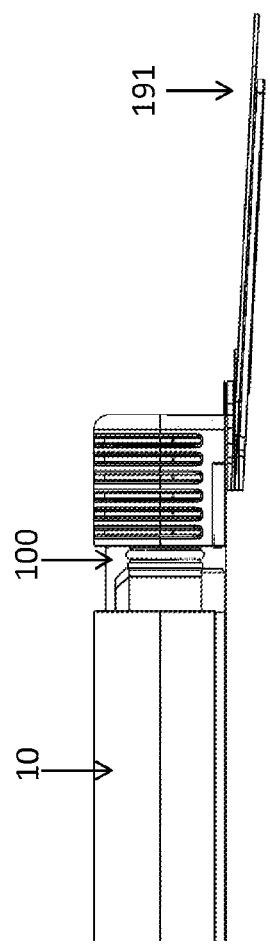
FIGS. 34A-C show longitudinal cross section views of DP-RP disconnection stages, and more specifically, FIGS. 34A-B showing disconnection of the RP from the DP, 100 (direction of bold dashed line arrow), and FIG. 34C showing RP recharging and disposal of DP.
Figure 34B:
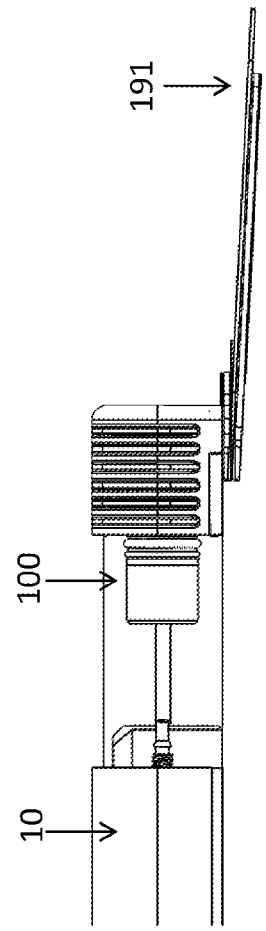
Figure 34C:
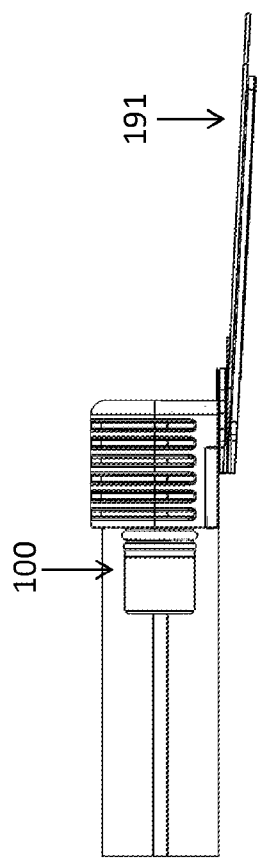

FIGS. 32A-F, FIGS. 33A-E, and FIGS. 34A-C show spatial and cross sectional views of pump handling after removal from the patient skin, according to some embodiments. FIG. 32A and FIG. 32B show the patch pump 1, the cannula 200, and the flex base 191 after path pump I removal from skin. FIG. 32C shows the initiation of the flex base 191 folding—the adhesive base bottom surface 195 is folded in the direction of the cannula 200, pivoting around the bend line 196. FIGS. 32D-F show further folding of flex base 191, the adhesive base upper surface 194 is getting away from the RP housing 20. FIGS. 33A-E show further folding of the flex base 191 and banding the cannula 200. Upon completion of flex base 191 folding, the adhesive base bottom surface 195 covers the banded cannula 200, the cannula 200 is concealed, and the user is protected from inadvertent self-pricking. FIGS. 34A-C show longitudinal cross section views of DP-RP disconnection stages after completion of flex base 191 folding. The RP 10 is disconnected from the DP 100 (direction of bold dashed line arrow) (FIGS. 34A-B). After RP-DP disconnection (FIG. 34C) the RP is recharged and the DP is disposed.

Figure 35:
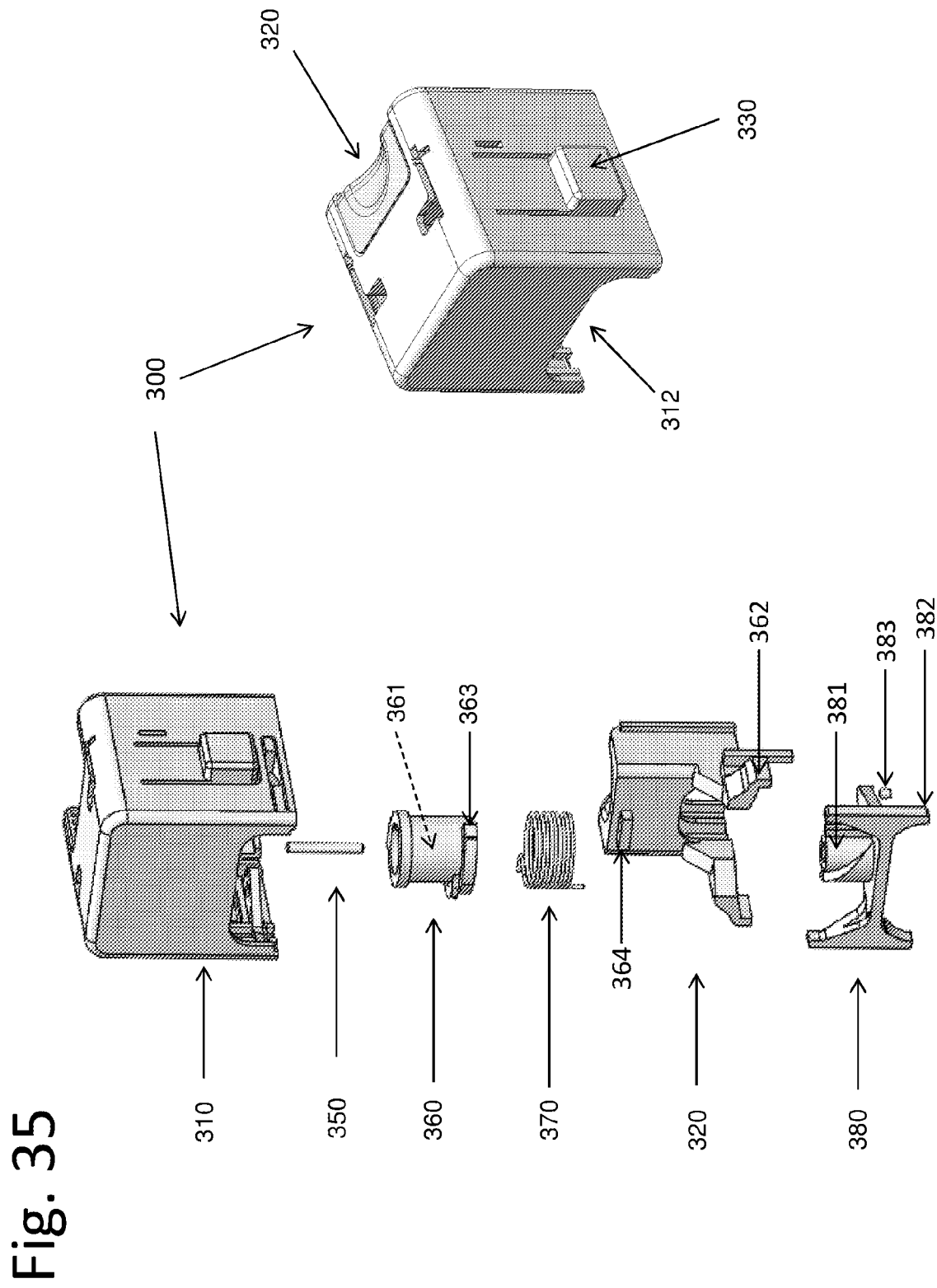

FIGS. 35-44 show the inserter 300, inserter activation, and inserter operation including inserter components, mechanism of action, and user interface, according to some embodiments. In some embodiments, the inserter 300 is provided preloaded. The inserter 300 provides one or more of the following functions: 1—alignment of RP and DP during RP-DP connection, 2—patch pump holder during filling, priming, and skin adhesion, and 3—semi automatic cannula insertion (upon trigger press). After cannula insertion, the inserter 300 is automatically released from the patch pump and disposed. For example, in some embodiments, FIG. 35 shows spatial views of the main components of the inserter 300. The inserter comprises a housing 310, RP notch 312, trigger 320, and two safety catches 330 at both sides of the inserter housing 310. The RP notch provides access to the RP during RP-DP connection. The insertion mechanism 341 and releasing mechanism 340 include the pivoting rod 350, inserter rotating nut 360, inserter spring 370, trigger 320, and inserter hammer 380. The trigger 320 includes the trigger stopper 362, and inserter rotating nut stopper 364. The inserter rotating nut 360 includes a rotating thread 361 (concealed, dashed line arrow), and a splitter 363. The inserter hammer 380 includes a hammer linear thread 381, a hammer lead 382, and a cannula pusher 383. When the inserter components are assembled, in some embodiments, the rotating thread 361 is engaged with the hammer linear thread 381. Pressing both safety catches 330 release the trigger stopper 362 and allows downward movement of the trigger 320 with concomitant trigger 320 press. Downward movement of the trigger 320 and the inserter rotating nut stopper 364 allows free rotation of the inserter spring 370 and the inserter rotating nut 360. The stored energy in the pre-loaded inserter spring 370 rotates the inserter rotating nut 360, the rotating thread 361, and the splitter 363. Rotation of the inserter rotating nut 361 is converted to downward linear displacement of the hammer 380 and the cannula pusher 383, and consequently, cannula insertion into the body. Rotation of the splitter 363 is converted to lateral linear displacement of the DP holders (311, not shown in FIG. 35), providing freely inserter 300 release after cannula insertion.

FIGS. 36A-B show spatial views of the inserter 300, according to some embodiments. The inserter 300 includes the housing 310, trigger, 320, safety catches, RP notch 312, and viewing window 390. The viewing window 390 provides line of sight for observing insulin drops during patch pump priming.

FIGS. 37A-C show spatial views of the insertion mechanism, according to some embodiments. The insertion mechanism includes the trigger 320, inserter spring 370, inserter rotating nut 360, pivoting rod 350, and hummer 380. The trigger 320 includes the trigger stopper 362 (at both sides) and the inserter rotating nut stopper 364. The inserter rotating nut 360 includes the rotating thread 361 and the splitter 363. The hammer includes the hammer lead 382 (both sides), and cannula pusher 383. FIG. 37A and FIG. 37B show the insertion mechanism before pressing the trigger 320. FIG. 37C shows the insertion mechanism after trigger 320 is press in the direction of the bold dashed arrow. The inserter rotating nut stopper 364 is linearly displaced in the direction of the bold dashed arrow and the inserter rotating nut 360 is free to rotate around the pivoting rod 350.

Figure 38B:
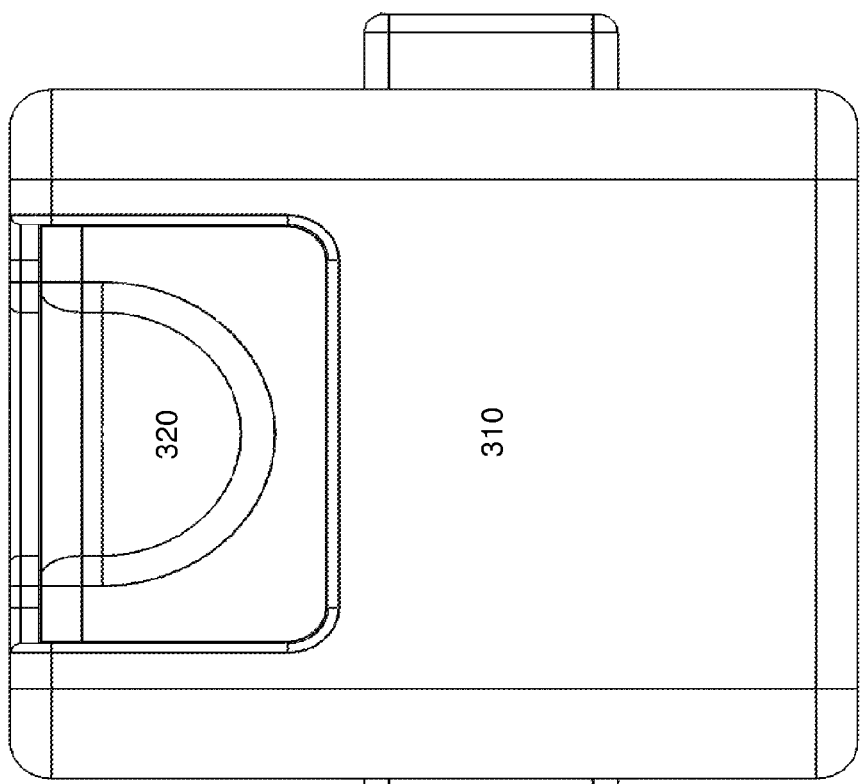
Figure 38A:
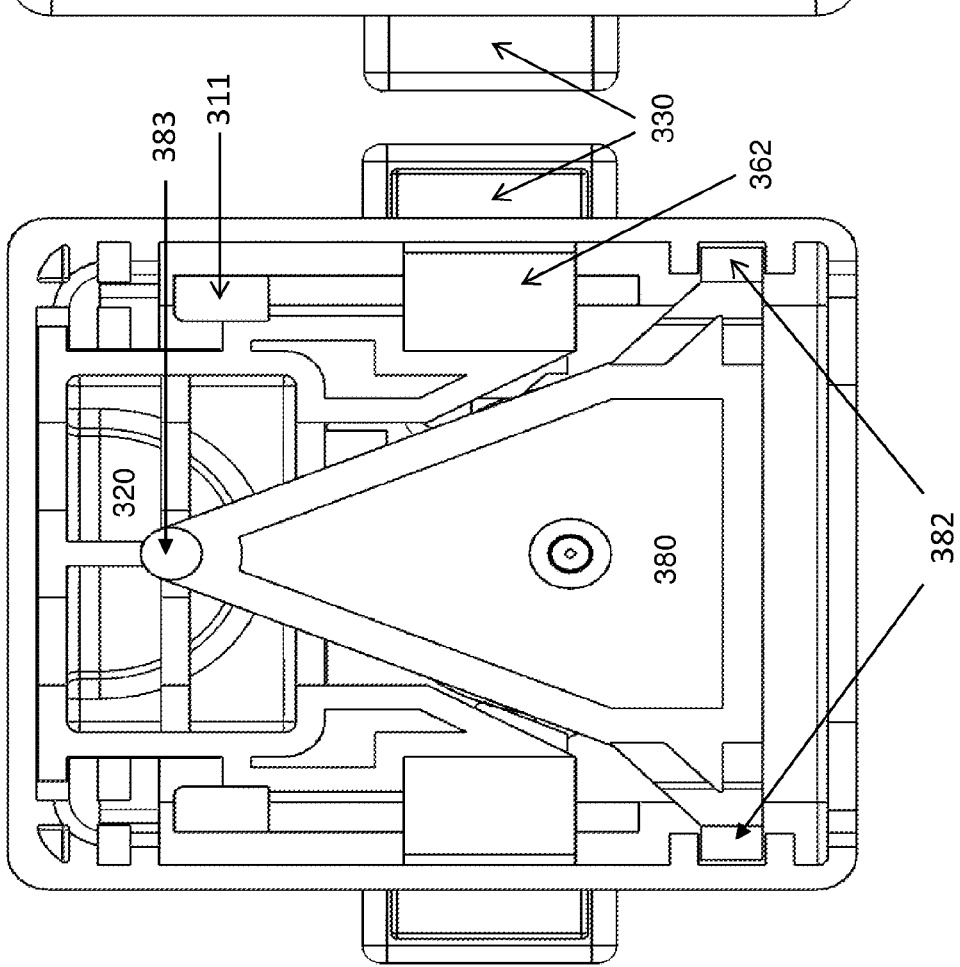

FIGS. 38A-B show cross section planar bottom (FIG. 38A) and top (FIG. 38B) views of the inserter 300, according to some embodiments. FIG. 38A shows the inserter hammer 380 that includes the hammer lead 382 (both sides) and cannula pusher 383. The hammer lead maintains linear displacement of the hammer 380 during downward movement. Upon inserter activation, the cannula pusher 383 pushes the cannula downward. The trigger 320 includes the trigger stopper 362 (both sides) that is released by pressing the safety catch 320. The DP holder 311 (both sides) holds the DP adhesive base in place at the bottom side of the inserter before inserter activation and cannula insertion. After inserter activation, the DP holder 311 is displaced laterally and the DP adhesive base is released (FIG. 41). FIG. 38B shows the inserter housing 310, trigger 320, and safety catch 330 (both sides).

Figure 39:
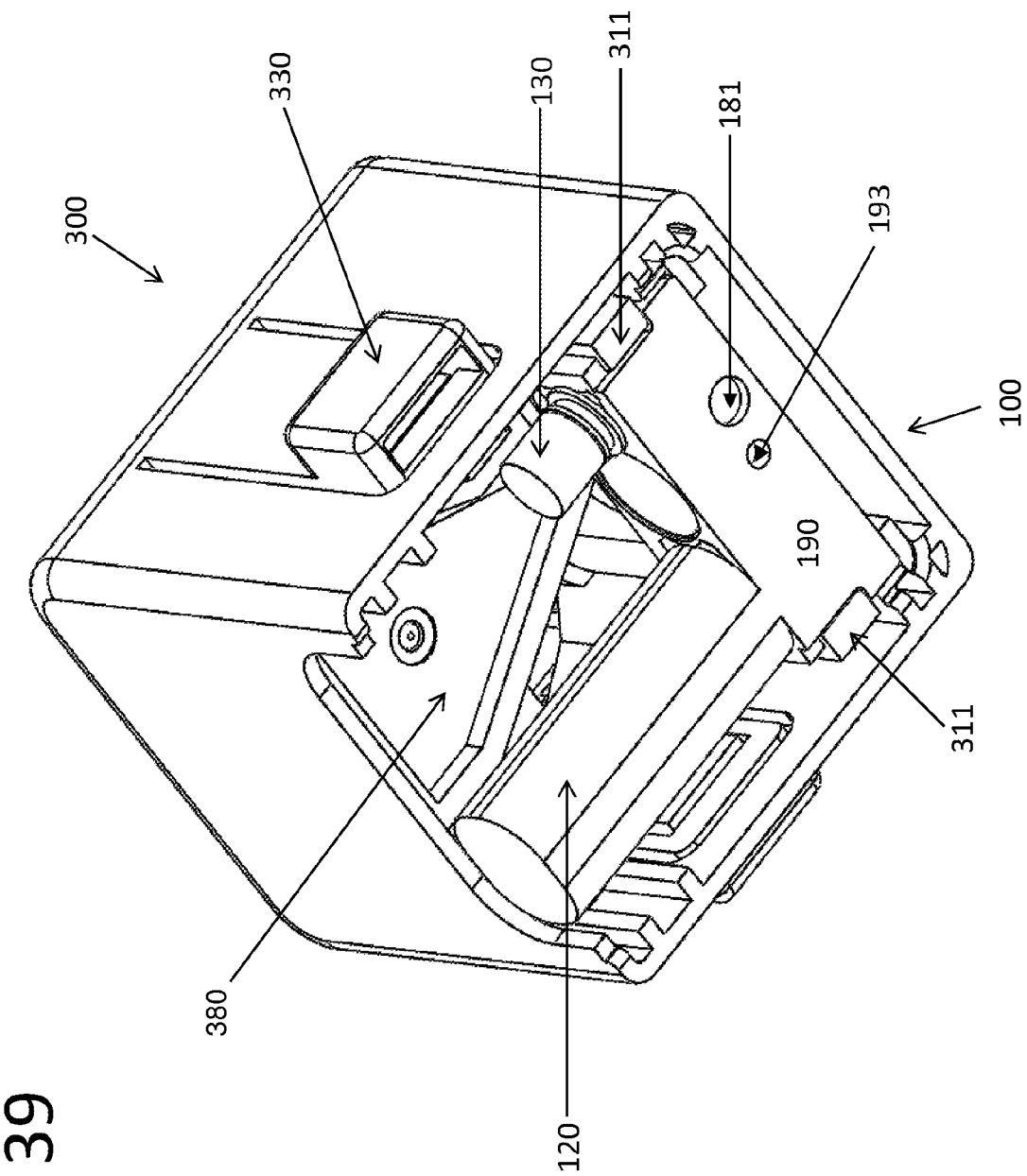

FIG. 39 shows a spatial view of the bottom side of the inserter 300 and the DP 100 (adhesive base 190 partially removed) within the inserter 300, according to some embodiments. The inserter 300 includes the housing 310, hammer 380, safety catch 330, and DP holder 311 (both sides). The DP 100 includes the first reservoir 120, doser 130, filling aperture 181, and cannula aperture 193. The DP holders 311 hold the DP adhesive base 190 in place before inserter 300 activation. After inserter activation, the DP holders 311 are displaced laterally (FIG. 41), releasing the DP adhesive base 190 and allowing free removal of the inserter.

Figure 40:
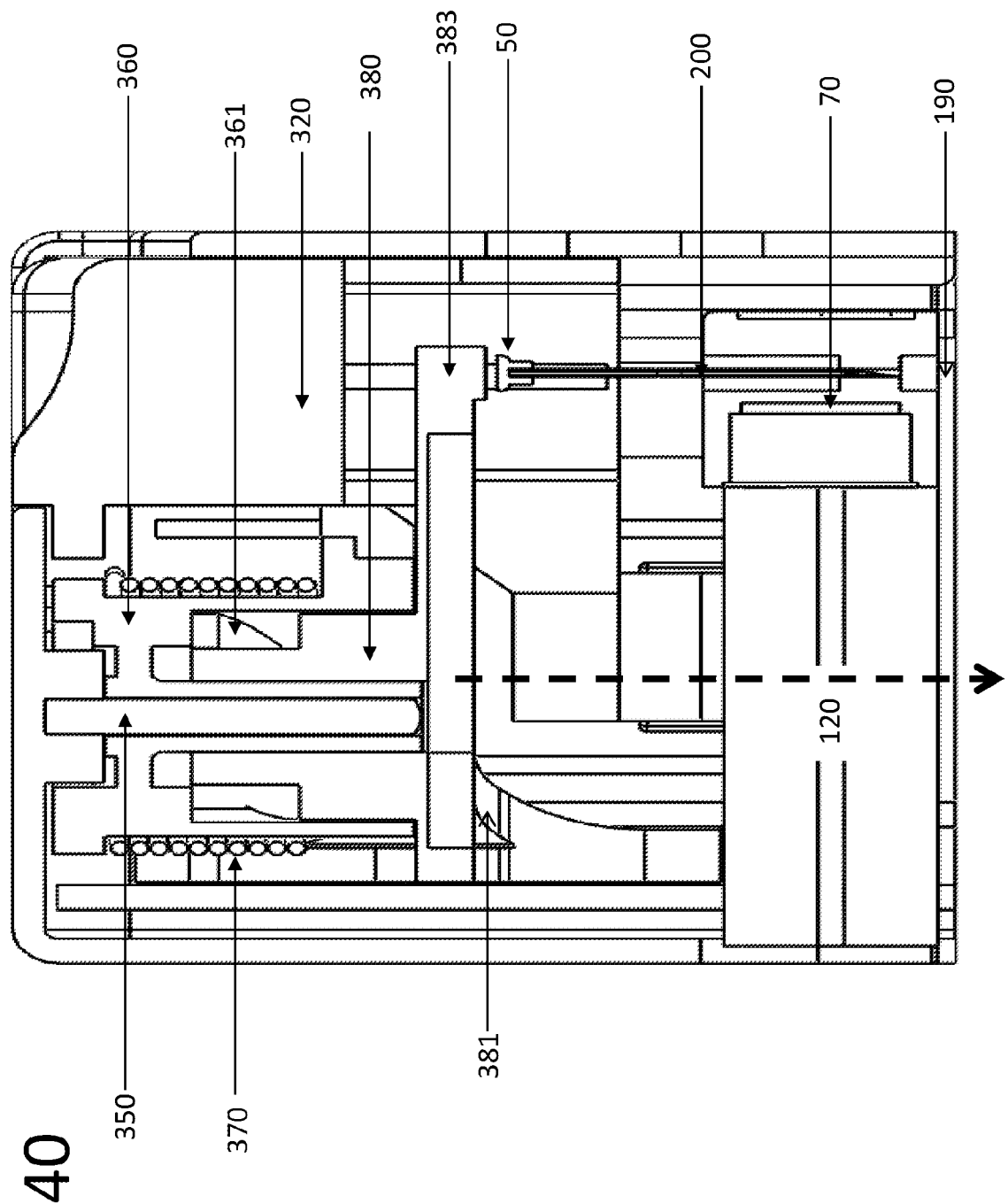

FIG. 40 shows a transverse cross section view of the inserter 300 and DP 100, according to some embodiments. The inserter includes the trigger 320, inserter rotating nut 360, rotating thread 361, inserter spring 370, pivoting rod 350, inserter hammer 380, cannula pusher 383, and liner thread 381. The DP includes the first reservoir 200, DP magnet 70, cannula 200, and adhesive base 190. Upon pressing the trigger 320, the inserter spring 370 rotates the inserter rotating nut 360 and inserter thread 361 around the pivoting rod 350. The hammer linear thread 381 is linearly displaced downward (direction of bold dashed line) upon rotation of the rotating thread 361, and consequently, the hammer 380 and hammer pusher 383 are displaced in the same direction. Downward displacement of the cannula pusher 383 displaces the cannula 200 in the direction of the dashed line.

FIGS. 41A-B show transverse cross sectional views of the inserter 300 and the patch pump 1 before (FIG. 41A) and after (FIG. 41B) first reservoir 120 filling, according to some embodiments. The inserter 300 includes the trigger 320, viewing window 390, inserter spring 370, and inserter hammer 380. The patch pump 1 includes the first reservoir 120, first reservoir plunger 121, cannula 200, adhesive base 190, and liner 197. During first reservoir filling, insulin displaces the second reservoir plunger 121 in the direction of the bold dashed line arrow (FIG. 41A). When the first reservoir 120 is filled to maximum capacity (FIG. 41B), the first reservoir plunger 121 is positioned at the most proximal end.

FIGS. 42A-B show planar cross section views of the releasing mechanism 340 before (FIG. 42A) and after (FIG. 42B) inserter 300 activation, according to some embodiments. Rotation (counterclockwise direction) of the splitter 363 (FIG. 42A) displaces laterally (directions of bold dashed line arrows) the lever 3111 which displaces the DP holders 311 in the same lateral directions. Consequently (FIG. 42B), the DP adhesive base 190 is disengaged from the inserter.

FIGS. 43A-E show spatial views of the inserter 300 handling, according to some embodiments. FIG. 43A shows the insertion of the RP 10 into the inserter notch 312 and connection of the RP 10 with the DP 100 (partially shown). FIG. 43B shows the patch pump 1 (partially shown) within the inserter 300; the RP 10 is now connected to the DP 100. The liner 197 is folded around the upper and bottom sides of the adhesive base 190. FIG. 43C shows the first reservoir filling. The patch pump (hidden) is situated at the bottom side of the inserter 300. Insulin is injected with a syringe 500 and a syringe needle (not shown) through the filling aperture 181. FIG. 43D shows the inserter 300 and the patch pump 1 after removal of liner 197 from the adhesive base 190. FIG. 43E shows the inserter 300 after disconnection from patch pump 1. The adhesive base 190 is now adhered to the patient skin and the inserter 300 is disposed.

Figure 44A:
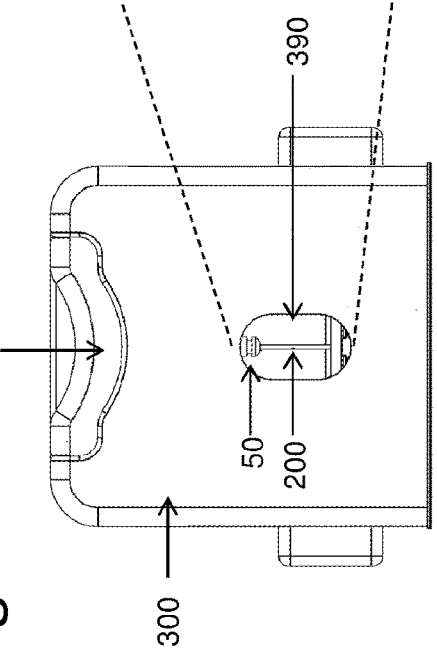
FIG. 44A shows an inserter including a trigger and viewing window.
Figure 44B:
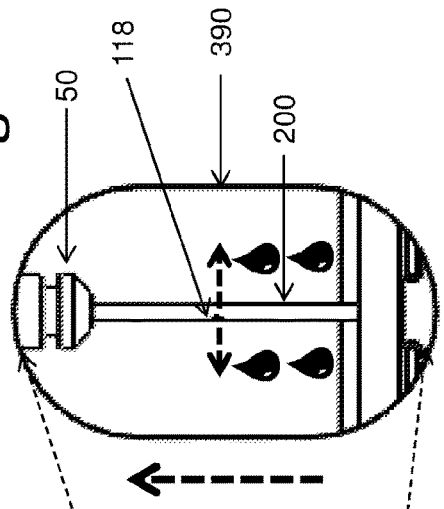
FIG. 44B shows a magnified view (light dashed line arrows) of the viewing window during priming.
Figure 44C:
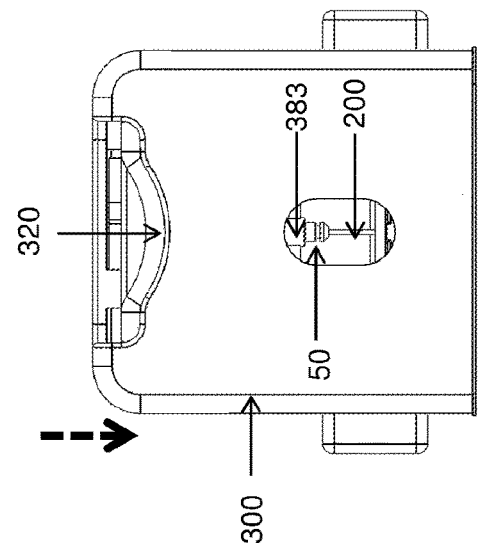
FIG. 44C shows the inserter during the activation of a cannula insertion process.
Figure 44D:
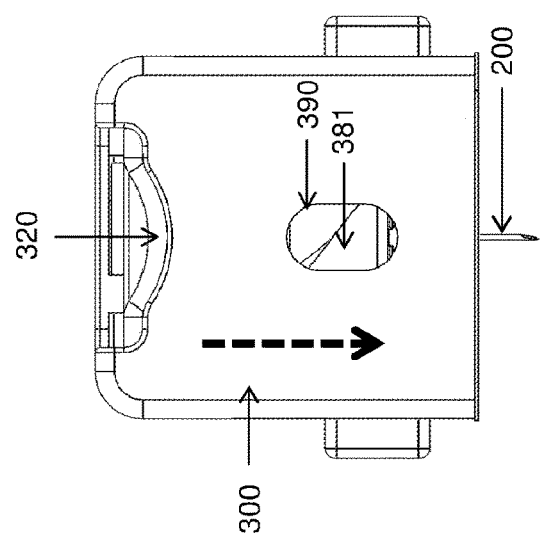
FIG. 44D shows the inserter and the patch pump (not shown) at the end of a cannula insertion process.
Figure 46A:
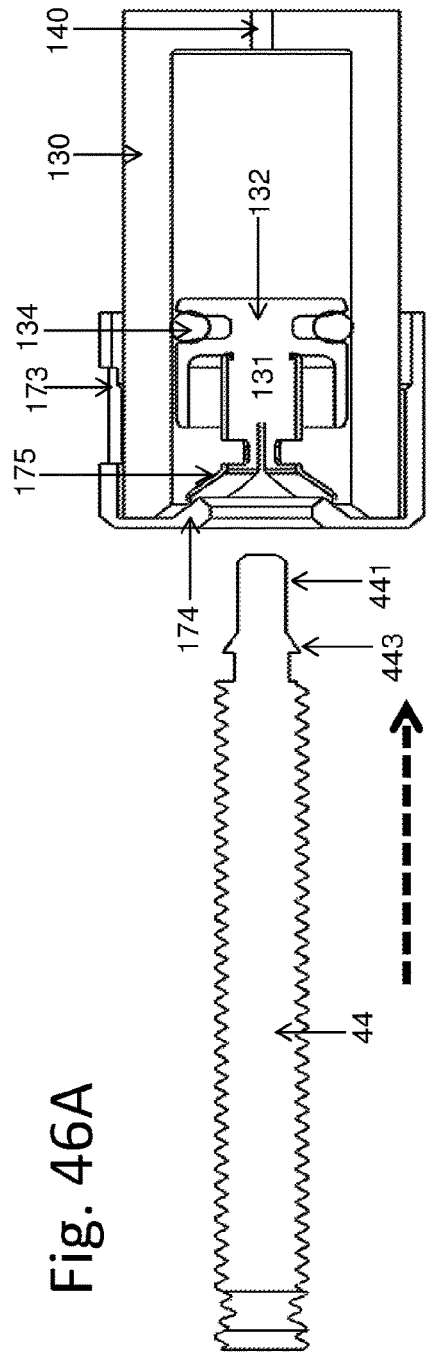
FIG. 46A shows a lead screw including a lead screw tip and a lead screw protrusion.
Figure 46B:
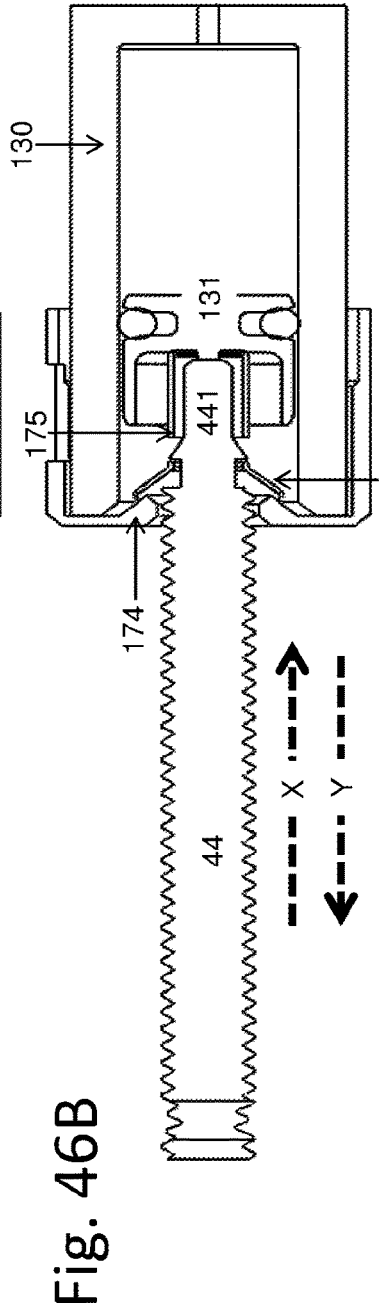
FIG. 46B shows an engaged lead screw and a spring scraper.
Figure 46C:
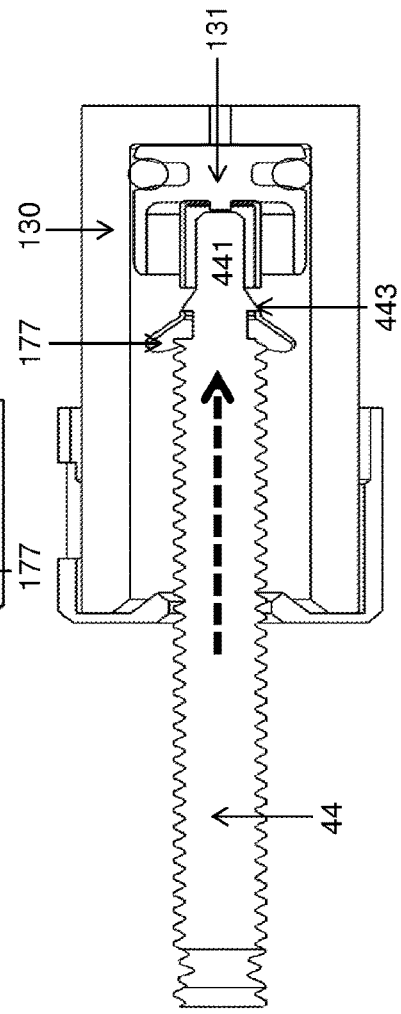
FIG. 46C shows the lead screw engaged with the spring scraper.

FIGS. 44A-D show transverse cross sectional views of the inserter 300 (viewing window perspective) at priming and cannula insertion, according to some embodiments. FIG. 44A shows the inserter 300 including the trigger 320 and viewing window 390. The DP is situated within the inserter 300 and the cannula 200 and cannula cap 50 can be seen through the viewing window 390. Following the RP insertion into the inserter (FIG. 42) the patch pump is ready for priming. Priming is done automatically upon command receiving by the patch pump from the controller. FIG. 44B shows a magnified view (light dashed line arrows) of the viewing window 390 during priming. The cannula 200, cannula cap 50, and cannula opening 118, can be seen at the inserter viewing window 390. During priming, the inserter 300 and viewing window 190 are held in upright position (dashed dotted line arrow). When insulin is seen emerging constantly (e.g., no air bubbles) from the cannula opening 118 (drops) priming is completed, the path pump can be adhered to the skin, and the cannula 200 can be inserted. FIG. 44C shows the inserter 300 during the activation of the cannula insertion process, the trigger 320 is pressed downward in the direction of the bold dashed line arrow and the hammer cannula pusher 383 displaces the cannula 200 in the same direction. FIG. 44D shows the inserter and the patch pump (not shown) at the end of the cannula 200 insertion process. The trigger 320 is pressed in the direction of the bold dashed line arrow; the hammer linear thread 381 is seen in the viewing window 190 after completion of linear displacement in the same direction, and the cannula is protruding from the bottom side of the adhesive base (not shown) after being fully displaced in the same direction.

FIGS. 45A-B show cross section, partially transparent views (viewing window perspective) of the inserter 300 and the patch pump 1 before (FIG. 45A) and after (FIG. 45B) cannula 200 insertion, according to some embodiments. The inserter 300 includes the trigger 320, viewing window 390, inserter spring 370, hammer linear thread 381, and hammer cannula pusher 383. The patch pump 1 includes the first reservoir 120, doser 130, cannula 200, and cannula cap 50. FIG. 45A shows the inserter 300 during the activation of the cannula insertion process. The trigger 320 is pressed downward in the direction of the bold dashed line arrow and the hammer cannula pusher 383 displaces the cannula 200 in the same direction. FIG. 45B shows the inserter 300 and the patch pump 1 at the end of the cannula 200 insertion process. The trigger 320 is pressed in the direction of the bold dashed line arrow; the hammer linear thread 381 is seen in the viewing window 190 after completion of linear displacement in the same direction, and the cannula is protruding from the bottom side of the adhesive base (not shown) after being fully displaced in the same direction.

FIGS. 46-53 show reversible engagement mechanisms between the RP lead screw and the DP doser plunger, according to some embodiments. The engagement mechanism provides firm connection during patch pump operation and allows disengagement during RP-DP disconnection. For example, FIGS. 46A-C show an example embodiment of the engagement mechanism between the lead screw 44 and doser plunger 131. FIG. 46A shows the lead screw 44 including the lead screw tip 441 and the lead screw protrusion 443. The doser 130 is rigidly connected to the sliding needle 140 and can be linearly displaced within the sleeve (not shown) and the sleeve cover 173. The sleeve cover 173 has a protrusion 174. The doser plunger 131 can be linearly displaced within the doser 130. The doser plunger 130 includes the piston 132 and gasket 134, and the scraper spring 175. During RP-DP connection (direction of bold dashed line arrow) the lead screw tip 441 and lead screw protrusion 443 are reversibly engaged with the spring scraper 175. FIG. 46B shows the engaged lead screw 44 and the spring scraper 175. The doser plunger 131 is situated at the most proximal location within the doser 130 and the scraper petal 177 (magnified view in FIG. 47) is touching the sleeve cover protrusion 174. A linear displacement of the lead screw 44 in the direction of the bold dashed line arrow (X) displaces the plunger 131 at the same direction. A linear displacement of the lead screw 44 in the direction of the bold dashed line arrow (Y) forces the spring scraper petal 177 against the sleeve cover protrusion 174 and consequently the spring scraper 175 is enlarged, the lead screw protrusion 443 is disengaged, and the lead screw 44 (and the entire RP) can be disengaged from the doser plunger 31 (and the entire DP). FIG. 46C shows the lead screw 44 engaged with the spring scraper 175, the lead screw tip 441 and lead screw protrusion 443 are situated within the spring scraper groove 179 (shown in FIG. 47) and the doser plunger 131 is displaced at the direction of the bold dashed line arrow to the most distal position within the doser 130 (end of doser emptying phase, FIG. 55).

FIG. 47A-C shows magnified spatial views of the spring scraper 175 and the lead screw 44, according to some embodiments. FIG. 47A (side view) and FIG. 47B (top view) show the spring scraper 175. The spring scraper includes the scraper ribs 176, scraper petal 177, and scraper groove 179. FIG. 47C shows the lead screw 44 including the lead screw tip 441 and the lead screw protrusion 443. When the lead screw 44 is engaged with the spring scraper 175, the lead screw tip 441 and lead screw protrusion 443 reside within the spring scraper groove 179.

Figures 48A, 48B:
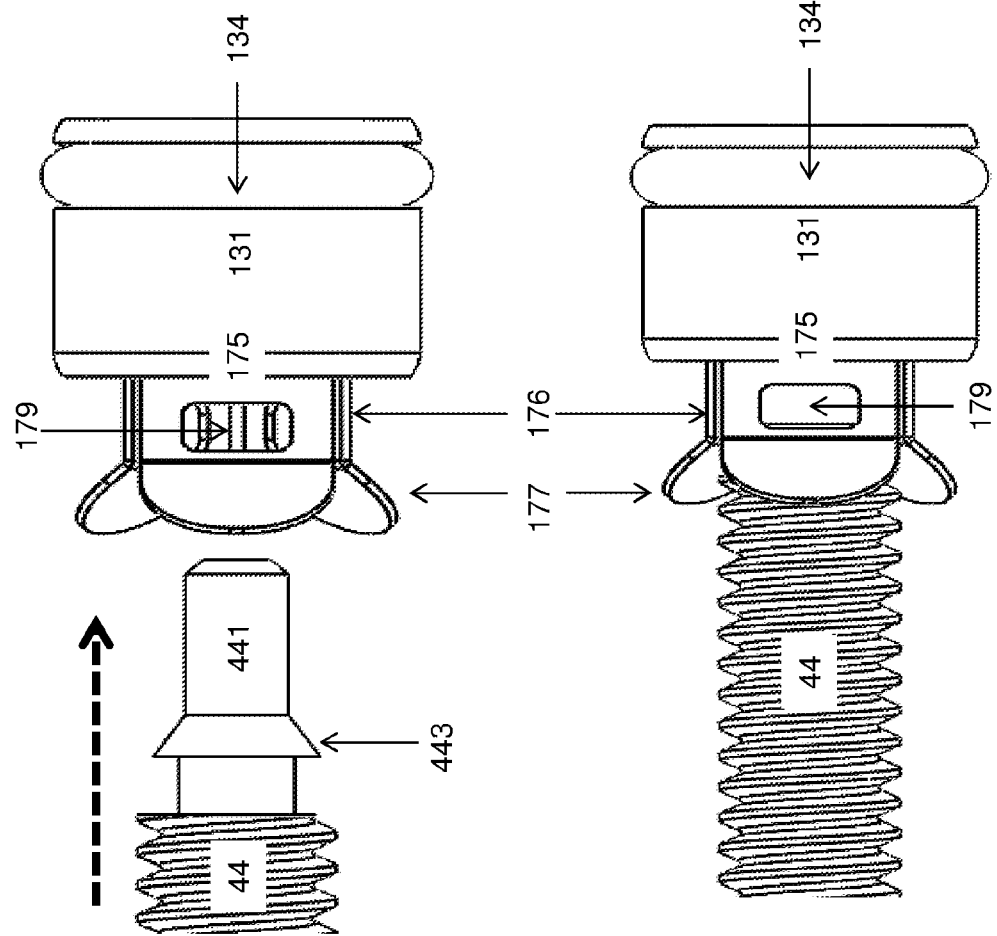
FIGS. 48A-B show magnified spatial views of the spring scraper and the lead screw before and after engagement.
Figure 50A:
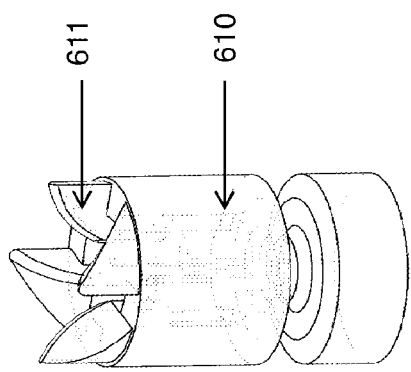
FIGS. 50A-F show spatial views of a doser plunger, sleeve cover and driving screw tip.
Figure 50B:
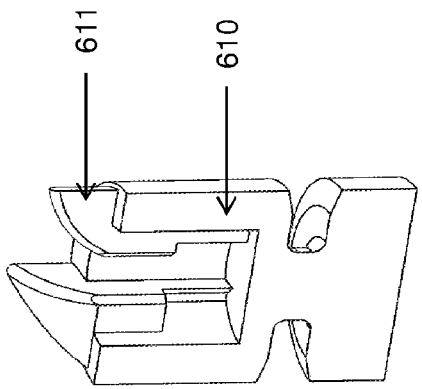
Figure 50C:
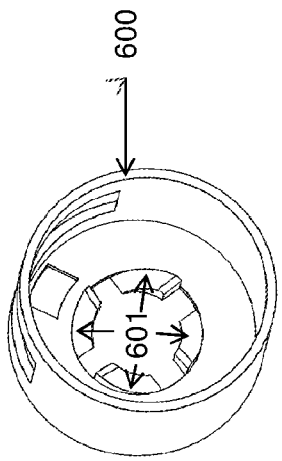
Figure 50D:
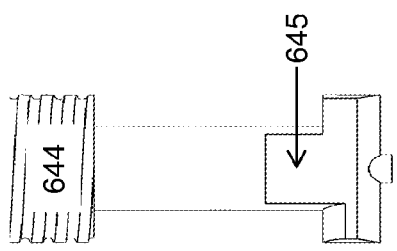
Figure 50E:
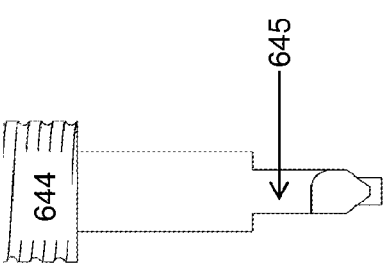
Figure 50F:
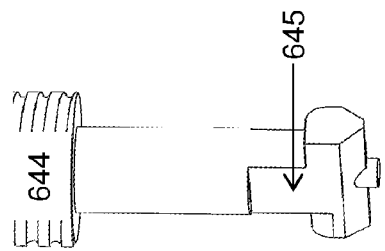
Figure 51A:
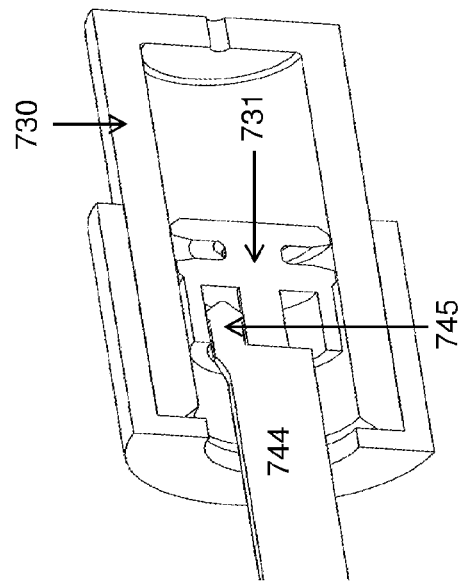
FIGS. 51A-D show cross sectional view (FIG. 51A), spatial cross-sectional view (FIG. 51B) and spatial views (FIGS. 51C-D) of a bind engagement mechanism.
Figure 51D:
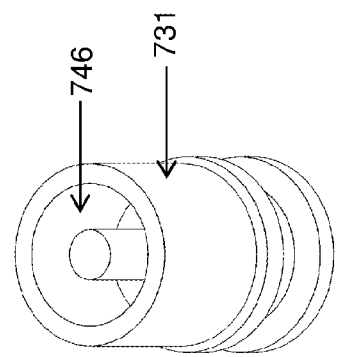
Figure 51B:
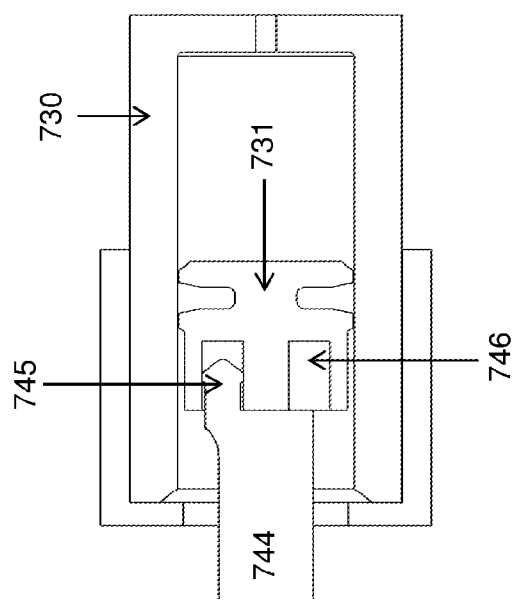
Figure 51C:
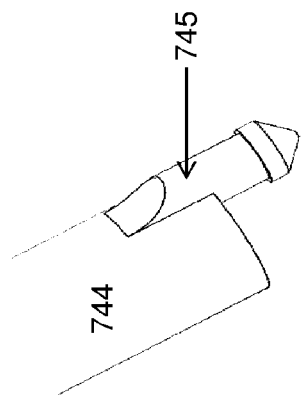

FIGS. 48A-B show longitudinal cross sectional views of the lead screw 44 and the doser plunger 131 before (FIG. 48A) and after (FIG. 48B) engagement, according to some embodiments. The lead screw 44 includes the lead screw tip 441 and the lead screw protrusion 443. The doser plunger 131 includes the gasket 134, scraper spring ribs 176, and scraper spring petal 177. FIG. 48A shows the lead screw 44 and doser plunger 131 before engagement. The lead screw 44 is displaced in the direction of the bold dashed line arrow and resides within the scraper spring groove 179. FIG. 48B shows the lead screw 44 engaged with the scraper spring 175. The scraper spring 175 includes the scraper spring ribs 176 and scraper spring petal 177. The lead screw tip and lead screw protrusion (hidden) are situated within the scraper spring groove 179.

FIGS. 49A-C show spatial views (FIGS. 49A-B) and cross sectional view (FIG. 49C) of a bayonet engagement mechanism, according to some embodiments. The driving screw 644 includes a tip 645 that has a T-shape configuration (FIG. 50). The sleeve cover 600 includes four cogs 601 and the doser plunger 610 includes four cogs 611. When the plunger 610 is situated at the most proximal position, the doser plunger cogs 611 and the sleeve cover cogs 601 are engaged, the doser plunger 611 rotates, and the driving screw tip 645 is disengaged from the doser plunger 610.

FIGS. 50A-F show spatial views of the doser plunger 610 (FIGS. 50A-B), sleeve cover 600 (FIG. 50C), and driving screw tip 645 (FIGS. 50D-F), according to some embodiments. The plunger 610 includes four cogs 611 and the sleeve cover 600 includes four cogs 601. In some embodiments, the plunger and/or the sleeve cover may include less than or more than four cogs. Engagement of cogs 601 with cogs 611 provides rotation of doser plunger 610 and disengagement of driving screw tip 645 from doser plunger 610.

FIGS. 51A-D shows cross sectional view (FIG. 51A), spatial cross sectional view (FIG. 51B) and spatial views (FIGS. 51C-D) of a bind engagement mechanism, according to some embodiments. The driving screw 744 includes a tip 745 that has a shape of a lance. The doser plunger 731 includes a circular notch 746. The driving screw tip 744 is firmly engaged with the doser plunger notch 746 because of a non-collinearity (binding phenomenon). When the plunger 731 is situated at the most proximal position within the doser 730, the doser plunger circular notch 746 and the driving screw tip 745 are collinearly aligned and can be disengaged.

Figure 52:
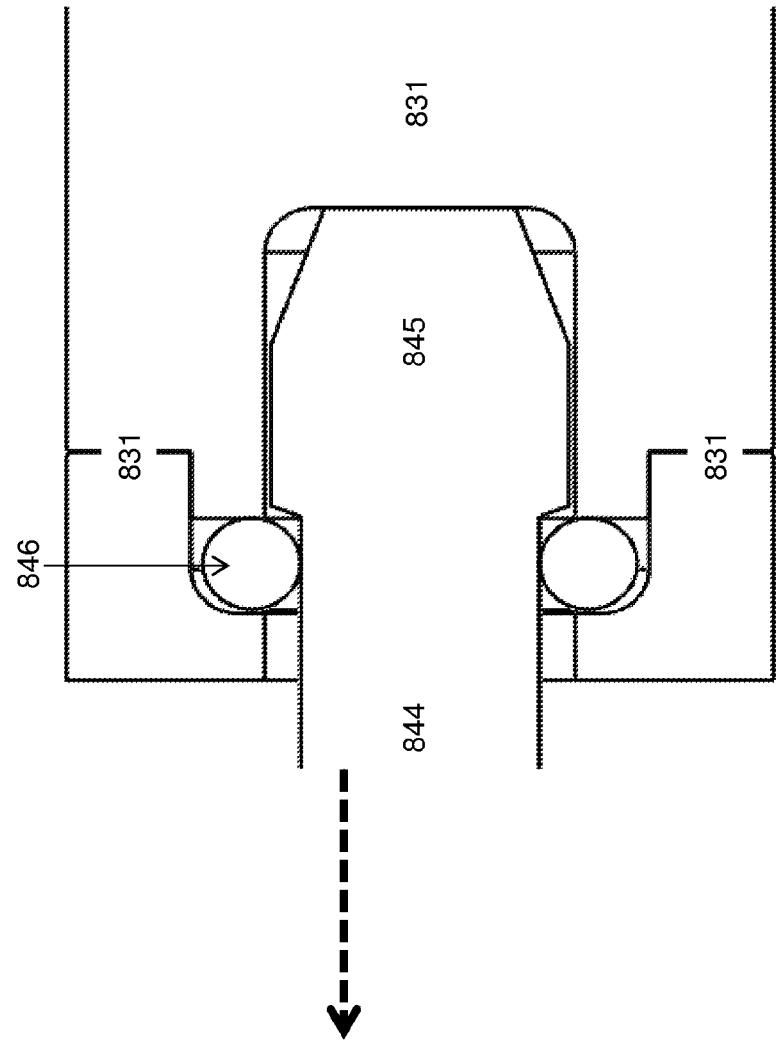
Figure 54C:
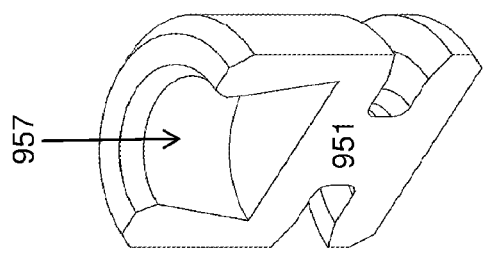
FIGS. 54B-E show various spatial views of the undercut locking washer engagement mechanism.
Figure 54B:
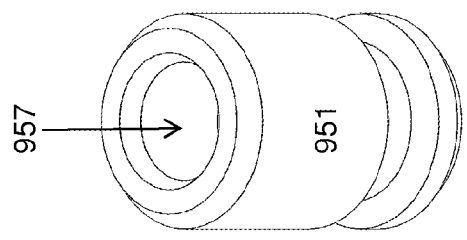
Figure 54E:
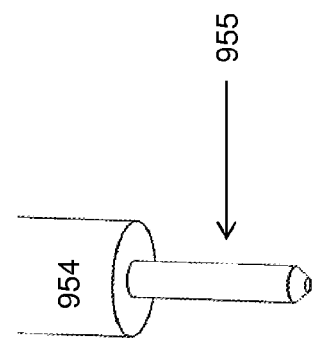
Figure 54D:
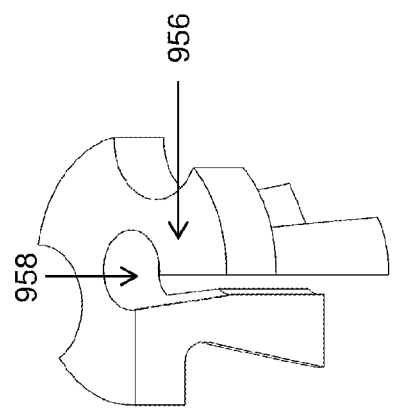
Figure 54A:
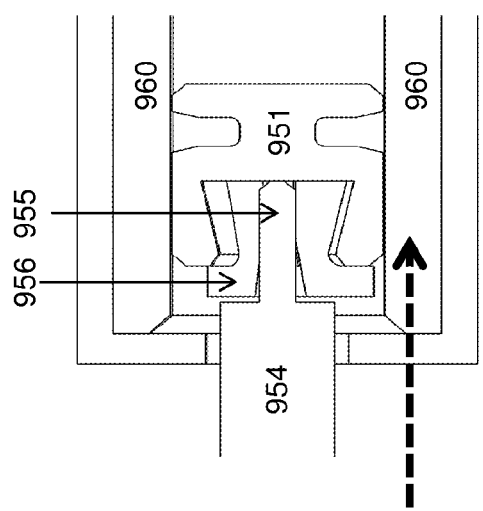
FIG. 54A shows a cross sectional view of an undercut locking washer engagement mechanism.

FIG. 52 shows a cross sectional view of an O-ring engagement mechanism, according to some embodiments. The driving screw 844 includes a bulged tip 845. The doser plunger 831 includes an O-ring 846. When the plunger 831 is situated at the most proximal position within the doser (not shown), additional movement of the driving screw in the direction of the bold dashed line arrow causes the bulged tip 845 to squeeze the O-ring 846 and the driving screw 844 is disengaged from the doser plunger 831.

FIGS. 53A-B shows cross sectional view (FIG. 53A) and spatial view (FIG. 53B) of a pot magnet engagement mechanism, according to some embodiments. The driving screw 944 includes a potted tip 948 and a magnet/iron plate 945 that is connected to the potted tip 948. The doser plunger 931 includes a magnet/iron plate 946. The potted tip 948 and doser plunger 931 can be engaged (bold dashed line arrow X) or disengaged (bold dashed line arrow Y) if the driving screw is linearly displaced in the direction of the plunger 931 and the opposite direction of the plunger 931 respectively.

FIGS. 54A-E show cross sectional view (FIG. 54A) and spatial views (FIGS. 54B-E) of an undercut looking washer engagement mechanism, according to some embodiments. The driving screw 954 includes a tip 955 that is shaped like a lance. The doser plunger 951 includes a cone shaped cavity 957. A cone shaped scaffold 956, that has an opening 958, occupies the cavity 957. When the driving screw 954 is engaged with the doser plunger 951, the driving screw tip 955 is situated within the opening 958 and the tip 955 is firmly engaged with the scaffold 956. When the plunger 951 is situated at the most proximal position within the doser 960, the scaffold 956 is displaced within the cavity 957 in the direction of the bold dashed line arrow and the driving screw tip 955 can be disengaged from the scaffold 957.

FIGS. 55-58 show schemes of the patch pump operation including the pumping mechanism (doser filling phase—FIG. 55 and doser emptying phase—FIG. 56) and patch pump priming (FIG. 57), and reservoir filling (FIG. 58) according to some embodiments. The pumping mechanism of the patch pump includes an operation cycle that is comprised of two operating phases-doser filling phase and doser emptying phase. During the doser filling phase, insulin is delivered from the first reservoir to the doser. During the doser emptying phase, insulin is delivered from the doser to the exit port and from the exit port through the cannula to the patient. The patch pump priming cycle includes two operating phases—doser filling phase and doser emptying phase. During the doser emptying phase, insulin is delivered from the doser to the exit port and from the exit port to the cannula opening and from the cannula opening to the air.

Figure 55:
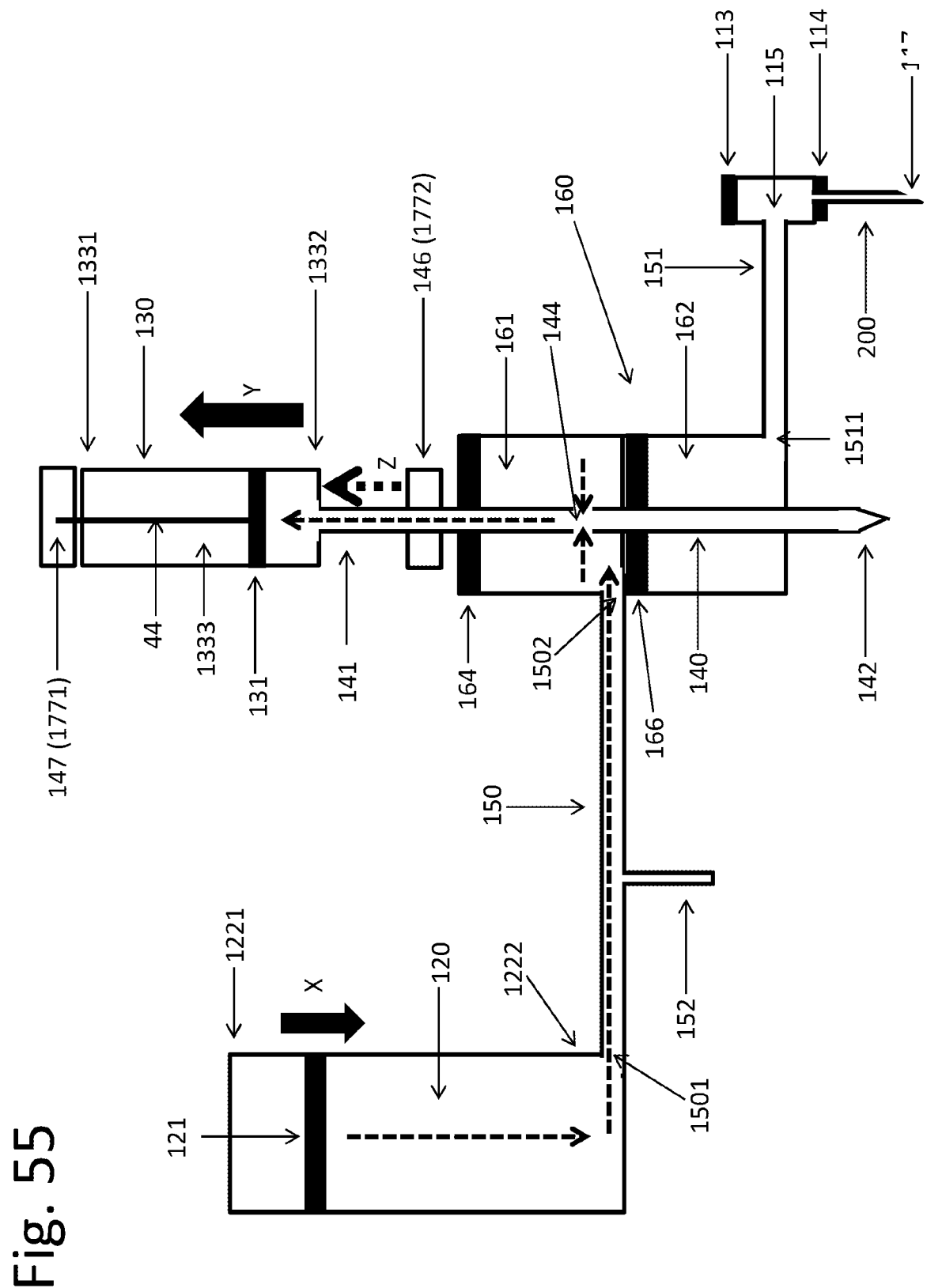
FIGS. 55-58 show schemes of the patch pump operation including the pumping mechanism operation cycle (doser filling phase and doser emptying phase), patch pump priming, and patch pump filling, according to some embodiments.
Figure 56:
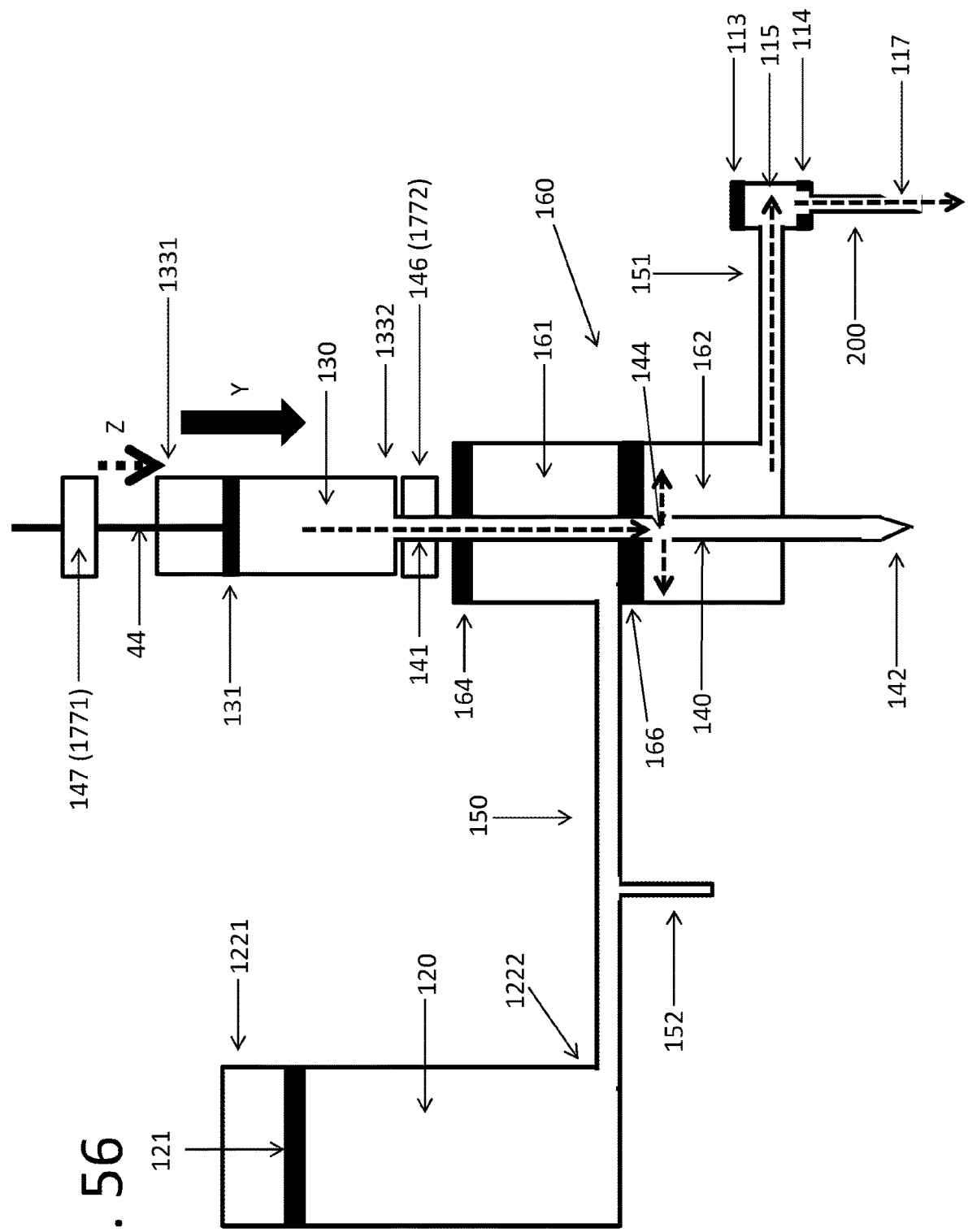

FIG. 55 shows a scheme of the pumping mechanism during the doser filling phase, according to some embodiments. The pumping mechanism includes the first reservoir 120, second reservoir (doser) 130, dual chamber valve mechanism ("valve mechanism") 160, first conduit 150, second conduit 151, exit port 115, and cannula 200. The filling conduit 152 is hydraulically connected to the first conduit 150. The first reservoir 120 has a proximal end 1221, a distal end 1222 and a first conduit-first reservoir passage 1501. The first reservoir plunger 121 can be passively displaced in the direction of the bold arrow (X). The doser 130 has a proximal end 1331 and a distal end 1332. The doser plunger 131 can be displaced by the lead screw 44 in the direction of the bold arrow (Y). The doser proximal stopper 147 (proximal end of sleeve 1771) limits the doser displacement in the direction of the bold arrow (Y). The doser distal stopper 146 (distal end of the sleeve 1772) limits the doser 130 displacement in the opposite direction during the doser emptying phase (FIG. 56). The doser 130 is rigidly connected to the sliding needle 140 and the doser cavity 1333 is in hydraulic communication with the sliding needle 140. The sliding needle has a proximal end 141, a distal end (sharp tip) 142, and an opening 144 (one or more openings). The valve mechanism 160 includes the inlet chamber 161, exhaust chamber 162, back seal 164, front seal 166, first conduit-inlet chamber passage 1502, and exhaust chamber-second conduit passage 1511. The exit port 115 includes the top seal 113 and the bottom seal 114. During the doser filling phase, the lead screw 44 and the doser plunger are displaced in the direction of the bold arrow Y. At the beginning of the doser plunger 131 displacement, the doser 130 is displaced in the direction of the bold dashed line arrow (Z) until reaching the proximal stopper 147 (due to friction forces between the doser 130 and doser plunger 131). Displacement of the doser 130 is followed by displacement of the sliding needle 140 in the same direction and positioning the sliding needle opening 144 in the inlet chamber 161. At this point, further displacement of the plunger 131 in the direction of the bold arrow (Y) displaces insulin in the direction of the light dashed line arrows and displacement of the first reservoir plunger 121 in the direction of the bold arrow (X). Insulin is delivered from the first reservoir 120, through the first conduit 150, inlet chamber 161, sliding needle opening 144, sliding needle 140, and into the doser 130.

FIG. 56 shows a scheme of the pumping mechanism during the doser emptying phase (nomenclature of components provided in the description above with reference to FIG. 55), according to some embodiments. During the doser-emptying phase, the lead screw 44 and the doser plunger 131 are displaced in the direction of the bold arrow Y. At the beginning of the doser plunger 131 displacement, the doser 130 is displaced in the direction of the bold dashed line arrow (Z) until reaching the distal stopper 146. Displacement of the doser 130 is followed by displacement of the sliding needle 140 in the same direction and positioning of the sliding needle opening 144 in the exhaust chamber 162. At this point, further displacement of the plunger 131 in the direction of the bold arrow (Y) displaces insulin in the direction of the light dashed line arrows. Insulin is delivered from the doser 130, through the sliding needle 140, sliding needle opening 144, second conduit 151, exit port 115, cannula 200, and into the patient subcutaneous tissue.

Figure 57:
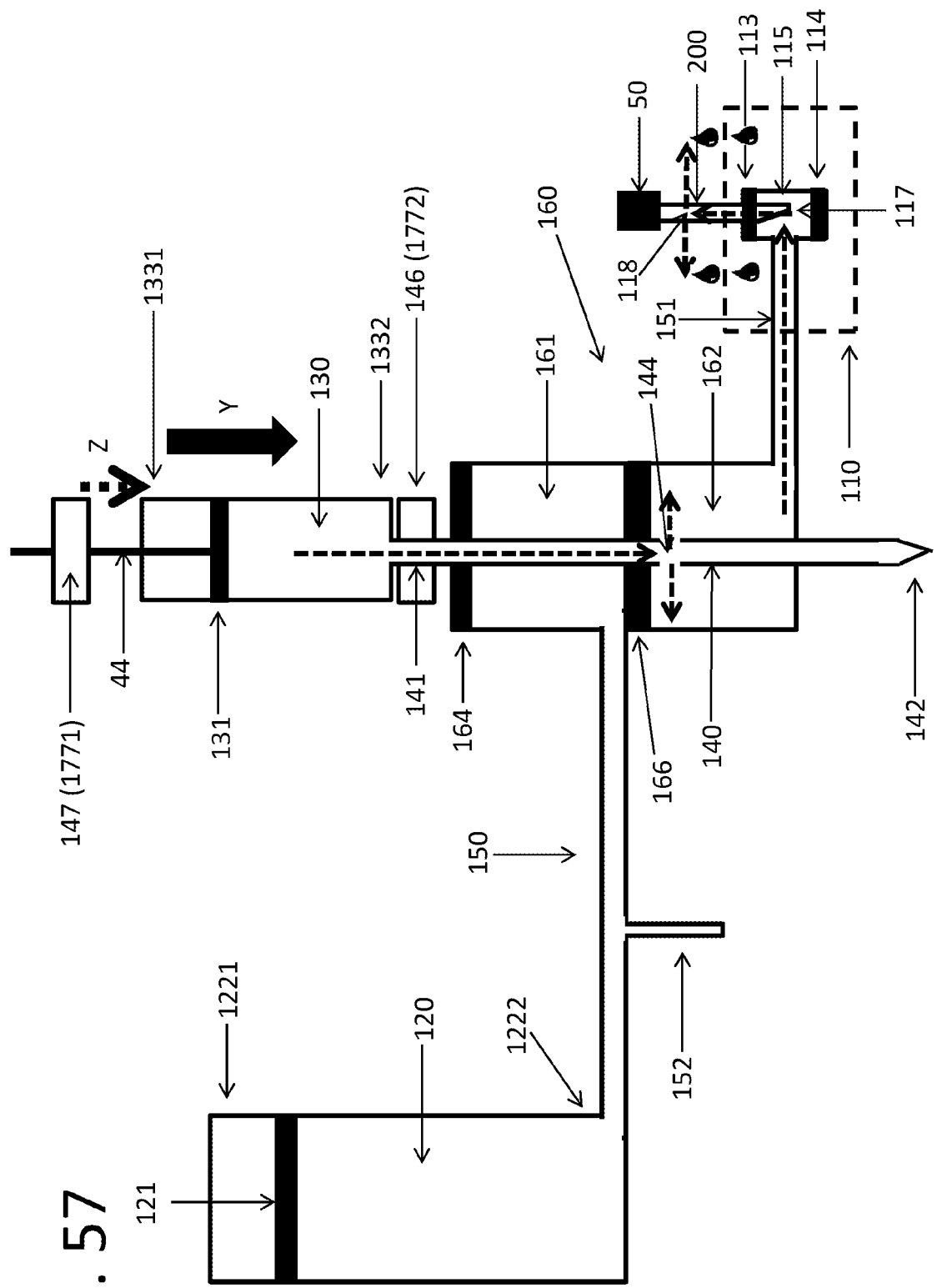

FIG. 57 shows a scheme of the pumping mechanism during patch pump priming (nomenclature of components provided in the description above with reference to FIG. 55), according to some embodiments. The cannula 200 is not inserted in the patient's body, the cannula tip 117 is situated within the well 115, and the cannula cap 50 and cannula opening 118 are situated above the DP housing (110, dashed line square). Following manual reservoir filling (FIG. 58), upon command received from the controller, the patch pump is conducted an automatic priming process (air purging) while the patch pump (and inserter, FIG. 44) is held in an upright position. The priming process includes a priming cycle with two phases, identical to the pump operation phases (FIG. 55 and FIG. 56)—doser filling phase and doser emptying phase. The doser filling phase of the priming process is identical to the doser filling phase of the pump operation cycle (FIG. 55). During the doser emptying phase of the priming process, the lead screw 44 and the doser plunger 131 are displaced in the direction of the bold arrow Y. At the beginning of the doser plunger 131 displacement, the doser 130 is displaced in the direction of the bold dashed line arrow (Z) until reaching the distal stopper 146. Displacement of the doser 130 is followed by displacement of the sliding needle 140 in the same direction and positioning of the sliding needle opening 144 in the exhaust chamber 162. At this point, further displacement of the plunger 131 in the direction of the bold arrow (Y) displaces insulin in the direction of the light dashed line arrows. Insulin is delivered from the doser 130, through the sliding needle 140, sliding needle opening 144, second conduit 151, exit port 115, cannula opening 118, and to the air. If after one priming cycle (doser filling phase and doser emptying phase) insulin is not observed (drops emerging from opening the 118, FIG. 44), consecutive priming cycles are ensuing upon patient discretion until viewing insulin drops.

Figure 58:
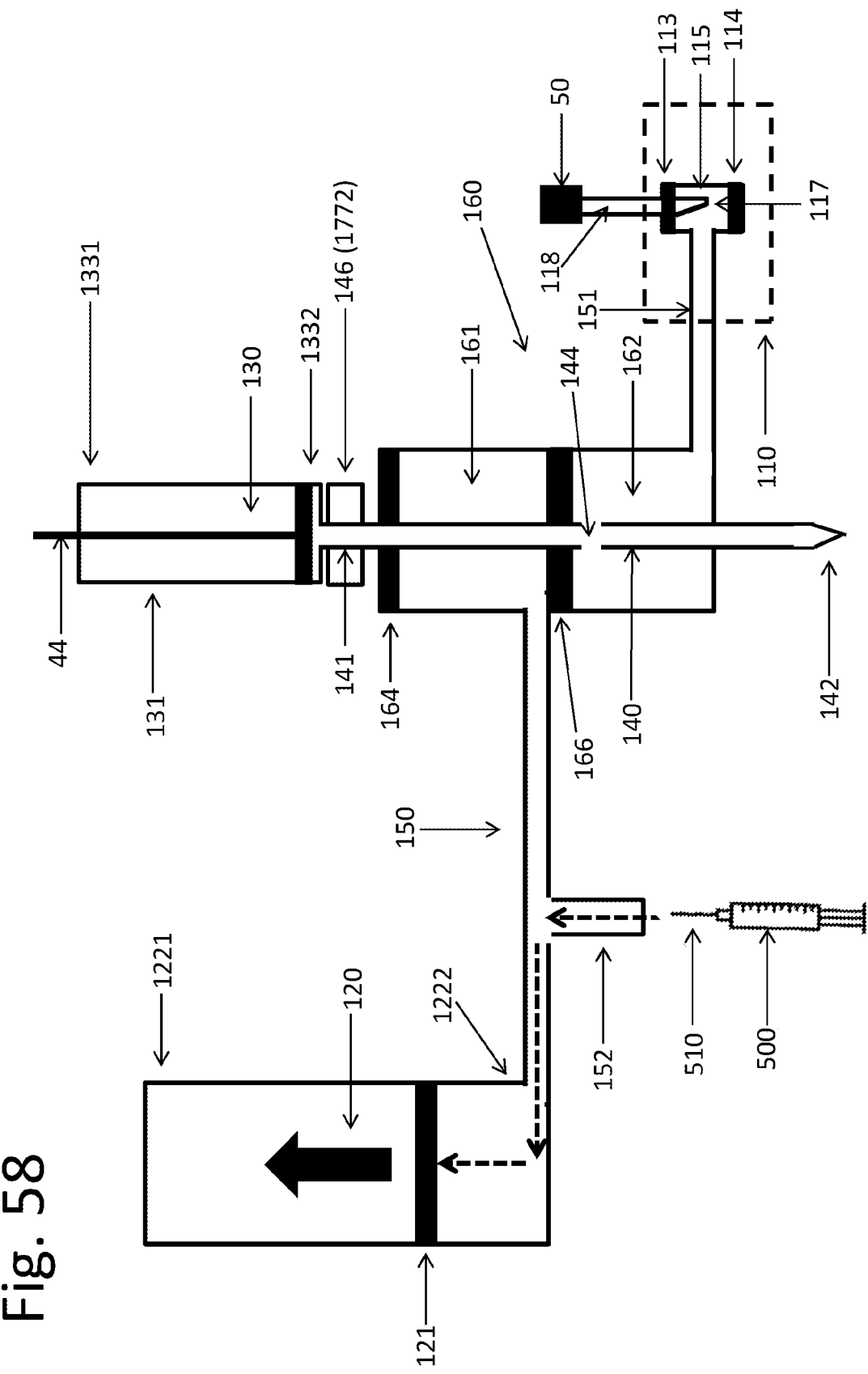

FIG. 58 shows a scheme of the pumping mechanism during patch pump filling (nomenclature of components provided in the description above with reference to FIG. 55), according to some embodiments. The cannula 200 is not inserted in the patient's body, the cannula tip 117 is situated within the well 115, and the cannula cap 50 and cannula opening 118 are situated above the DP housing (110, dashed line square). The doser plunger 131 is situated at the most distal position 1332 and the sliding needle opening 144 is situated within the exhaust chamber 162. Insulin is injected with a filling syringe 500 through a needle 510 into the filling conduit 152 and through the first conduit 150 into the first reservoir 120. During filling the first reservoir plunger 121 is displaced in the direction of the bold arrow. The first reservoir 120 can be filled to any desired volume (FIGS. 71-73) up to the maximal capacity.

Figure 59:
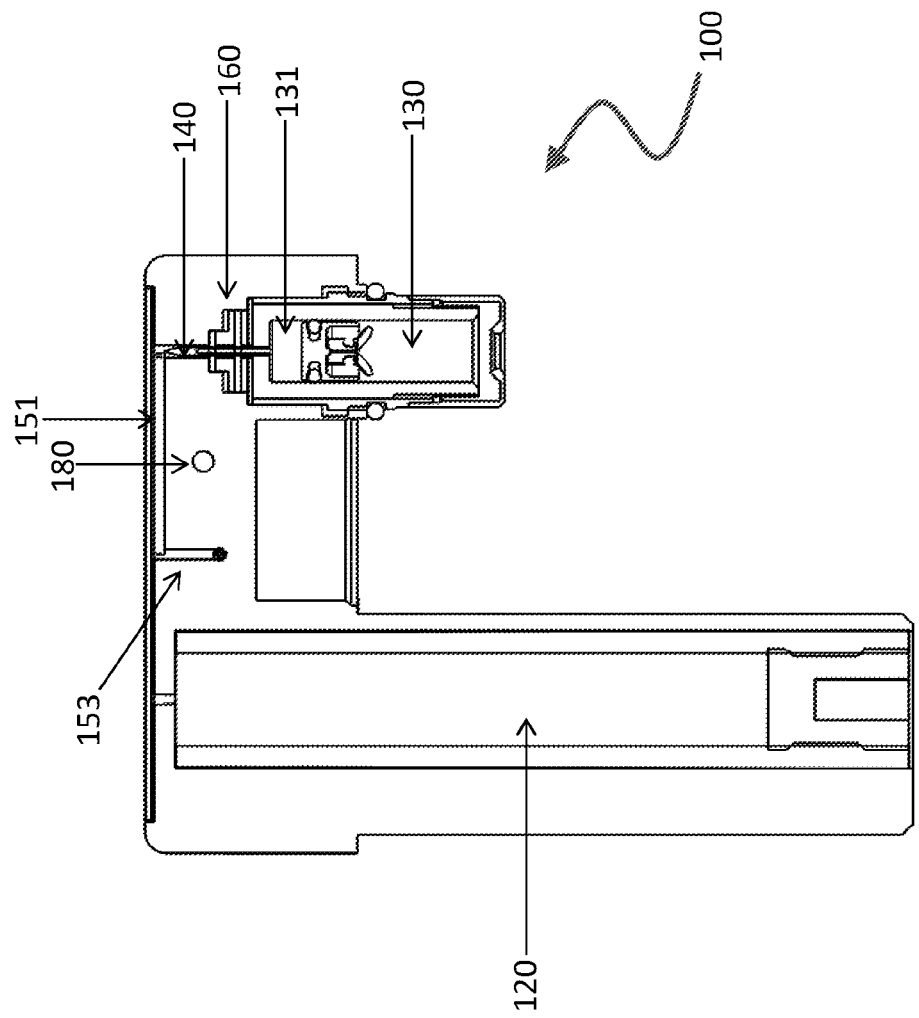

FIGS. 59-64 show the disposable components of the pumping mechanism and the operation cycle of the pumping mechanism, according to some embodiments. For example, in some embodiments, FIG. 59 shows a planar cross section view of some of the DP 100 components and the disposable components of the pumping mechanism. The DP 100 components include the first reservoir 120, doser 130, valve mechanism 160, second conduit 151, delivery conduit 153, and filling port 180. The doser plunger 131 and the sliding needle 140 are situated at the most distal positions (end of doser emptying phase).

Figure 24:
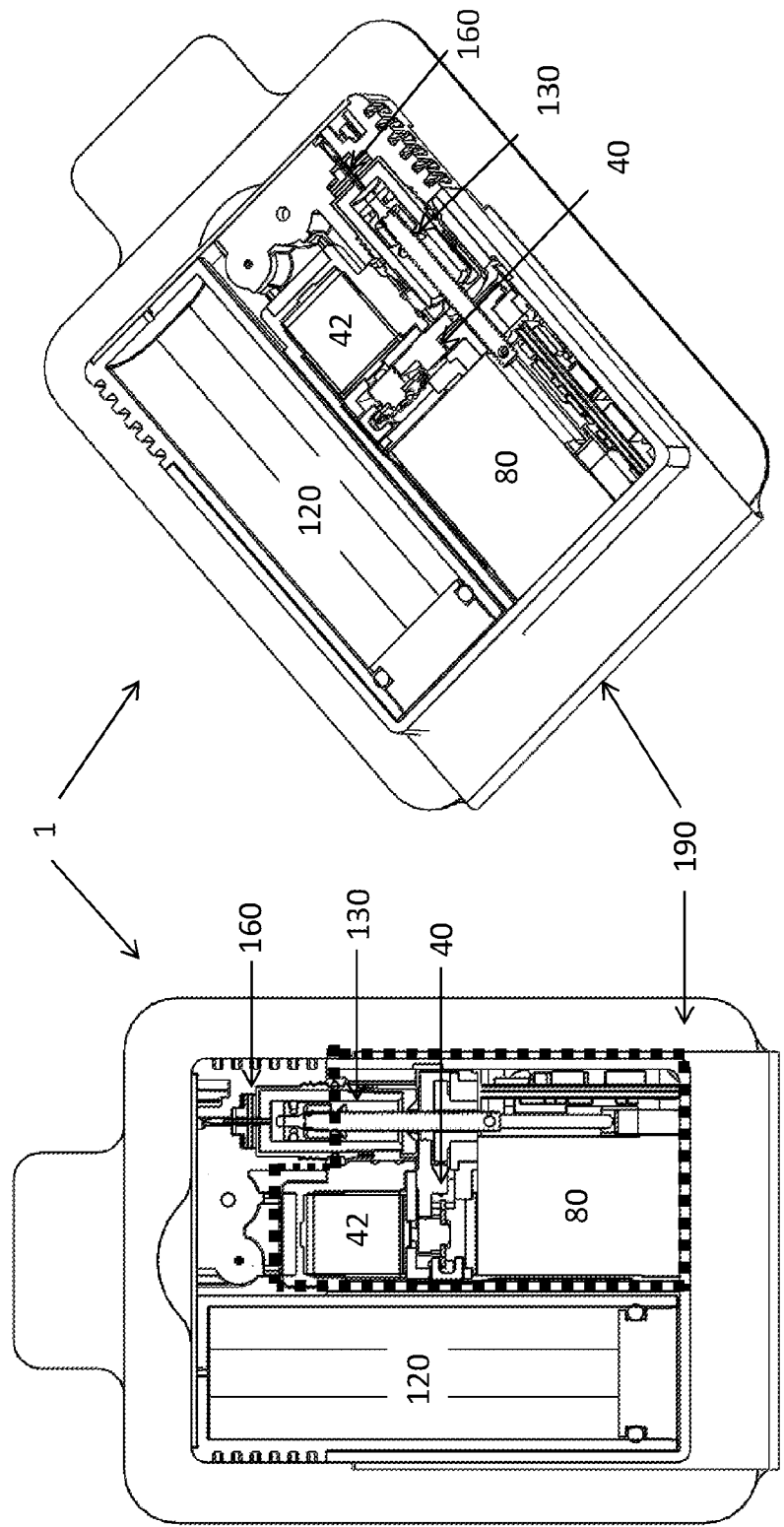
FIGS. 24A-B show planar cross section views of the patch pump, according to some embodiments.
Figure 60:
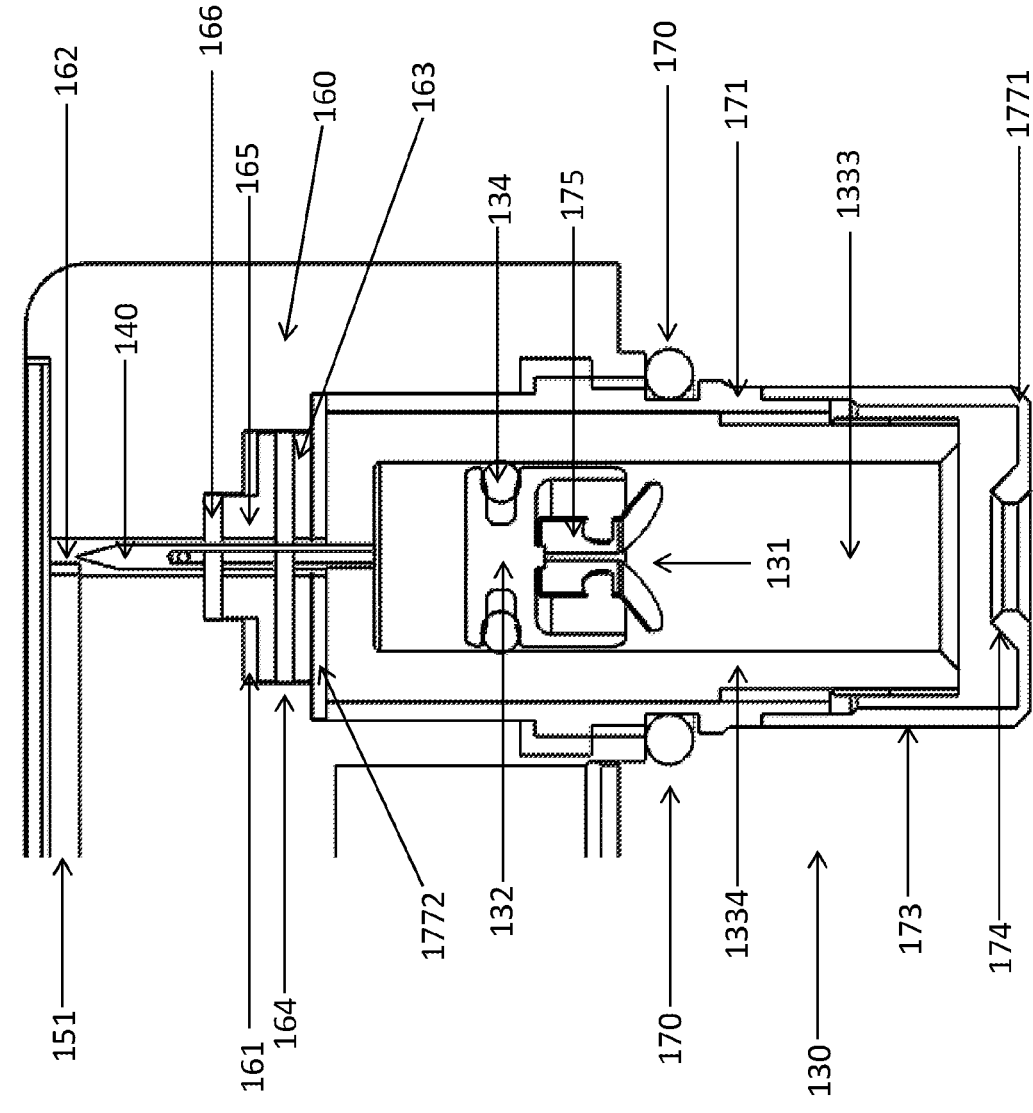

FIG. 60 shows a planar, cross section, magnified view of the disposable components of the pumping mechanism, according to some embodiments. The pumping mechanism includes the doser 130, doser plunger 131, sleeve 171, sleeve cover 173, and valve mechanism 160. The doser 130 includes the doser wall 1334 and doser cavity 1333. The doser 130 is rigidly connected to the sliding needle 140 and the doser cavity 1333 is in hydraulic communication with the sliding needle 140. The doser plunger 131 includes the doser piston 132, doser gasket 134, and scraper spring 175. The sleeve 171 and sleeve cover 173 form a cylinder that has a proximal end 1771 and a distal end 1772. The sleeve cover has a protrusion 174. The valve mechanism 160 includes the inlet chamber 161, exhaust chamber 162, front spacer 163, back seal 164, back spacer 165, and front seal 166. The exhaust chamber 162 is in hydraulic communication with the second conduit 151. The RP-DP O-ring 170 circumvents the sleeve 171 and provides sealing of the RP sealed compartment after RP-DP connection (FIG. 11 and FIG. 24). The doser 130 can be linearly displaced within the sleeve 171 and the doser plunger 131 can be linearly displaced within the doser 130. When the doser plunger 131 is situated at the most proximal position, the spring scraper 175 is engaged with the sleeve cover protrusion 174 (FIGS. 46-48).

FIGS. 61A-C and FIGS. 62A-C show cross sectional views of the doser 130 and valve mechanism 160 at the doser filling phase (FIGS. 61A-C), and the doser emptying phase (FIGS. 61A-C), according to some embodiments.

FIG. 61A shows the doser 130, doser plunger 131, sleeve 171, and valve mechanism 160. The doser 130 has a proximal end 1331 and a distal end 1332. The sleeve 171 has a proximal end 1771 and a distal end 1772. At the beginning of the doser filling phase, the doser 130 is situated at the most distal position within the sleeve 171 (1332 and 1772 are in contact, 1331 and 1771 are apart—light double head arrows), the doser plunger 131 is situated at the most distal position within the sleeve 171, and the sliding needle opening 144 is situated within the exhaust chamber 162. At this stage, the doser 130 is displaced in the direction of the dashed line arrow. FIG. 61B shows the doser 130 after displacement within the sleeve (1332 is positioned apart from 1772—light double head arrows, 1331 and 1771 are in contact), the sliding needle opening 144 is situated within the inlet chamber 161. At this phase, further displacement of the doser plunger 131 in the direction of the bold dashed line arrow linearly displaces the doser plunger 131 within the doser 130. FIG. 61C shows the doser plunger 131 after displacement within the doser 130 in the direction of the bold dashed line arrow. The doser plunger 131 is positioned apart from the doser distal end 1332 (light double head arrows). The movement of the doser plunger 131 within the doser 130 displaces insulin in the direction of the bold dashed line arrow and consequently filling the doser 130.

FIG. 62A shows the doser 130 and doser plunger 131 at the beginning of the doser emptying phase. The doser 130 is situated at the most proximal position within the sleeve 171 (1331 and 1771 are in contact, 1332 and 1772 are apart—light double head arrows), the doser plunger 131 is situated at the most proximal position within the doser 130, and the sliding needle opening 144 is situated within the inlet chamber 161. At this stage, the doser 130 is displaced in the direction of the dashed line arrow. FIG. 62B shows the doser 130 after displacement within the sleeve 171 in the direction of the bold dashed line arrow. The doser proximal end 1331 is positioned apart from the sleeve proximal end 1771 (light double head arrows), the doser distal end 1332 and the sleeve distal end 1772 are in contact, and the sliding needle opening 144 is positioned within the exhaust chamber 162. FIG. 62C shows the doser plunger 131 after displacement within the doser 130 in the direction of the bold dashed line arrow. The doser plunger 131 is positioned apart from the doser proximal end 1331. The movement of the doser plunger 131 within the doser 130 displaces insulin in the direction of the bold dashed line arrow and consequently emptying the doser 130.

FIGS. 63A-B show magnified cross sectional views of the valve mechanism 160 at the doser filling phase (FIG. 63A) and the doser emptying phase (FIG. 63B), according to some embodiments. The valve mechanism 160 includes the inlet chamber 161, exhaust chamber 162, front spacer 163, back seal 164, back spacer 165, and front seal 166. During the doser filling phase (FIG. 63A), the doser 130 distal end is apart from the sleeve 171 distal end (bold dashed line double arrows) and the sliding needle opening 144 is situated within the inlet chamber 161. During the doser emptying phase (FIG. 63B) the doser 130 distal end is in contact with the sleeve 171 distal end and the sliding needle opening 144 is situated within the exhaust chamber 162.

FIGS. 64A-B shows cross section (FIG. 64A) and spatial (FIG. 64B) views of the sliding needle 140), according to some embodiments. The sliding needle includes the proximal end 141, distal end 142, and opening 144. The proximal end is in hydraulic communication with the doser cavity. The distal end is blinded and has a sharp tip. In some embodiments, there are two sliding needle openings. In some embodiments, one or more openings are provided.

Figure 65:
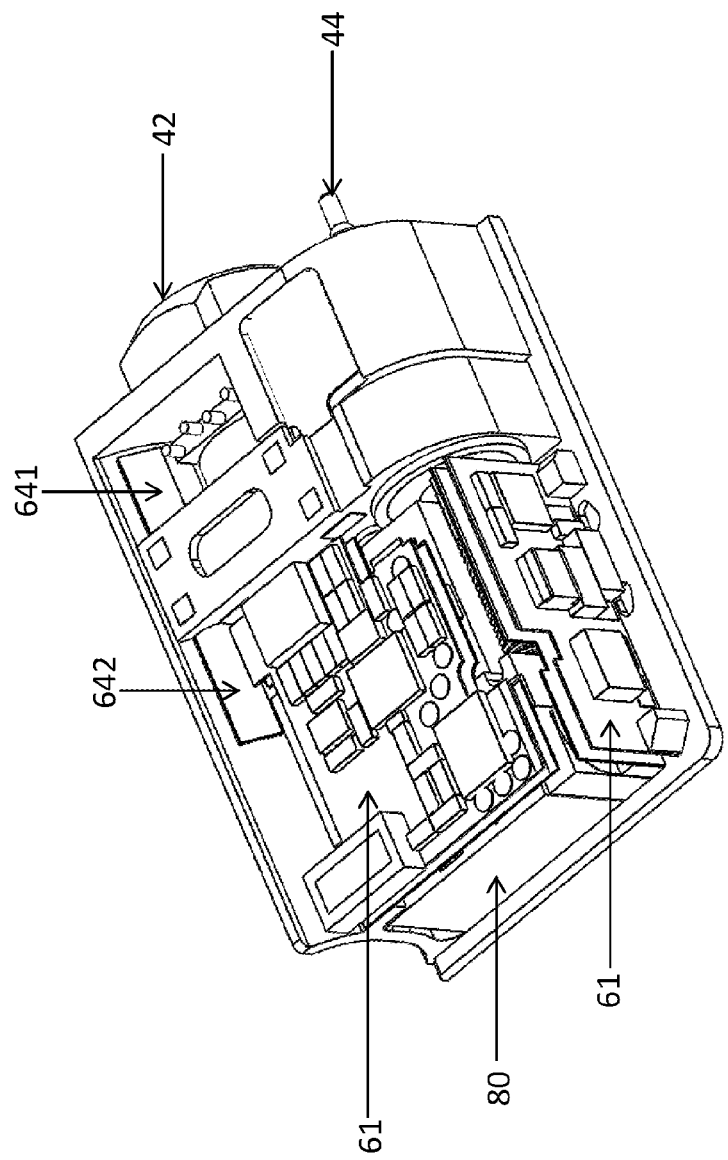
FIGS. 65-67 show the hardware components and the hardware operation modes, according to some embodiments.
Figure 66:
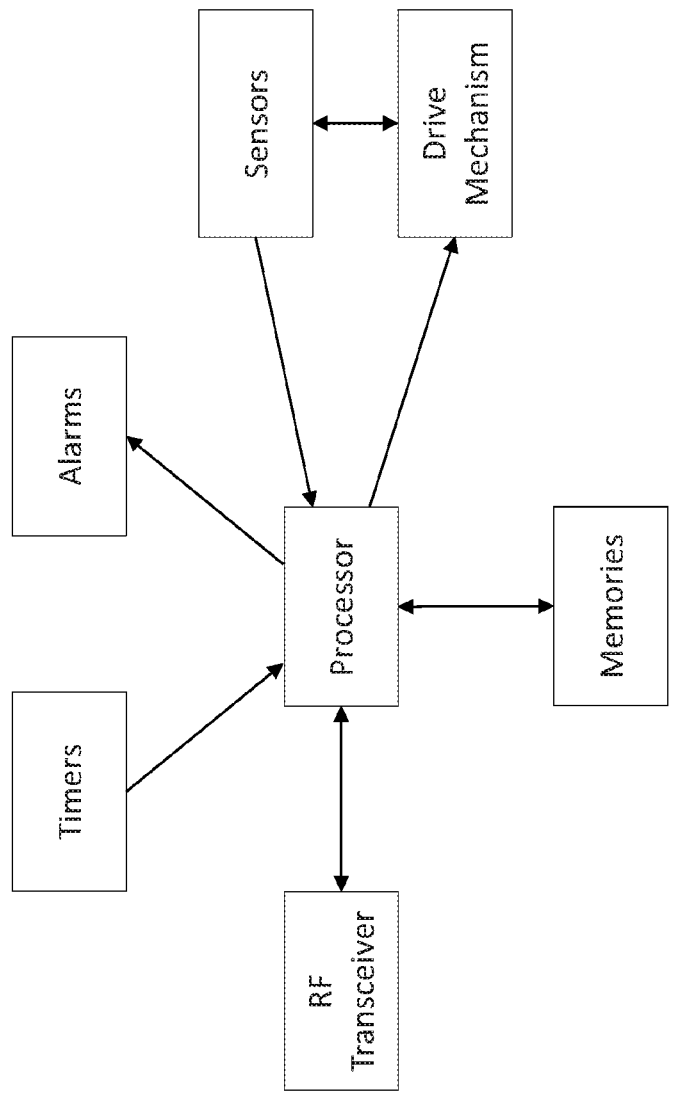
Figure 67:
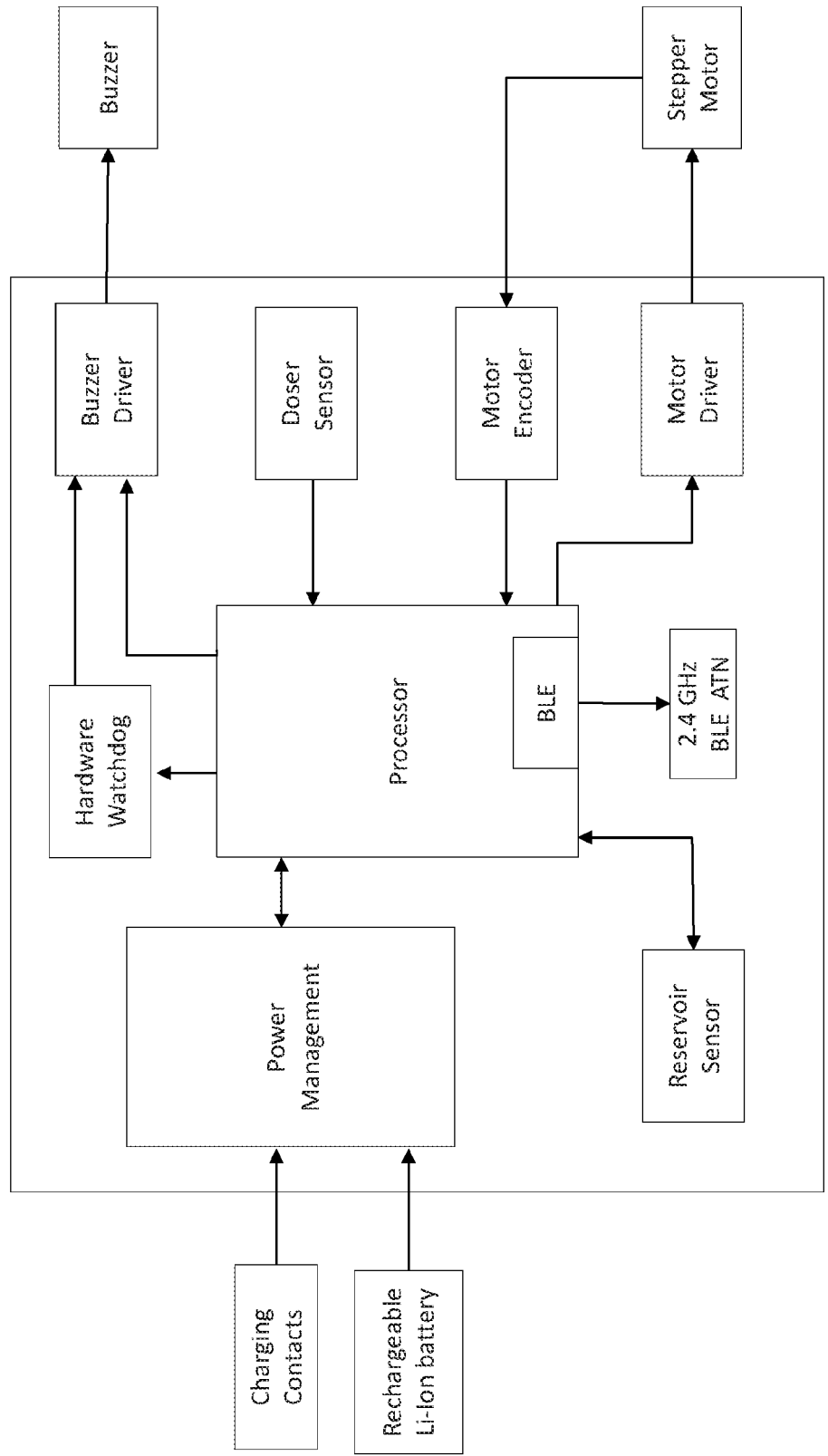

FIGS. 65-67 show the hardware components and the hardware operation modes, according to some embodiments. For example, in some embodiments, FIG. 65 shows a spatial view of the hardware components of the RP (RP cover 25 removed, FIG. 7). The hardware includes the PCB 61 (folded) and battery 80. The PCB 61 comprises the various electronic components (i.e. microprocessor, transceiver, sensors, etc.). Some of the RP components are shown including the motor 42, lead screw 44, and the sockets of the reservoir sensor 641 and 642.

FIG. 66 shows the hardware state machine, according to some embodiments. The processor commands the driving mechanism, receives inputs from the sensors (i.e. encoder sensor), and accordingly, adjust the driving mechanism operation. The processor receives inputs from the timers (i.e. RTC), memories, and RF transceiver and delivers alarms/alerts outputs. There are two ways communication between the processor the memories, and transceiver and between the sensors and driving mechanism.

FIG. 67 shows a block diagram of the hardware, according to some embodiments. The processor receives inputs from the sensors (encoder sensor, doser sensor, and reservoir sensor) and controls the motor driver, power management, watchdog, buzzer driver, and BLE antenna. The motor driver operates the motor (i.e. stepper motor) and the encoder. The processor receives inputs from the encoder and accordingly adjusts motor operation. The battery (e.g., Li. Ion) is charged by the external power through the charging contacts.

Figure 69:
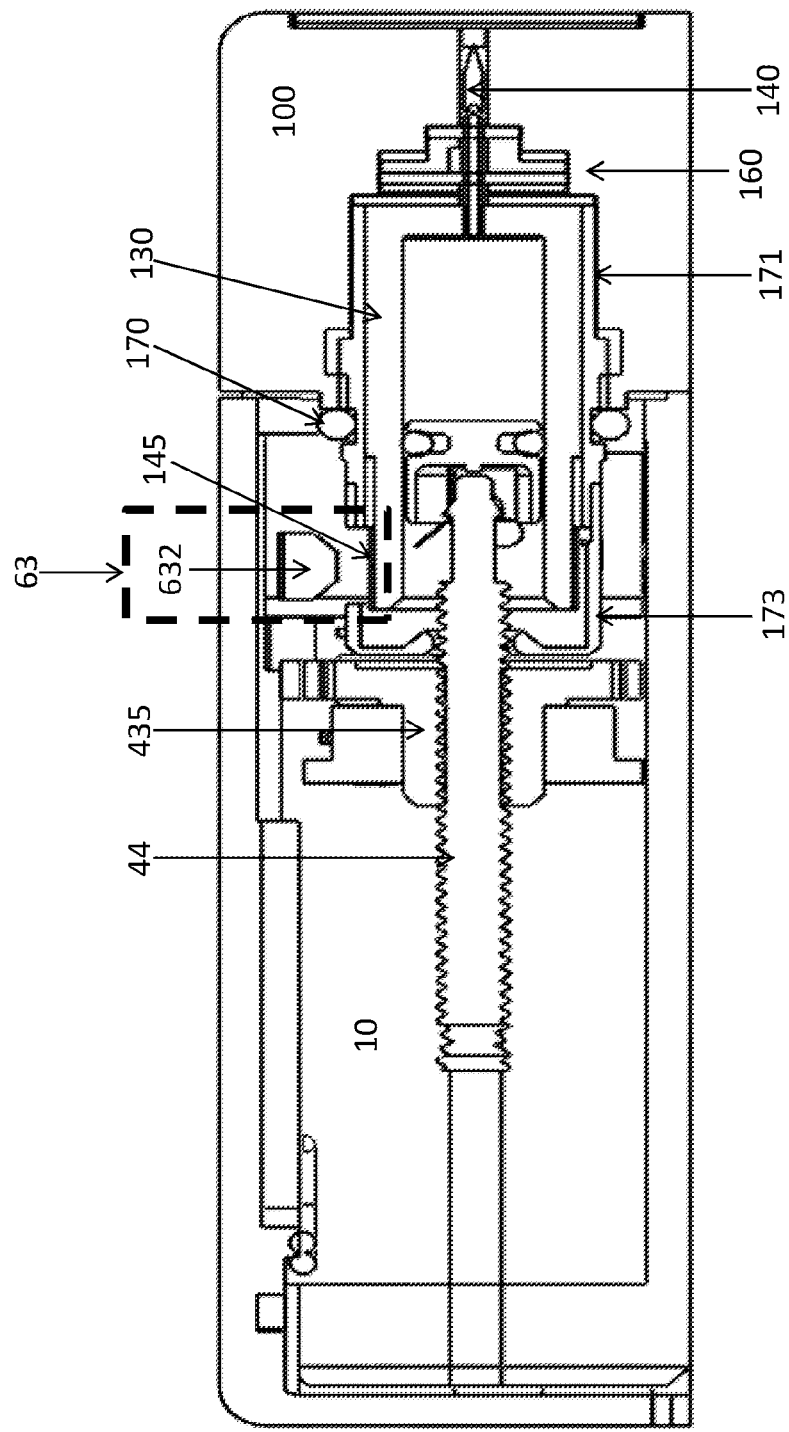

FIGS. 68-70 show the components and operation modes of the doser sensor 63, according to some embodiments. The doser sensor 63 detects relative movements between the doser 130, and the sleeve 171, doser 130 positions at the end of doser filling phase and doser emptying phase, and RP-DP connection and disconnection. The doser sensor 63 may provide occlusion detection during motor operation if during the doser emptying phase (FIG. 56) there is a relative movement between the doser 130 and the sleeve 171 instead of relative movement between the doser plunger 131 and the doser 130.

FIGS. 68A-C show schemes of the doser sensor 63 operation modes, according to some embodiments. The doser sensor 63 is comprised of a reflective photo-micro-detector 632 ("detector") and the doser sticker 145 that is adhered to the doser 130. Inputs from the detector 632 (voltage) are processed by the micro-processor that controls motor operation (i.e. direction of revolution), or provides alerts and alarms. The doser sticker 145 comprises a barcode. In some embodiments, the barcode includes two zones—black and white. The barcode can be comprised of bars at various widths, any protruding structure, or any other configuration that can be detected by the detector 632. FIG. 68A and FIG. 68B show the doser sensor operation during the pump operation cycle (doser filling phase and doser emptying phase). When the doser 130 is displaced forward and backward in the directions of the bold dashed line arrows, the doser sticker 145 is displaced in the same direction and the photo-micro-detector 632 is accordingly aligned with the white (FIG. 68A) or black (FIG. 68B) barcode. The change in light reflectance (light dashed arrows) is converted by the detector 632 to a change in current and change in voltage. During doser 130 displacement (black to white conversion), the current is gradually increased (gradual increase in light reflectance). During doser 130 displacement (white to black conversion), the current is gradually decreased (gradual decrease in light reflectance). When the doser 130 displacement is stopped (in both directions), the current (and voltage) remains constant which is interpreted by the processor 62 as no doser 130 movement. When the doser 130 displacement is stopped (both directions), further displacement of the doser plunger (FIGS. 55-56) displaces insulin into the doser (doser filling phase) or from the doser (doser emptying phase). During doser emptying phase, the exact amount of displaced insulin (insulin delivery volume—insulin units) is derived from calculating the number of gear revolutions (encoder sensor, FIGS. 9-10) beginning immediately after the doser displacement is stopped and the doser plunger displacement within the doser is start (FIGS. 55-56). FIG. 68C shows the operation of the doser sensor 63 during RP—DP disconnection. The RP 10 includes the photo-micro-detector 632 and the processor 62. The DP 100 includes the doser 130 and doser sticker 145. When the RP 10 and DP 100 are disconnected (displacement in the direction of the bold dashed line arrow) the photo-micro-detector 632 receives no light reflection (light dashed arrows), the input is received by the processor and interpreted as RP-DP disconnection. During RP-DP connection (not shown), the alignment of the detector 632 with the sticker 145 barcode is detected and interpreted as RP-DP connection.

FIG. 69 shows a cross sectional view of the doser sensor 63 (dashed line rectangular) and the main components of the RP and DP, according to some embodiments. The RP 10 includes the lead screw 44, rotating nut 435, and the photo-micro-detector 632. The DP 100 includes the doser 130, doser sticker 145, sleeve 171, valve mechanism 160, and sliding needle 140. The doser sensor 63 (dashed line rectangular) is comprised of the photo-micro-detector 632 and the doser sticker 145.

FIGS. 70A-E shows cross section views of the doser sensor 63 during pump operation and during RP-DP disconnection, according to some embodiments. For example, in some embodiments, FIG. 70A (doser emptying phase) and FIG. 70B (doser filling phase) show the doser sensor 63 (dashed line rectangular), doser 130, sleeve 171, and lead screw 44. The doser sensor 63 is comprised of the photo-micro-detector 632 and the doser sticker 145. Displacements of the doser 130 and the doser sticker 145 in forward and backward directions (bold dashed line arrows) are detected by the photo-micro-detector 632 and accordingly the relative position of the doser 130 (relative to the sleeve 171 and the RP 10) is precisely defined by the detector 632 and accordingly interpreted by the processor. FIGS. 70C-E show consecutive stages of RP-DP disconnection, the RP is displaced in the direction of the bold dashed line arrow. FIG. 70C shows the first stage of RP-DP inadvertent disconnection, the doser plunger 131 is in mid position within the doser 130 and the detector 632 is aligned with the doser sticker 145. FIG. 70D shows the next consecutive stage of RP-DP disconnection, the doser plunger 131 is further displaced in the direction of RP displacement (bold dashed line arrow) and the detector 632 is misaligned with the doser sticker 145. FIG. 70E shows the completion of RP-DP disconnection, the doser plunger 131 is in contact with the sleeve cover 173, the lead screw 44 is disengaged from the doser plunger 131, and the detector 632 is misaligned with the doser sticker 145. During RP-DP connection (RP displacement in the opposite direction), the lead screw 44 is engaged with the doser plunger 131, the detector 632 is aligned with the doser sticker 145, reflected light is detected by the detector 632 and the detector output (voltage) is interpreted by the processor as connection between RP and DP.

Figure 71:
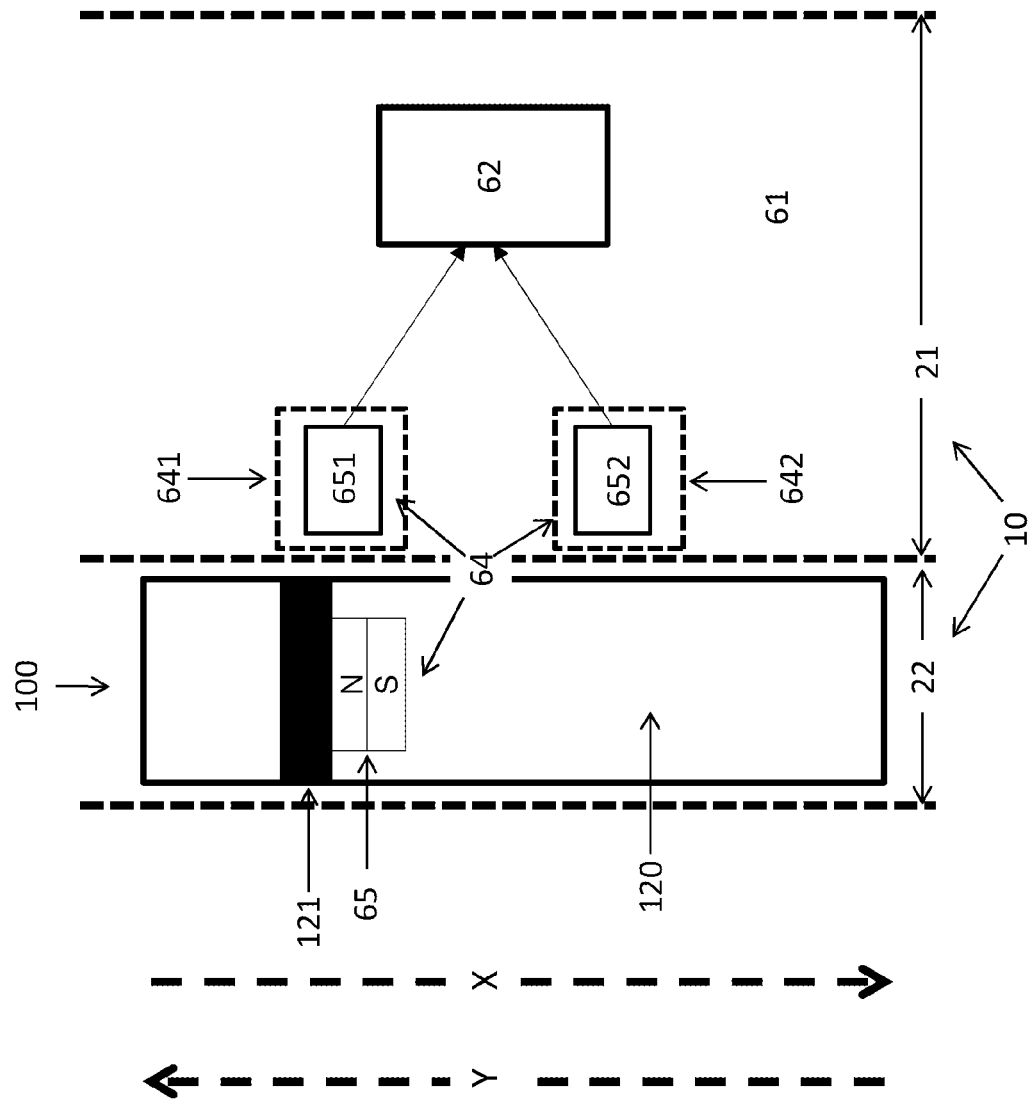
FIGS. 71-73 show the components and operation modes of the reservoir sensor, according to some embodiments.

FIG. 71 shows a scheme of the components of the reservoir sensor 64, the locations of the reservoir sensor 64 components, and the operation modes of the reservoir sensor 64, according to some embodiments. FIG. 71 shows the RP 10 compartments including the vented compartment 22 and the sealed compartment 21 (FIG. 11). The sealed compartment 21 includes the PCB 61 that includes the processor 62, the hall sensor one 651, and the hall sensor two 652. The hall sensor one 651 is situated within the reservoir sensor socket one 641 and the hall sensor two 652 is situated within the reservoir sensor socket two 642 (FIG. 65). The first reservoir 120 and first reservoir plunger 121 are parts of the DP 100. When the RP 10 and the DP 100 are connected, the first reservoir 120 (part of the DP 100) is situated within the vented compartment 22 of the RP 10 (FIG. 11). In some embodiments, the reservoir sensor 64 includes an axial pole magnet 65 and two hall sensors, hall sensor one 651 and hall sensor two 652. In some embodiments, the magnet can be radial, rectangular or circular. The axial pole magnet 65 is rigidly attached to the first reservoir plunger 121 which is situated within the first reservoir 120. The hall sensor one 651 and hall sensor two 652 are situated in close proximity to the first reservoir 120. The hall sensor is a transducer that varies its output voltage in response to a magnetic field. The hall sensors one and two 651 and 652 operate as analog transducers, directly returning a voltage. With a known magnetic field, their distance from the axial pole magnet 65 can be determined. Using two or more sensors, the relative position of the axial pole magnet 65 can be deduced. The output of both hall sensors 651 and 652 is received and processed by the processor 62 and transmitted to the controller. The axial pole magnet 65 is displaced (along the first reservoir plunger 121) within the first reservoir 120 during first reservoir 120 filling and during pump operation (backward and forward in the direction of the bold dashed line arrows X and Y respectively). The reservoir sensor 64 can provide one or more of the following data points: 1—exact or substantially exact amount of insulin in the first reservoir 120; 2—volume of insulin exceeding a minimal threshold (e.g., about 50 units, about 40 units, about 30 units, including values there between)—the first reservoir plunger 121 is displaced in the direction of the bold dashed line arrow X beyond a predetermined point; 3—the pumping mechanism is properly functioning—during the doser filling phase the first reservoir plunger 121 is displaced in the direction of the bold dashed line arrow Y; 4—amount of remaining insulin left in the first reservoir 120; and 5—volume of insulin is below a minimal threshold—provides low insulin level alert. In some embodiments, more than two, three, four, five, etc., hall sensors are provided.

Figure 72:
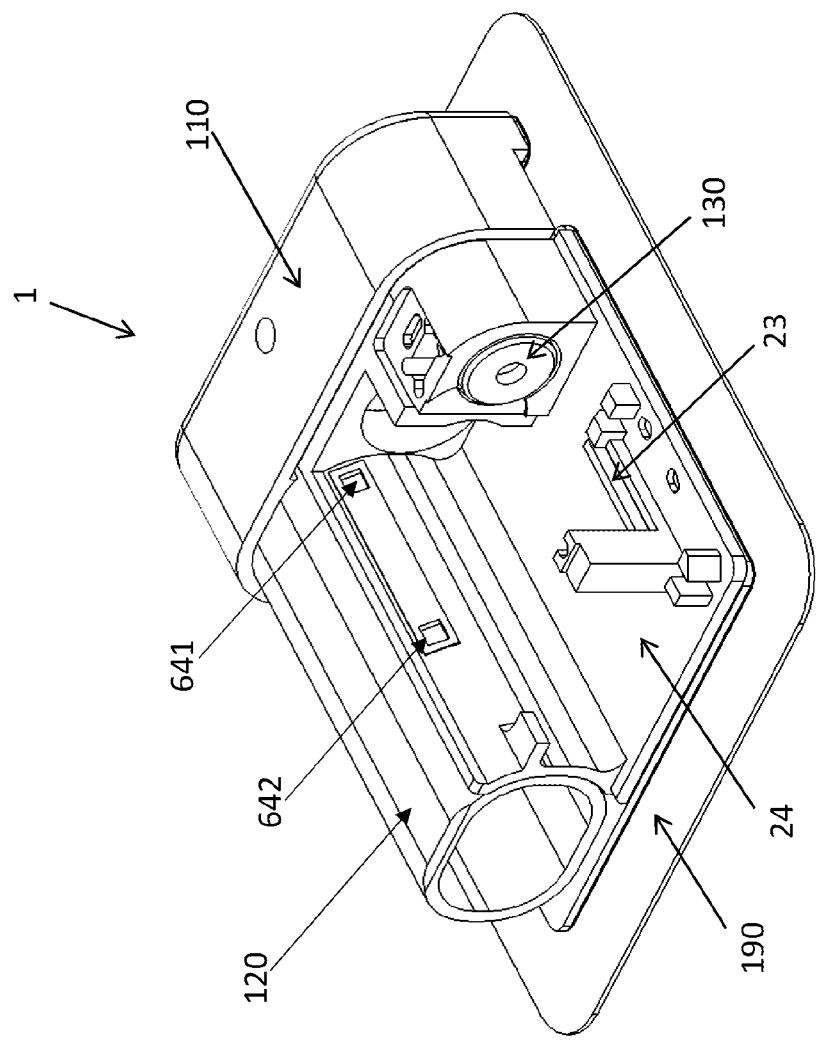

FIG. 72 shows a spatial view of some components of the patch pump I and the positions of the reservoir sensor sockets 641 and 642, according to some embodiments. The patch pump 1 includes the RP that includes the RP base 24, bottom RP groove 231, reservoir sensor socket one 641, and reservoir sensor socket two 642. The DP includes the DP housing 110, first reservoir 120, doser 130, and adhesive base 190. After RP-DP connection the reservoir 120 is in close proximity with the reservoir sensor sockets 641 and 642.

Figure 73:
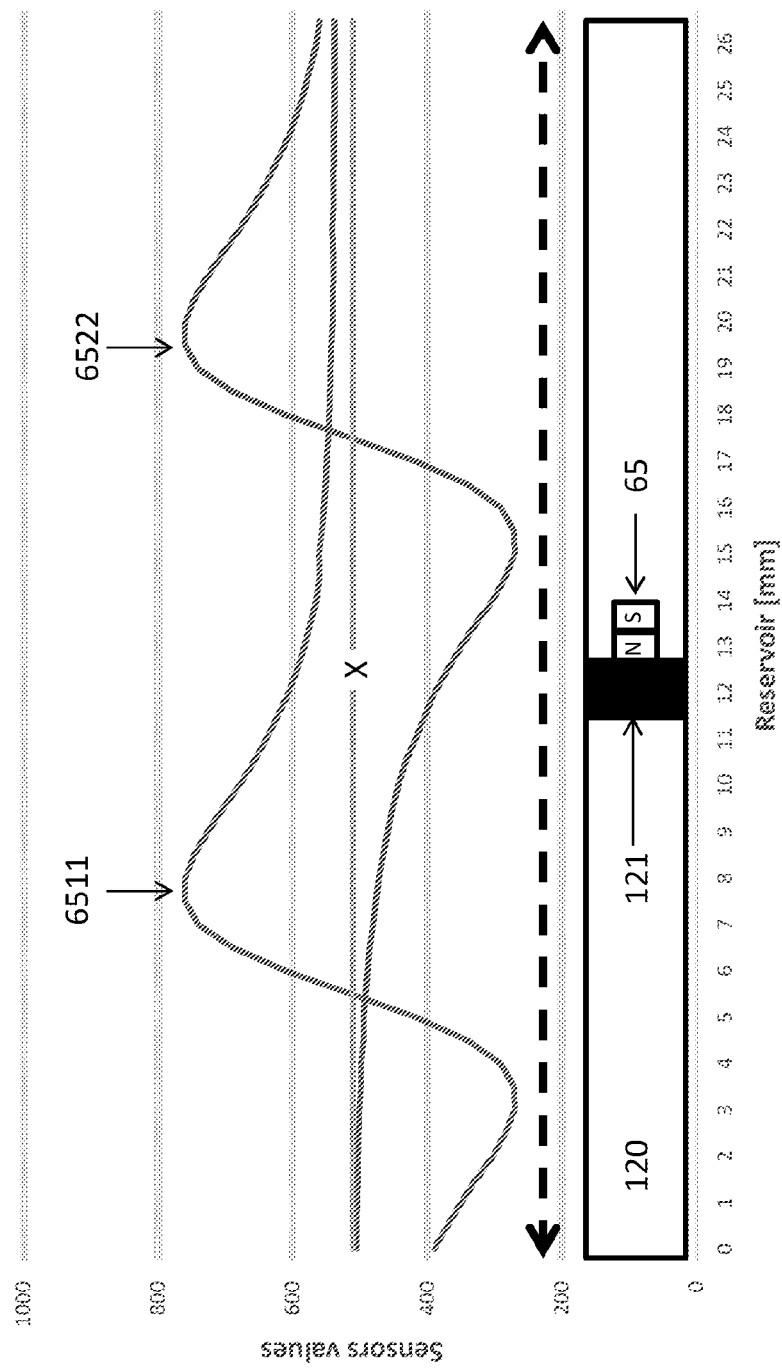

FIG. 73 shows a graphical diagram of example outputs of the reservoir hall sensors 651 and 652, according to some embodiments. The reservoir hall sensor outputs were measured during displacement of the first reservoir plunger 121 and the axial pole magnet 65 within the first reservoir 120 in the directions of the bold dashed line double arrow. The curved lines 6511 and 6522 show the outputs of the reservoir hall sensors 651 and 652 relative to a reference value line (X), in some embodiments. The precise location of the first reservoir plunger 121 (in millimeters from point zero) within the first reservoir 120 can be determined by deduction of the measured values (i.e. current or voltage) of both reservoir hall sensors 651 and 652.

FIGS. 74-83 show the components and the operation modes of air bubbles protection means, according to some embodiments. Air bubbles can enter into the first reservoir during filling (if air is not properly purged from the filling syringe) or during pump operation. During the doser filling phase, the doser plunger is displaced (FIG. 55) and creating a negative pressure within the entire fluid manifold (doser, conduits and first reservoir) fluid (e.g., insulin) is displaced from the first reservoir to the doser following the negative pressure gradient. The pressure gradient between the atmosphere and the relative negative pressure within the first reservoir (versus the atmosphere) forces air movement, through the first reservoir plunger gaskets, into the first reservoir cavity and potentially forming air bubbles within the first reservoir fluid. The air bubbles protection means include passive protection means (FIGS. 74-75)—barriers to air entry into the first reservoir through the first reservoir plunger gaskets, and active air bubbles protection means (FIGS. 76-83)—avoiding the pressure gradient between the atmosphere and the first reservoir cavity. Pressure equilibrium or reversed pressure gradient (pressure in the first reservoir is higher than the atmosphere) can be achieved by actively increasing the pressure in the first reservoir to atmospheric or above atmospheric pressure.

Figure 74:
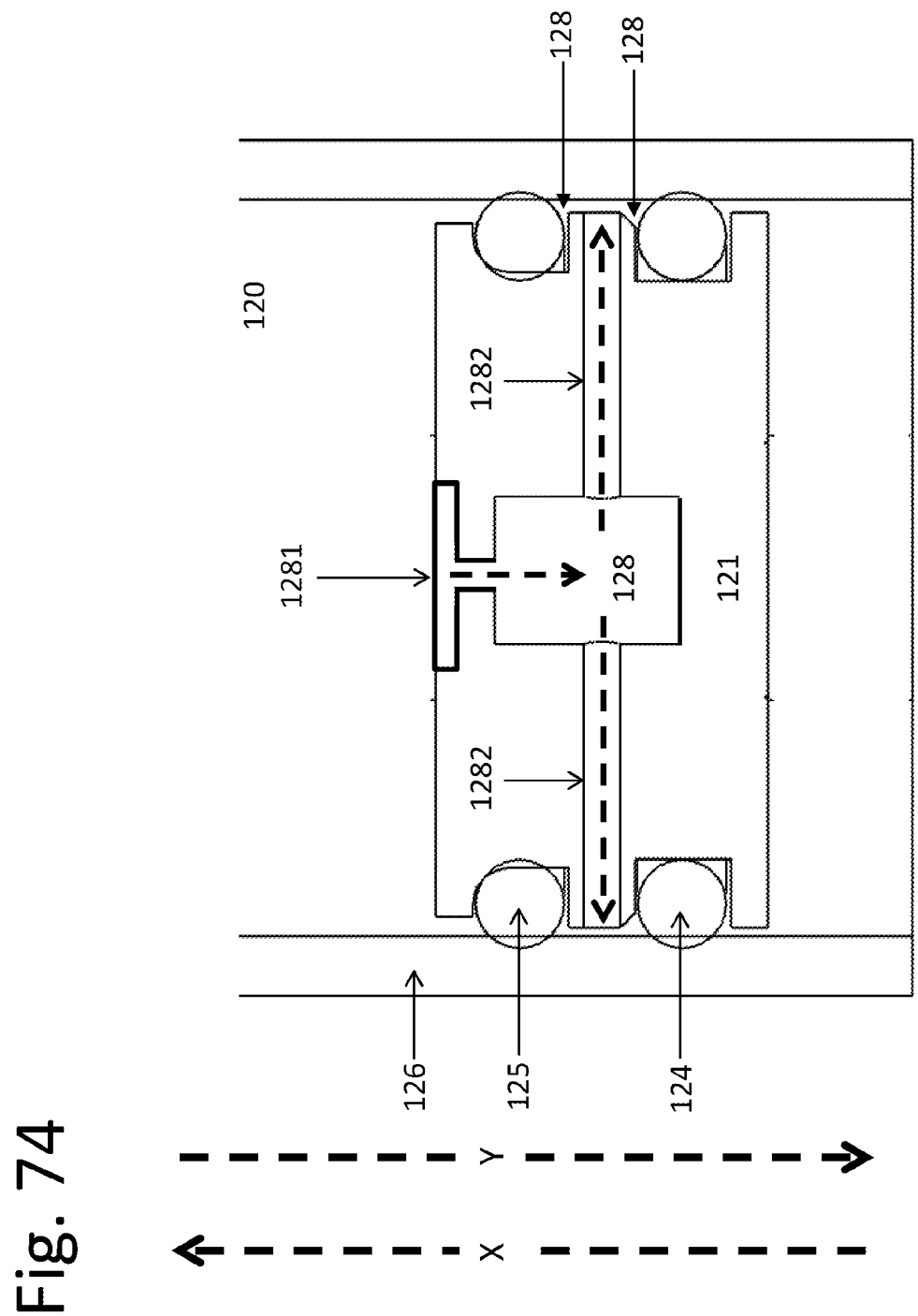

FIG. 74 shows a transverse cross section view of the components and principle of operation of a passive air bubble protection means—oil 128 between the first reservoir plunger gaskets 124 and 125, according to some embodiments. Oil 128 between the gasket forms a barrier to air entry by hermetically occluding all potential creases in the first reservoir wall 126 and potential deformities and protrusions (i.e. parting line) in the gaskets 124 and 125. The oil 128 can be introduce between the gaskets 124 and 125 in the following options: 1—assembly of gaskets 124 and 125 over the first reservoir plunger 131 in a container filled with oil, 2—injecting oil through the oil filling septum 1281 and through the oil filling channels 1282, 3—providing negative pressure before oil filling. The injected oil 128 is delivered in the direction of the light dashed arrows and introduced into the space between the gaskets 124 and 125. The oil 128 between the gasket remains in place during first reservoir filling (direction of bold dashed line arrow X) and during pump operation (direction of bold dashed line arrow Y), in addition to sealing, the oil 128 facilitates smooth displacement of the first reservoir plunger 121 and gaskets 124 and 125.

Figure 75:
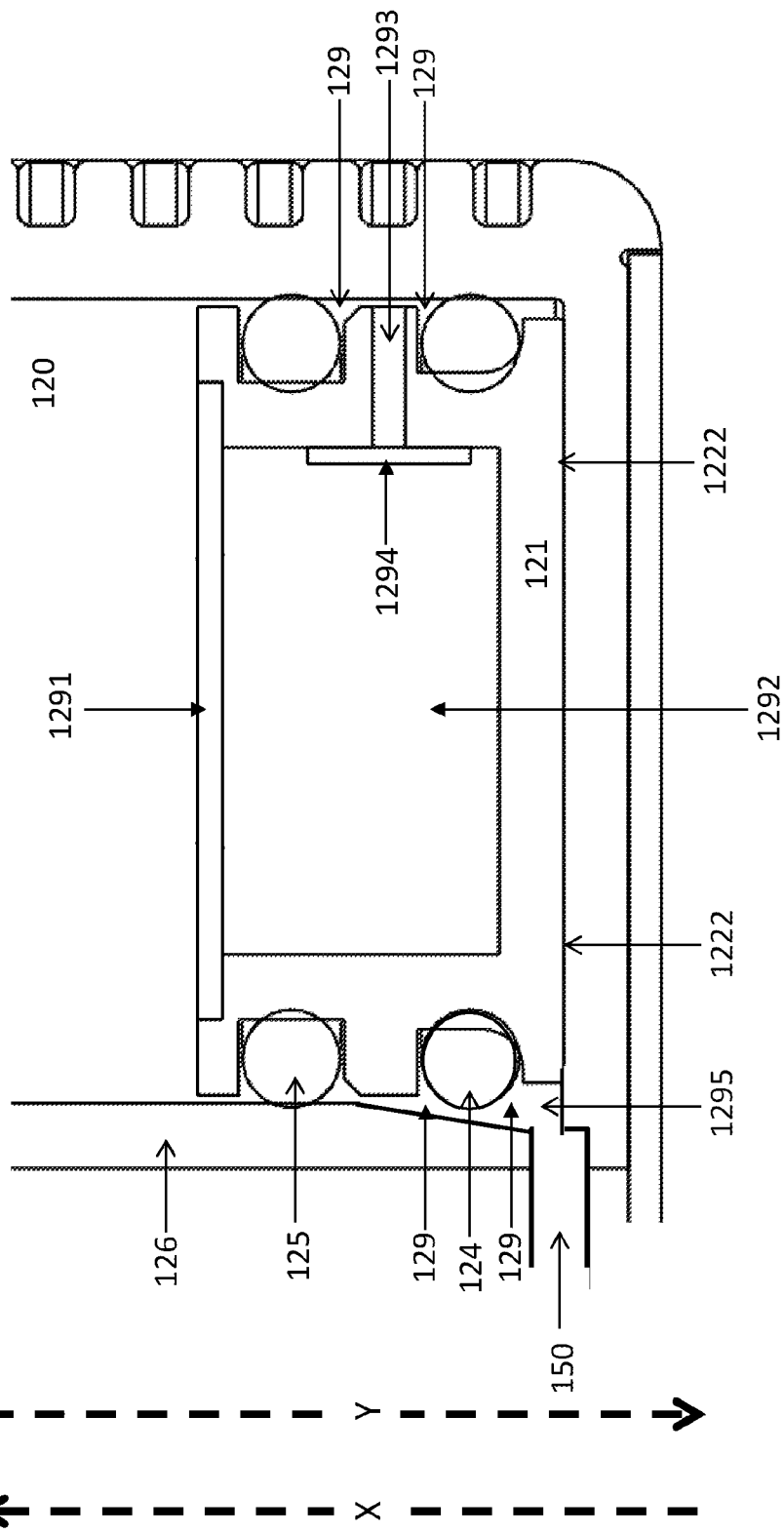

FIG. 75 shows a transverse cross sectional view of the components and principles of operation of another passive air bubble protection means—drug (e.g., insulin) 129 between the first reservoir plunger gaskets 124 and 125, according to some embodiments. The air bubble protection barrier is the drug 129 that is delivered by the patch pump—insulin or any other therapeutic fluid. FIG. 75 shows the first reservoir 120, first reservoir wall 126, first reservoir plunger 121, first reservoir gaskets 124 and 125, first reservoir filling cavity 1295, first conduit 150, top membrane 1291, air cavity 1292, fluid resistor 1293, unidirectional gate 1294, and insulin 129. The first reservoir filling cavity 1295 has a shape of a half conus, or any other cavity that allows the drug to pass from 150 to 1293, and it is formed by scraping the first reservoir wall 126 at the most distal end

1222. The first reservoir filling cavity 1295 is in hydraulic communication with the first conduit 150. During first reservoir 120 filling, insulin 129 is delivered through the first conduit 150 into the first reservoir filling cavity 1295 and occupies the space between the gaskets 124 and 125. Air, that was trapped between the gaskets before filling is forced through the fluid resistor 1293 and the unidirectional gate 1294 into the air cavity 1292 and from the cavity 1292 through the top membrane 1291 to the atmosphere. The fluid restrictor 1293 is a micro channel that provides air passage and prevents or restrict fluid passage. The unidirectional gate 1294 can be made of any semipermeable material (e.g., Gore-Tex® material) or any other elastomer that is pressed against the aperture (i.e. duck valve) and provides further protection against fluid passage. The top membrane 1291 serves as a second line of defense if the unidirectional gate 1294 is failed. When the first reservoir filling cavity 1295 and the space between the gaskets 124 and 125 is fully occupied by insulin 129, further injection of insulin 129 into the first reservoir forces a displacement of the first reservoir plunger 121 in the direction of the bold dashed line arrow. When the first reservoir plunger 121 is displaced in the direction of the bold dashed line arrow X (reservoir filling), the first gasket 124 is adhering to the reservoir wall 126 and a double sealing (by both gaskets) is provided. The double sealing is provided along the entire length of the first reservoir plunger 121 displacement within the first reservoir 120 in the direction of the dashed line arrow X (reservoir filling) and the direction of the dashed line arrow Y (pump operation).

FIGS. 76-83 show the components and operation modes of active air bubbles protection means, according to some embodiments. The negative pressure in the manifold (reservoirs, conduits, and chambers) at the end of the doser filling phase is elevated to above atmospheric pressure (P+) by returning back a defined fluid quantum into the manifold. This can be achieved by locking the doser 130 at the beginning of the doser emptying phase and avoiding the relative doser displacement (relative to the sleeve) and displacement of the sliding needle opening from the inlet chamber to the exhaust chamber (FIGS. 55-56). Further doser plunger 131 displacement, when the doser 130 is locked, displaces insulin in the direction of the first reservoir 120 (reverse flow direction). The insulin quantum that enters the first reservoir 120 increases the pressure within the first reservoir 120 above atmospheric pressure (P+). The amount of pressure elevation in the first reservoir 120 depends on the predetermined quantum that is delivered back into the first reservoir and the amount of trapped air bubbles within the reservoir.

Figure 77B:
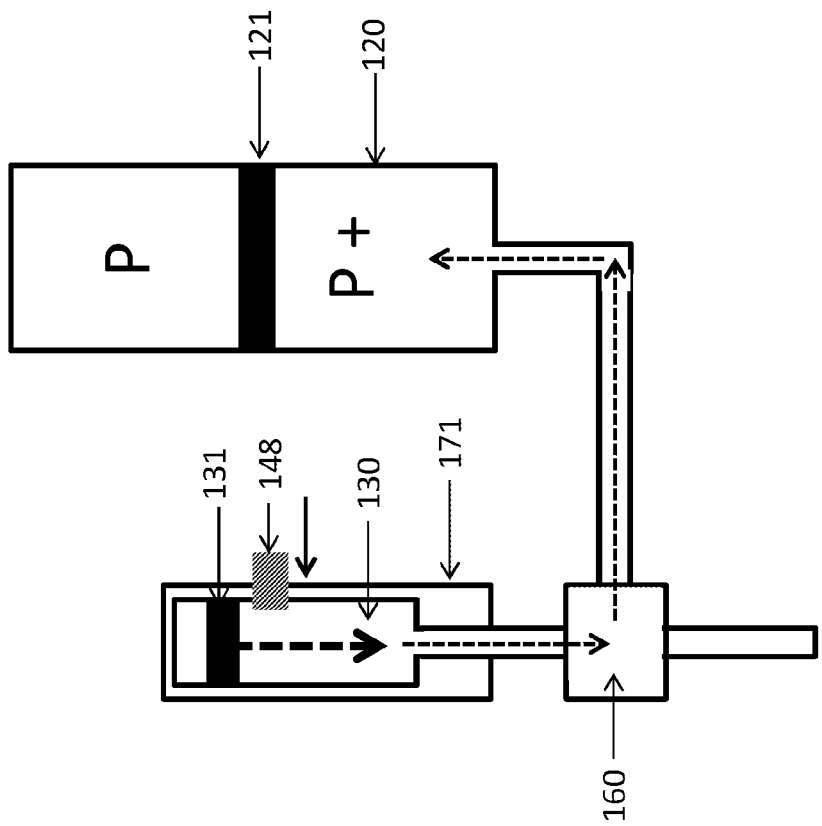
Figure 77A:
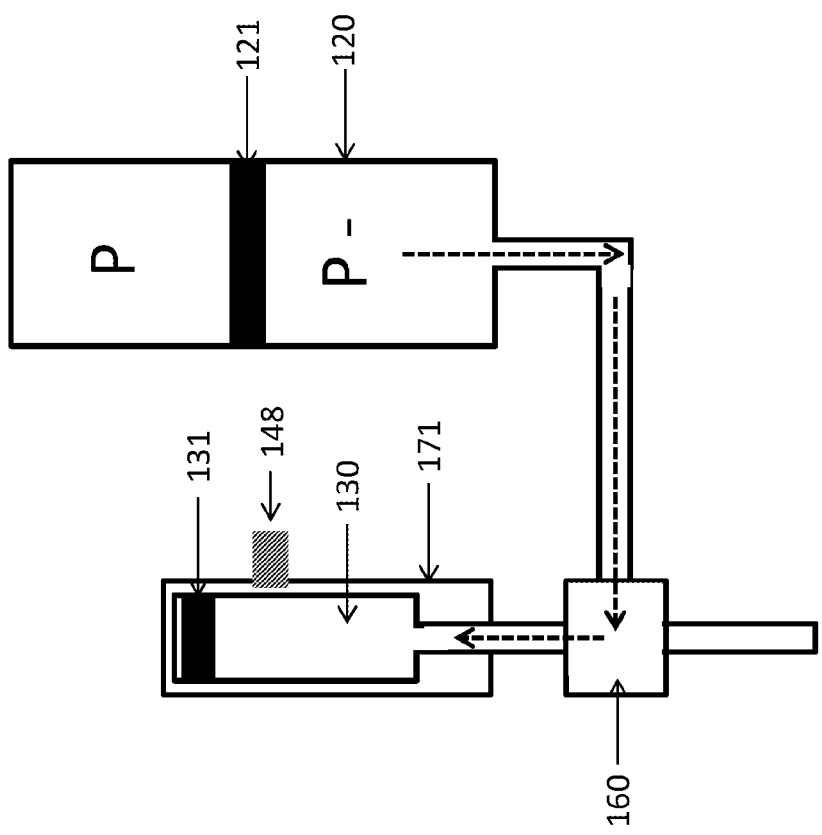
Figure 79:
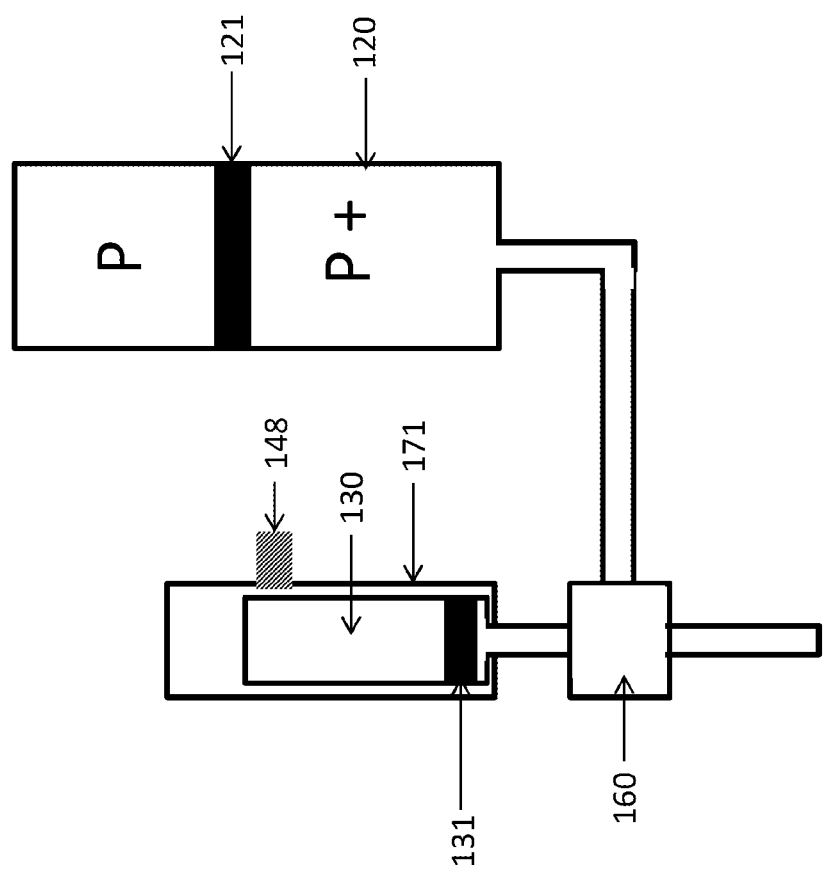

FIGS. 76A-B, 77A-B, 78A-B, and 79 show schemes of the doser locking mechanism during the various phases of the pumping mechanism operation cycle, according to some embodiments. The schemes include some of the components of the pumping mechanism including the first reservoir 120, first reservoir plunger 121, doser 130, doser plunger 131, doser locker 148, sleeve 171, and valve mechanism 160. Doser 130 is displaced in the direction of the bold dashed line arrow to the left of the doser 130, doser plunger 131 is displaced in the direction of the bold dashed line arrow within the doser 130, doser locker 148 is displaced in the direction of the bold continuous line arrow, and insulin is displaced in the direction of the light dashed line arrows. FIG. 76A shows the first phase of the doser filling phase, the pressure within the first reservoir is equal to the atmospheric pressure (P). At the beginning of the doser filling phase, the doser 130 is displaced in the direction of the bold dashed line arrow and the sliding needle opening (not shown) is displaced from the exhaust chamber to the inlet chamber (FIG. 55). FIG. 76B shows the end of the doser 130 displacement within the sleeve 171. At this stage, the doser plunger 131 is displaced within the doser in the direction of the bold dashed line arrow and insulin is displaced from the first reservoir 120 to the doser 130 in the direction of the light dashed line arrows. The pressure in the first reservoir 120 is decreased below the atmospheric pressure (P−). FIG. 77A shows the end of the doser filling phase, the doser plunger 131 is reaching the most proximal position within the doser 130, insulin filling (in the direction of the light dashed line arrows) is completed, and the pressure within the first reservoir 120 is negative (P−). FIG. 77B shows the beginning of the doser emptying phase. Before initiation of displacement of the doser plunger 131 in the direction of the bold dashed line arrow, the doser locker 148 is displaced in the direction of the bold continuous line arrow. Following displacement of the doser locker 148, the doser locker 148 is engaged with the doser 130 and displacement of the doser is restricted. Further displacement of the doser plunger 131 within the doser 130 displaces insulin in the direction of the light dashed line arrows, back into the first reservoir 120. The pressure in the first reservoir 120 is increased above the atmospheric pressure (P+). FIG. 78A shows the continuation of the reservoir emptying phase. The doser locker 148 is displaced in the direction of the bold continuous line arrow, releasing the locking of the doser 130. The doser 130 is displaced within the sleeve 171 and the sliding needle opening is displaced from the inlet chamber to the exhaust chamber (not shown, see FIG. 56). The pressure within the first reservoir is positive (P+). FIG. 78A shows the next stage of reservoir emptying phase. The doser plunger 131 is displaced in the direction of the bold dashed line arrow and insulin is delivered through the exit port (not shown) into the patient (light dashed line arrows). The pressure within the first reservoir 120 is above the atmospheric pressure (P+). FIG. 79 shows the end of the operation cycle. The doser 130 and the doser plunger 131 are located in the most distal position and a new operating cycle is beginning (FIG. 76A).

Figure 83:
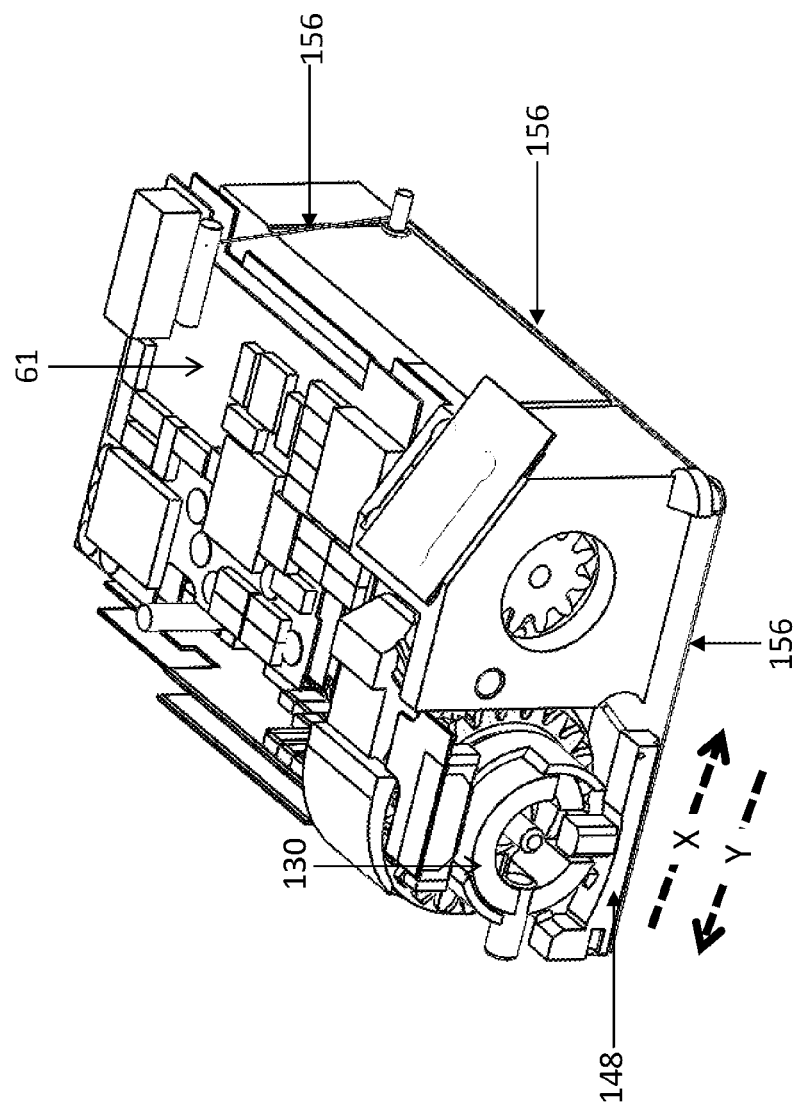

FIGS. 80-83 show some configurations of prefer embodiment of a doser locker, according to some embodiments. The doser locker can be displaced in one direction (locking doser displacement) or the opposite direction (unlocking doser displacement) by an actuator. The actuator can be of any kind known in the art such as nitinol wire, hydraulic, solenoid, piezo-electric, DC motor, etc. FIG. 80 shows an example of hydraulic actuator, and FIGS. 81-83 show examples of nitinol wire actuators. For example, in some embodiments, FIGS. 80A-B show cross section views of a hydraulic doser locking mechanism. FIG. 80 shows the first reservoir 120, motor 42, doser 130, doser locker 148, and doser locker conduit 149. The doser locker conduit 149 is in hydraulic communication with the first conduit (not shown) that communicates between the first reservoir and the inlet chamber. During the doser filling phase (FIG. 76B and FIG. 77A) the manifold pressure is decreased below atmospheric pressure (FIG. 80A). Following decrease in manifold pressure and decrease in pressure within the doser locker conduit 149, the doser locker 148 is displaced in the direction of the bold dashed line arrow, the doser locker 148 is engaged with the doser 130, and displacement of the doser 130 is restricted. At the initiation of the doser emptying phase (FIG. 77B) the manifold pressure and the pressure within the doser locker conduit 149 is increased above the atmospheric pressure (FIG. 80B), the doser locker 148 is displaced in the direction of the bold dashed line arrow, the doser locker 148 is disengaged from the doser 130, and the doser 130 can be freely displaced.

FIG. 81A-B shows cross sectional (FIG. 81A) and spatial (FIG. 81B) views of a mechanical doser locking mechanism—a spring locking mechanism, according to some embodiments. FIG. 81 shows the doser 130, doser plunger 131, DP-RP O-ring 170, sleeve cover 173, sleeve cover protrusion 174, scraper spring 175, sleeve spring locker 155, and sleeve spring locker notch 1555. The sleeve spring locker 155 is connected to the doser 130. During the doser filling phase, the doser is displaced in the direction of the bold dashed line X (FIG. 76B and FIG. 77A), when the tip of the sleeve spring locker 155 reaches the sleeve spring locker notch 1555, the doser 130 is locked and cannot be displaced. During the initiation of the doser emptying phase (FIG. 77B), the doser plunger 131 is displaced in the direction of the bold dashed line Y (FIG. 78A and FIG. 78B). When the doser plunger 131 is further displaced in the same direction, the doser scraper spring 175 is engaged with the doser locker spring 155, the doser locker spring 155 is twisted, the tip of the doer locker spring 155 is released from the sleeve spring locker notch 1555, and the doser 130 can be freely displaced.

FIGS. 82A-B show transverse cross sectional (FIG. 82A) and spatial (FIG. 82B) views of a doser locking mechanism that is based on a nitinol spring 157, according to some embodiments. FIGS. 82A-B show the doser 130, scraper spring 175, sleeve 171, PCB 61, doser locker 148, and nitinol spring 157. The doser spring 157 is made of nitinol—a nickel titanium shape memory alloy. In some embodiments, the spring can be made of any other shape memory alloy (e.g., flexinol, etc.). The nitinol spring 157 is connected at both sides to electrical wiring (not shown). When electrical current is delivered through the nitinol spring 157 its total length is shortened (due to inherent property of nitinol), the doser locker 148 is displaced in the direction of the bold dashed line arrow X, the doser locker 148 is engaged with the doser 130, and displacement of the doser 130 is restricted. When the electrical current is switched off, the nitinol spring 157 resumes its length, the doser locker 148 is displaced in the direction of the bold dashed line arrow Y, the doser locker 148 is disengaged from the doser 130, and the doser 130 can be freely displaced.

FIG. 83 shows a spatial view of a doser locking mechanism that is based on a nitinol wire 156, according to some embodiments. FIG. 83 shows the PCB 61, doser 130, doser locker 148, and nitinol wire 156. The nitinol wire 156 is connected at both sides to electrical wiring (not shown). When electrical current is delivered through the nitinol wire 156 its total length is shortened (due to inherent property of the nitinol wire), the doser locker 148 is displaced in the direction of the bold dashed line arrow X, the doser locker 148 is engaged with the doser 130, and displacement of the doser 130 is restricted. When the electrical current is switched off, the nitinol wire 155 resumes its length, the doser locker 148 is displaced in the direction of the bold dashed line arrow Y, the doser locker 148 is disengaged from the doser 130, and the doser 130 can be freely displaced.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

At least some of the embodiments disclosed above, in particular at least some of the methods/processes disclosed, may be realized in circuitry, computer hardware, firmware, software, and combinations thereof (e.g., a computer system). Such computing systems, may include PCs (which may include one or more peripherals well known in the art), smartphones, specifically designed medical apparatuses/devices and/or other mobile/portable apparatuses/devices. In some embodiments, the computer systems are configured to include clients and servers. A client and server are generally remote from each other and typically interact through a communication network (e.g., VPN, Internet). The relationship of client and server arises by virtue of computer programs running on the respective computers and having a client-server relationship to each other.

Some embodiments of the disclosure (e.g., methods and processes disclosed above) may be embodied in a computer program(s)/instructions executable and/or interpretable on a processor, which may be coupled to other devices (e.g., input devices, and output devices/display) which communicate via wireless or wired connect (for example).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A patch pump drug delivery device comprising:
    a reusable part (RP) including:
        a lead screw;
        a lead screw tip; and
        a reservoir cover;
        and
    a disposable part (DP) including:
        a reservoir having a proximal end and a distal end;
        a plunger having a proximal end and a distal end, wherein the distal end is in contact with a drug contained in the reservoir;
        a doser reservoir;
        a doser plunger;
        a flexible member integral with or connected to a proximal end of the doser plunger and including an opening for receiving and reversible connection with the lead screw tip;
        and
        a sleeve cover connected with the proximal end of the doser reservoir and including an opening for receiving and enabling reversible connection of the lead screw tip with the doser plunger, and having an internal edge arranged to face the flexible member,
    wherein
        upon connecting the RP with the DP, the sleeve cover and doser plunger are arranged at the proximal end of the doser reservoir such that the flexible member interacts with the internal edge of the sleeve cover to allow the flexible member to receive the lead screw tip within the opening of the flexible member, and as the doser plunger proceeds down the doser reservoir during use, the lead screw tip is connected to the doser plunger;
        and
        upon disconnecting the RP with the DP the sleeve cover and doser plunger are arranged at the proximal end of the doser reservoir, such that the flexible member interacts with the internal edge of the sleeve cover to allow the lead screw tip to be removed from within the opening of the flexible member.

2. The device of claim 1, further comprising an adhesive base.

3. The device of claim 2, wherein the adhesive base is configured as an integral component to the disposable part.

4. The device of claim 1, further comprising an inserter.

5. The device of claim 4, wherein the inserter comprises an inserter housing having an opening in a side thereof to receive at least the DP.

6. The device of claim 4, wherein the inserter comprises an inserter housing having an opening in a side thereof to receive the connected RP and DP.

7. The device of claim 1, wherein the RP further comprises a housing and at least two compartments.

8. The device of claim 7, wherein the at least two compartments includes a vented compartment and a sealed compartment.

9. The device of claim 4, wherein the inserter includes a housing, a trigger, at least one safety catch, and an opening for receiving at least the DP.

10. The device of claim 1, wherein the RP further comprises a housing comprising cover and a base.

11. The device of claim 10, wherein the cover includes a buzzer.

12. The device of claim 10, wherein the base includes at last one charging pad.

13. The device of claim 1, wherein the RP further comprises a motor, a drive screw, and at least one groove configured to prevent rotation of the drive screw during motor operation.

14. The device of claim 1, wherein the RP further comprising at least one gear.

15. The device of claim 14, wherein the at least one gear comprises a plurality of gears.

\* \* \* \* \*